US006540996B1

(12) United States Patent
Zwaal et al.

(10) Patent No.: US 6,540,996 B1
(45) Date of Patent: Apr. 1, 2003

(54) COMPOUND SCREENING METHODS

(75) Inventors: Richard Zwaal, Ghent (BE); José Groenen, St-Martens Latem (BE); Thierry Bogaert, Kortrijk (BE)

(73) Assignee: Devgen NV, Ghent-Zwijnaarde (BE)

( * ) Notice: Subject to any disclaimer, the term of this patent is extended or adjusted under 35 U.S.C. 154(b) by 0 days.

(21) Appl. No.: 09/549,872

(22) Filed: Apr. 14, 2000

Related U.S. Application Data

(60) Provisional application No. 60/129,596, filed on Apr. 15, 1999.

(30) Foreign Application Priority Data

| Apr. 15, 1999 | (GB) | 9908670 |
| Jun. 1, 1999 | (GB) | 9912736 |

(51) Int. Cl.[7] .................. A01N 63/00; A61K 48/00
(52) U.S. Cl. .............. 424/93.21; 800/3; 800/8; 800/13; 435/4
(58) Field of Search .............. 435/69.1; 800/8, 800/3; 424/93.4

(56) References Cited

U.S. PATENT DOCUMENTS 6,010,848 A * 1/2000 Delvecchio et al. .......... 435/5

FOREIGN PATENT DOCUMENTS

| WO | WO 90/09096 |   | 8/1990 |
| WO | WO 96/38555 |   | 12/1996 |
| WO | WO 98/53856 | * | 5/1998 |
| WO | WO 98/53856 |   | 12/1998 |
| WO | WO 99/02652 |   | 1/1999 |

OTHER PUBLICATIONS

JH Cho et al., Gene, "Two isoforms of sarco/endoplasmic reticulum calcium ATPase (SERCA) are essential in Caenorhabditis elegans," 2000, 261, pp. 211–219.*
Y Sagara et al., Journal of Biological Chemistry, "Characterization of the Inhibition of Intracellular Ca2+ Transport ATPases by Thapsigargin," 1992, vol. 267, No. 18, pp. 12606–12613.*
PA Sharp, Genes & Development, "RNAi and double–strand RNA," 1999, 13:139–141.*
AS Kraev, Locus Bank, Accession No. CAA09985, 1998.*
Arai, Masashi et al., "Alterations in Sarcoplasmic Reticulum Gene Expression in Human Heart Failure," *Circulation Research* (1993) vol. 72, No. 2, pp. 463–469.

Arai, Masashi, "Function and Regulation of Sarcoplasmic Reticulum $Ca^{2+}$–ATPase," *Jpn. Heart J.* (2000), vol. 41, No. 1, pp. 1–13.

Del Monte, Federica et al., "Restoration of Contractile Function in Isolated Cardiomyocytes from Failing Human Hearts by Gene Transfer of SERCA1a," *Circulation* (1999), 100:2308–2311.

Kiriazis, Helen et al., "Genetically Engineered Models with Alterations in Cardiac Membrane Calcium–Handling Proteins," *Annu. Rev. Physiol.* (2000), 62:321–51.

MacLennan, David et al., "Minireview: The Mechanism of $Ca^{2+}$–ATPases," *J. Biol. Chem.* (1997), 272:28815–28818.

Miyamoto, Michael et al., "Adenoviral Gene Transfer of SERCA2a Improves Left–Ventricular Function in Aortic–Banded Rats in Transition to Heart Failure," *PNAS* (2000), vol. 97, No. 2, pp. 793–798.

Moller, Jesper et al., "Structural Organization, Ion Transport, and Energy Transduction of P–Type ATPases," *Biochimica et Biophysica Acta* (1996) 1286, pp. 1–51.

Odermatt, Alex et al., "Mutations in the Gene–Encoding SERCA1, the Fast–twitch Skeletal Muscle Sarcoplasmic Reticulum $Ca^{2+}$ ATPase, are Associated with Brody Disease," *Nature Genetics* (1996) 14(2):191–4.

Sakuntabhai, Anavaj et al., "Mutations in ATP2A2, Encoding a $Ca^{2+}$ Pump, Cause Darier Disease," *Nature Genetics* (1999) vol. 21, pp. 271–277.

Schmidt, U et al., "Restoration of Diastolic Function in Senescent Rat Hearts Through Adenoviral Gene Transfer of Sarcoplasmic Reticulum $Ca^{2+}$–ATPase," *Circulation* (2000), 101:790–796.

Alexander Kraev et al., "Identification and Functional Expression of the Plasma Membrane Calcium ATPase Gene Family From *Caenorhabditis elegans*," *J. Biol. Chem.* (1999), vol. 274, No. 7, pp. 4254–4258.

* cited by examiner

*Primary Examiner*—Jeffrey Fredman
*Assistant Examiner*—Jon Eric Angell
(74) *Attorney, Agent, or Firm*—Wolf, Greenfield & Sacks, P.C.

(57) ABSTRACT

The invention provides methods of screening for compounds which affect the activity of a physiologically important calcium pump, the sarco/endoplasmic reticulum $Ca^{2+}$ ATPase (SERCA), using the nematode worm *C. elegans*.

19 Claims, 4 Drawing Sheets

FIG. 4.

```
GAACGAAATGCTGAATCGGCCATCGAAGCGCTCAAGGAATACGAACCAGAAATGGCCA
AGGTCATCCGATCCGGACACCACGGAATTCAGATGGTTCGCGCTAAGGAACTCGTGCC
AGGAGATCTTGTCGAAGTTTCAGgttagcaaaaactttttttttaactttcaaattt
taaaccatatattttttcagTCGGAGACAAGATCCCAGCCGATCTCCGTCTTGTGAAGA
TCTACTCCACCACCATCCGTATCGATCAGTCCATCCTCACCGGAGAATCTGTGTCTGT
TATCAAGCACACCGACTCTGTGCCAGATCCACGCGCTGTTAACCAGGACAAGAAGAAT
TGTCTGTTCTCGGGAACCAATGTCGCATCTGGAAAGGCTCGTGGAATCGTCTTCGGAA
CCGGATTGACCACTGAAATCGGAAAGATCCGTACCGAAATGGCTGAGACCGAGAATGA
GAAGACACCACTTCAACAGAAGTTGGACGAATTCGGAGAGCAACTTTCCAAGGTTATC
TCTGTTATTTGCGTTGCTGTTTGGGCTATCAACATTGGACATTTCAACGATCCAGCTC
ACGGTGGATCATGGGTTAAGGGAGCAATCTACTACTTCAAAATCGCCGTTGCTCTTGC
CGTCGCTGCTATTCCAGAAGGACTTCCAGCTGTCATCACCACGTGCCTTGCCCTCGGA
ACTCGCCGTATGGCCAAGAAGAACGCTATTGTAAGATCCCTTCCATCCGTCGAAACTC
TTGGATGCACATCTGTTATCTGCTCTGACAAGACTGGAACTCTCACCACCAACCAGAT
GTCTGTGTCAAAGATGTTCATCGCTGGACAAGCTTCTGGAGACAACATCAACTTCACC
GAGTTCGCCATCTCCGGATCCACCTACGAGCCAGTCGGAAAGGTTTCCACCAATGGAC
GTGAAATCAACCCAGCTGCTGGAGAATTCGAATCACTCACCGAGTTGGCCATGATCTG
CGCTATGTGCAATGATTCATCTGTTGATTACAATGAGACCAAGAAGATCTACGAGAAA
GTCGGAGAAGCCACTGAAACTGCTCTTATCGTTCTTGCTGAGAAGATGAATGTTTTCG
GAACCTCGAAAGCCGGACTTTCACCAAAGGAGCTCGGAGGAGTTTGCAACCGTGTCAT
CCAACAAAAATGGAAGAAGGAGTTCACACTCGAGTTCTCCCGTGATCGTAAATCCATG
TCCGCCTACTGCTTCCCAGCTTCCGGAGGATCTGGAGCCAAGATGTTCGTGAAGGGAG
CCCCAGAAGGAGTTCTCGGAAGATGCACCCACGTCAGAGTTAACGGACAAAAGGTTCC
ACTCACCTCTGCCATGACTCAGAAGATTGTTGACCAATGCGTGCAATACGGAACCGGA
AGAGATACCCTTCGTTGTCTTGCCCTCGGAACCATCGATACCCCAGTCAGCGTTAGCA
ACATGAACCTCGAAGACTCTACCCAATTCGTCAAATACGAACAAGACATCACATTTGT
CGGAGTCGTCGGAATGCTTGACCCCCAAGAACTGAAGTTTCGGACTCGATCAAGGCT
TGTAACCACGCTGGAATCCGTGTCATCATGATCACCGGAGACAACAAGAACACCGCTG
AGGCTATCGGAAGAAGAATCGGACTCTTCGGAGAGAACGAGGATACCACTGGAAAAGC
TTACACTGGACGTGAATTTGACGATCTTCCACCAGAGCAACAATCTGAAGCCTGCCGC
AGAGCTAAGCTTTTCGCCCGTGTCGAGCCATCTCACAAGTCCAAGATTGTCGATATCC
TTCAATCCCAGGGAGAGATTACTGCTATGACCGGAGACGGAGTCAACGACGCTCCAGC
TTTGAAGAAGGCCGAAATCGGAATTTCTATGGGATCAGGAACTGCTGTCGCCAAGTCT
GCATCTGAAATGGTTCTTGCTGACGATAACTTCGCATCCATTGTGTCTGCTGTCGAAG
AAGGACGTGCTATTTACAACAACATGAAACAATTCATCAGATATCTCATCTCATCTAA
CGTCGGAGAAGTCGTCTCCATCTTCATGGTCGCCGCACTCGGAATTCCAGAGGCTCTC
ATTCCAGTTCAACTTCTCTGGGTTAACTTGGTCACTGACGGTCTTCCAGCCACTGCTC
TCGGATTCAATCCACCAGATCTTGACATTATGGACAGACATCCACGTTCAGCCAACGA
TGGACTCATCTCTGGATGGCTCTTCTTCAGATATCTTGCTGTCGGAA
```

COMPOUND SCREENING METHODS

RELATED APPLICATIONS

This application claims priority under Title 35 §119(e) of U.S. Provisional Application No. 60/129,596, filed Apr. 15, 1999, and entitled COMPOUND SCREENING METHODS and foreign priority benefits under Title 35, U.S.C., §119(a)–(d) or §365(a),(b) of foreign patent application nos. GB 9908670.4, filed Apr. 15, 1999, and GB 9912736.7, filed Jun. 1, 1999, the entire contents of which are incorporated herein by reference.

The invention is concerned with methods for use in the identification of compounds which affect the activity of a physiologically important calcium pump, the sarco/endoplasmic reticulum $Ca^{2+}$ ATPase (SERCA).

In most animal cells and plant cells, the normal concentration of free cytosolic $Ca^{2+}$ is 50 to 100 nM. Since $Ca^{2+}$ acts as a major intracellular messenger, elevating these levels affects a wide range of cellular processes including contraction, secretion and cell cycling (Dawson, 1990, Essays Biochem. 25:1–37; Evans et al., 1991, J. Exp. Botany 42:285–303). Intracellular $Ca^{2+}$ stores hold a key position in the intracellular signalling. They allow the rapid establishment of $Ca^{2+}$ gradients, and accumulate and release $Ca^{2+}$ in order to control cytosolic $Ca^{2+}$ levels. Moreover, lumenal $Ca^{2+}$ intervenes in the regulation of the synthesis, folding and sorting of proteins in the endoplasmic reticulum (Brostrom and Brostrom, 1990, Ann. Rev. Physiol. 52:577–590; Suzuki et al., 1991, J. Cell. Biol. 114:189–205; Wileman et al., 1991, J. Biol. Chem. 266:4500–4507). Furthermore it controls signal-mediated and passive diffusion through the nuclear pore (Greber and Gerace, 1995, J. Cell. Biol. 128:5–14).

Three genes that code for five different isoforms of the sarco/endoplasmic reticulum $Ca^{2+}$ ATPase (SERCA) are known in vertebrates, SERCA1a/b, SERCA2a/b and SERCA3. The SERCA isoforms are usually tagged to the endoplasmic reticulum (ER) or ER subdomains like the sarcoplasmic reticulum, although the precise subcellular location is often not known. The SERCA proteins belong to the group of ATP-driven ion-motive ATPases, which also includes, amongst others, the plasma membrane $Ca^{2+}$-transport ATPases (PMCA), the Na+-K+-ATPases, and the gastric H+-K+-ATPases. The SERCA $Ca^{2+}$-transport ATPases can be distinguished from their plasma membrane counterparts like PMCA by the specific SERCA inhibitors: thapsigargin, cyclopiazonic acid, and 2,5-di(tert-butyl)-1,4-benzohydroquinone (Thastrup et al., 1990, PNAS 87:2466–2477; Seidler et al., 1989, J. Biol. Chem. 264:17816–17823; Oldershaw and Taylor, 1990, FEBS Lett. 274:214–216). In view of the diverse role of $Ca^{2+}$ in the cell and the fact that $Ca^{2+}$ is stored in diverse organelles, the diversity in $Ca^{2+}$-accumulation pump isoforms is not surprising.

SERCA1 is only expressed in fast-twitch skeletal muscle fibres. The gene encodes two different isoforms; SERCA1b which is the neonatal isoform and SERCA1a the adult isoform (Brandl et al., 1986, Cell 44:597–607; Brandl et al., 1987, J. Biol. Chem. 262:3768–3774). The difference between the two isoforms is the result of an alternative splice. As a consequence, the neonatal isoform contains a highly charged carboxyl-terminal extension (Korczak et al., 1988, J. Biol. Chem. 263:4813–4819). The reason for this alternative splicing is as yet unknown; the functional significance of this extension is not yet clear. When expressed in COS cells, SERCA1a and SERCA1b exhibit nearly identical maximal $Ca^{2+}$-turnover rate, $Ca^{2+}$-affinity and ATP-dependency of $Ca^{2+}$ transport (Maruyama and MacLennan, 1988, PNAS 85:3314–3318). The human SERCA1 gene is mapped on chromosome 16P12.1 and is about 26 kb long (MacLennan et al., 1987, Somatic Cell Mol. Genet. 13:341–346; Callen et al., 1991, Am. J. Hum. Genet. 49:1372–1377).

SERCA2 is expressed in muscle and non-muscle cells. The human SERCA2 gene maps to chromosome 12q23–q24.1 (Otsu et al., 1993, Genomics 17:507–509). Partial sequence analysis suggests that the same exon/intron layout is conserved between SERCA1 and SERCA2. mRNA of SERCA2 can be divided in 4 different classes; class 1 encodes SERCA2a and is mainly expressed in muscle, the other classes encode SERCA2b and are mainly expressed in non-muscle tissues. SERCA2b harbors a 49 amino acid extension, which contains a highly hydrophobic stretch. As with SERCA1, no functional difference can be measured between the two SERCA2 isoforms when expressed in COS cells (Campbell, 1991, J. Biol. Chem. 266:16050–16055). However, differences in $Ca^{2+}$ affinity and turnover rate of the phosphoprotein intermediate have been observed (Lytton et al., 1992, 267:14483–14489; Verboomen et al., 1992, J. Biochem. 286:591–596). Both isoforms are expressed in a tissue-dependent pattern, both qualitatively and quantitatively (Eggermont et al., 1990, J. Biochem. 271:649–653). Cardiac muscle expresses 5- to 20-fold higher levels of SERCA2 than smooth muscle. Slow-twitch skeletal and cardiac muscle only express SERCA2a, while SERCA2b (referred to as the "housekeeping" isoform) is expressed in all non-muscle tissue, and represents about 75% of the $Ca^{2+}$-transporting ATPase activity in smooth-muscle tissue. Different protein-to-message ratios for SERCA2a and SERCA2b have been observed. Cardiac muscle expresses 70 times more protein and only 7 times more SERCA2a mRNA compared to stomach smooth muscle which expresses SERCA2b (Khan et al., 1990, J. Biochem. 268:415–419).

SERCA3 is considered to be the non-muscle SERCA isoform. SERCA3 lacks the putative interacting domain for phospholamban, and hence, does not respond to this modulator (Toyofuku et al., 1993, J. Biol. Chem. 268:2809–2815). When expressed in COS cells, SERCA3 shows approximately 5-fold lower activity for $Ca^{2+}$ and a slightly higher pH optimum (Toyofuku et al., 1992, J. Biol. Chem. 267:14490–14496). In platelets, mast cells and lymphoid cells SERCA3 is co-expressed with SERCA2b (Wuytack et al., 1994, J. Biol. Chem. 269:1410–1416; Wuytack et al., 1995, Bioscience Rep. 15:299–306). Expression has also been observed in some arterial endothelial cells, in early developing rat heart, in some secretory epithelial cells of endodermal origin and in cerebellar Purkinje neurons.

In slow-twitch skeletal muscle, cardiac muscle and smooth-muscle tissues, SERCA2 activity is modulated by phosphorylation of the regulatory protein phospholamban (PLB) (see Fuji et al., 1991, FEBS Lett. 273:232–234). In cardiac muscle, in vivo phosphorylation of PLB by cAMP- or $Ca^{2+}$/Calmodulin-dependent protein kinase has a positive effect on the $Ca^{2+}$ transport (Le Peuch et al., 1997, Biochemistry 18:5150–5157; Tada et al., 1979, J. Biol. Chem. 254: 319–326; Davis et al., 1983, J. Biol. Chem. 258:13587–13591; Wegener et al., 1989, J. Biol. Chem. 264:11468–11474). In order to determine the exact in vivo role of phospholamban, PLB-deficient mice have been generated (Luo et al., 1994, Circ. Res. 75:401–409). A marked effect is observed on $Ca^{2+}$ uptake, whereas no effect is measured in Vmax. The ablation of the PLB gene in mice is associated with increased myocardial contractility, and a loss of the positive inotropic response to adrenergic stimulation. The precise molecular mechanism underlying the modulation of SERCA by PLB is not apparent. An electrostatic mechanism has been proposed, as a direct interaction between PLB and SERCA, in which the unphosphorylated PLB inhibits the SERCA pump (Kirchberger et al., 1986, Biochemistry 25:5484–5492; Chiesi and Schwaller, 1989, FEBS Lett. 244:241–244; Xu and Kirchberger, 1989, J. Biol. Chem. 264:16644–16651). Alternatively, PLB and the SERCA $Ca^{2+}$ pump are able to interact and phosphorylation of PLB alters its properties, as confirmed by cross-linking experiments (James et al., 1989, Nature 342:90–92). In some experiments, inhibitory effects of PLB have been observed on co-transfection of PLB and SERCA2a in COS-1 cells (Fuji et al. 1990, FEBS Lett. 273:232–234). Several models have been proposed to explain the regulatory effect of PLB on $Ca^{2+}$ ATPases. These include the aggregation of SERCA2 around a pentameric form of PLB (Voss et al., 1994, Biophys J. 67:190–196). Another explanation starts from the electrostatic inhibition of $Ca^{2+}$ binding due to the SERCA-PLB interaction (Toyoftiku et al., 1994, J. Biol. Chem. 269:3088–3094). The interaction between PLB and SERCA2a has been studied in more detail, revealing a putative PLB binding domain that is also present SERCA1 but not in SERCA3. This has been further confirmed by expression studies in COS-1 cells (Toyofuku et al., 1993, J. Biol. Chem., 268:2809–2815). Such a finding is remarkable as SERCA1 and PLB are never co-expressed in vivo.

Direct phosphorylation of SERCA by $Ca^{2+}$/CaM kinase II results in a 2-fold higher maximal velocity Xu and Kirchberger, 1989, J. Biol. Chem. 264: 16644–16651. This CaM kinase phosphorylation is specific for SERCA2 and may act synergistically with the phosphorylation of phospholamban.

Sarcolipin (SLN) is a peptide of 33 amino acids in length that co-purifies with SERCA1. The human gene encoding SLN was mapped to chromosome 11q22–q23. The protein sequence shows some homology to phospholamban, especially in the lumenal part of the protein. In rabbits SLN is highly expressed in fast-twitch skeletal muscle, as is SERCA1 (Odermatt et al., 1997, Genomics 45:741–553). In co-expression studies in HEK-293 T-cells, a decrease of SERCA1 affinity for $Ca^{2+}$ was observed, but maximal $Ca^{2+}$ uptake rates were stimulated. Mutational analysis provided evidence for different mechanisms of interaction of both SLN and PLB with the SERCA molecules (Odermatt, et al., 1998, J. Biol. Chem. 273:12360–12369).

SERCA plays an important role in regulating $Ca^{2+}$ levels, and hence in pathologies related to abnormal $Ca^{2+}$ concentrations and regulation. For instance, abnormal cytosolic free $Ca^{2+}$ levels are involved in different muscle pathologies (Morgan, 1991, N. Engl. J. Med. 325:625–632; Perreault et al., 1993, Circulation 87 Suppl. VII:31–37). Other major pathologies in which SERCA may play a role include cardiac hypertrophy, heart failure, and hypertension (Arai et al., 1994, Circ. Res. 74:555–564; Lompre et al., 1994, J. Mol. Cell. Cardiol. 26:1109–1121).

Cardiac hypertrophy is an adaptive response of the cardiac muscle to a hemodynamic overload, in which diastolic dysfunction is one of the earliest signs of pathological hypertrophic response. In animal models, where most studies are performed, a highly significant positive correlation has been obtained between end-diastolic cytosolic $Ca^{2+}$ levels and diastolic relaxation abnormalities. After aortic binding, SERCA2 mRNA and protein levels are decreased, as is the sarcoplasmic reticulum $Ca^{2+}$ uptake (Komuro et al., 1989, J. Clin Invest. 83:1102–1108; de la Bastie et al., 1990, Circ. Res. 66:554–564). This effect was only found in cases of severe hypertrophy, and was only observed when heart failure occurs. In moderate hypertropy and in cases of compensated hypertrophy no changes in the level of SERCA mRNA were observed (de la Bastie et al, ibid; Feldman et al., 1993, Circ. Res. 73:184–192).

In humans, most studies report a decrease in SERCA2 mRNA, SERCA2 protein levels and decreased $Ca^{2+}$ uptake in a failing heart (Arai et al., 1993, Circ. Res. 72:463–469; Hasenfuss et al., 1994, Circ. Res., 75: 434–442). The decreased levels of SERCA2 expression are accompanied by decreased expression of phospholamban, cardiac ryanodine receptor and dihydropyridine receptor (Vatner et al., 1994, Circulation 90:1423–1430; Go et al., 1995, J. Clin. Invest. 95:888–894; Takahashi et al., 1992, J. Clin. Invest. 90:927–935). These human heart failure data are confirmed in different animal models. In a hypertrophic animals, SERCA2 expression levels are decreased; in a dilated strain $Ca^{2+}$ uptake is decreased with increasing age (Kuo et al., 1992, Biochem Biophys acta 1138:343–349; Whitmer et al., 1988, Circ. Res. 62:81–85). Most striking in both humans and animal models is the strong positive correlation between SERCA2 and phospholamban mRNA levels. Examples in literature that do not confirm these data are most likely the result of various pathogenic mechanisms that can lead to heart failure.

Blood vessels from hypertensive animals have an increased wall thickness and show altered contractile properties. Several lines of evidence indicate that diminished $Ca^{2+}$ pump activities might contribute to elevation in cytoplasmic $Ca^{2+}$ levels in hypertension. However, increased expression of SERCA2 has also been observed. Further study is required to resolve these contradictory results.

Darier-White disease is an autosomal-dominant skin disorder characterized by loss of adhesion between epidermal cells (acantholysis) and abnormal keratinization. In several patients mutations have been found in SERCA2, demonstrating the role of SERCA and $Ca^{2+}$-signalling pathway in the regulation of cell-to-cell adhesion and differentiation of the epidermis (Sakuntabhai et al., 1999, Nature Genetics 21:271–277).

Although little is known about the involvement of SERCA in skeletal muscle disorders, deficiency in the $Ca^{2+}$-transport ATPase activity has been found in Brodys disease (Benders et al., 1994, J. Clin. Res. 94:741–748). The disorder is characterized by exercise-induced impairment of muscle relaxation. Normal levels of SERCA1 protein were detected, but the SERCA activity was decreased by about 50% in patients suffering from the disease. In other research, SERCA1 in fast-twitch fibers of Brody patients could not be detected immunologically (Danon et al., 1988, Neurology 38:812–815). However, three Brody patients show no defects in their SERCA1 gene, indicating pleiotropic mechanisms underlying Brody disease (Zhang et al., 1995, Genomics 30:415–424).

The underlying mechanism of non-insulin-dependent diabetes mellitus (NIDDM) is still unknown. In islets of Lagerhans from db/db mice (a NIDDM model), glucose-induced initial induction and subsequent oscillations of intracellular $Ca^{2+}$ concentrations were absent. Further analysis showed that SERCA3 was almost entirely lacking from the db/db islets. These results and thapsigargin experiments implicate SERCA3 in the defective insulin secretion associated with NIDDM (Roe et al., 1994, J. Biol. Chem. 269:18279–28282). A significant reduction of SERCA3 expression was also found in Goto-Kakizaki rats, a non-obese model of NIDDM (Varadi et al., 1996, J. Biochem. 319:521–527) Interactions have been reported between different SERCAs (SERCA1 and SERCA2) and different Insulin Receptor Substrates (IRS-1 and IRS-2). This interaction was dependant on insulin (Algenstaedt et al., 1997, J. Biol. Chem. 272:23696–23702). Inactivation of IRS-2 has recently been shown to resemble certain aspects of type 2 diabetes (Withers et al., 1998, Nature 391:900–904).

In mammals, there are three genes encoding different SERCA isoforms. In contrast, the nematode worm *Caenorhabditis elegans* (*C. elegans*) has only a single homologue of the mammalian SERCA protein, which was identified by the *C. elegans* genome-sequencing consortium (see Science issue 282, 1998). The *C. elegans* SERCA gene is located on chromosome III on a cosmid named K11D9. On a physical level, the gene consists of six exons that span an Open Reading Frame of 3.2 kb, resulting in a predicted protein of 1059 amino acids. The consensus alternative splice site that is present in the C-terminal end of mammalian SERCA genes is present in the worm as well. This leads to a second isoform consisting of 7 exons that span an ORF of 3.0 kb, resulting in a protein of 1004 amino acids. This may indicate a functional conservation of this domain of the protein, e.g. in regulating the activity of the SERCA pump.

*C. elegans* is a small roundworm that has a life span of only three days, allowing rapid accumulation of large quantities of individual worms. The cell-lineage is fixed, allowing identification of each cell which has the same position and developmental potential in each individual animal. *C. elegans* is extremely amenable to genetic approaches and a large collection of mutants have been isolated that are defective in embryonic development, behaviour, morphology, neurobiology etc. There is also a large cosmid collection covering almost the whole *C. elegans* genome, which is used to determine the complete genomic sequence of the worm.

These characteristics of *C. elegans* make it the organism of choice for use as a tool in the drug discovery process. In particular, *C. elegans* may be used in the development of high throughput live animal compound screens, useful in the development of potential candidate drugs, in which worms are exposed to the compound under test and any resultant phenotypic and/or behavioural changes are recorded. The present inventors have developed a number of *C. elegans*-based screening methods which may be used to identify compounds which modulate the activity of SERCA, either directly or via the SERCA/PLB interaction. Compounds identified as modulators of SERCA activity using these screening methods may be useful as pharmaceuticals in the treatment of the wide range of diseases with which the SERCA genes have been associated.

Accordingly, in a first aspect the invention provides a method of identifying compounds which are capable of enhancing or up-regulating the activity of a sarco/endoplasmic reticulum calcium ATPase, which method comprises:

contacting *C. elegans* which exhibit reduced SERCA ATPase activity compared to wild type *C. elegans* in one or more cell types or tissues with a compound under test; and detecting a phenotypic, biochemical or behavioural change in the *C. elegans* indicating a reversion towards wild type SERCA activity in the one or more cell types or tissues which exhibit reduced SERCA activity in the absence of the compound.

The method of the invention, which will be hereinafter referred to as the 'up-regulation assay' is performed using a *C. elegans* strain which exhibits reduced SERCA ATPase activity in one or more cell types or tissues, as compared to the SERCA ATPase activity in wild-type *C. elegans*. It has been observed that worms which exhibit reduced SERCA activity compared to wild-type worms manifest a variety of phenotypic and behavioural defects. The basis of the up-regulation assay is therefore to take worms which exhibit defects due to reduced SERCA activity, contact these worms with the compound under test and screen for phenotypic, behavioural or biochemical changes indicating a reversion towards wild-type SERCA activity. For example, worms with reduced SERCA activity often show a reduction in the rate of pharynx pumping. In this case, screening for an increase in the rate of pharynx pumping in the presence of a test compound would indicate a reversion towards wild-type SERCA activity due to the ability of the compound to enhance or up-regulate SERCA. For comparison purposes, an example of a *C. elegans* strain which exhibits 'wild-type' SERCA activity is the N2 strain (this strain can be obtained from CGC, University of Minn., USA). The N2 strain has been particularly well characterised in the literature with respect to properties such as pharynx pumping rate, growth rate and egg laying capacity (see Methods in Cell Biology, Volume 48, *Caenorhabditis elegans:* Modern biological analysis of an organism, ed. by Henry F. Epstein and Diane C. Shakes, 1995 Academic Press; The nematode *Caenorhabditis elegans,* ed. by William Wood and the community of *C. elegans* researchers., 1988, Cold Spring Harbor Laboratory Press; *C. elegans* II, ed. by Donald L. Riddle, Thomas Blumenthal, Barbara J. Meyer and James R. Priess, 1997, Cold Spring Harbor Laboratory Press.).

*C. elegans* which exhibit reduced SERCA activity in one or more cell types or tissues can be obtained in several different ways. In a first embodiment, worms with reduced SERCA activity are obtained by treating a culture of worms with a chemical inhibitor of SERCA such as, for example, thapsigargin. As will be demonstrated in the examples given herein, treatment of *C. elegans* with thapsigargin results in recognisable phenotypic and behavioural changes such as paleness, reduced growth, pharynx pumping defects and production of very few progeny which are sick and grow very slowly. Accordingly, reversion of any one of these characteristics towards wild-type can provide an indication of a reversion towards wild-type SERCA activity.

In another embodiment, worms with reduced SERCA activity can be produced by specifically down-regulating the expression of SERCA in one or more tissues using antisense techniques or double stranded RNA inhibition. This can be achieved by transfection of *C. elegans* with a vector that expresses either an antisense *C. elegans* SERCA RNA or double stranded *C. elegans* SERCA RNA. Specific down-regulation of SERCA expression in different cell types or tissues of the worms can be achieved by incorporating into the vector an appropriate tissue-specific promoter to drive expression of the antisense RNA or double stranded RNA in the required tissues. SERCA expression will be specifically down-regulated only in those tissues which express the antisense RNA or double stranded RNA. By way of example, the promoter region of the *C. elegans* SERCA gene itself (see the examples given below) can be used to direct expression of an antisense RNA or double stranded RNA in all the cells and tissues which express SERCA. The *C. elegans* myo-2 promoter can be used to direct expression in the pharynx. The *C. elegans* myo-3 promoter can be used to direct expression in the body wall muscles. The use of antisense and double stranded RNA inhibition will be further understood with reference to the Examples included herein.

Alternative RNAi techniques which may be used to inhibit SERCA activity are described in the applicant's co-pending International patent application No. WO 00/01846. These techniques, which are based on delivery of dsRNA to C. elegans by feeding with an appropriate dsRNA or feeding with food organisms which express an appropriate dsRNA, may lead to a more stable RNAi phenotype than results from injection of dsRNA.

In a still further embodiment, the C. elegans exhibiting reduced SERCA ATPase activity in one or more cell types or tissues may be a mutant strain in which SERCA activity is reduced but not eliminated i.e. a reduction-of-function mutant. The mutation may give rise to reduced SERCA activity through a down-regulation of SERCA expression in one or more cell types or tissues or through a defect in the SERCA protein itself or a defect in regulation of the activity of the SERCA protein.

A reduction-of-function mutant or a knock-out mutant can be isolated using a classical non-complementation screen, starting with a heterozygote C. elegans strain carrying a mutant SERCA allele on one chromosome and a recessive marker close to the wild-type SERCA allele on the other chromosome. The worms are subjected to mutagenesis using standard techniques (EMS or UV-TMP are suitable for this purpose) and the progeny is screened by eye for defects, especially in tissues which express SERCA. Since the screening is performed in the F1 generation, mutations will only give rise to a phenotype if the mutation occurs in the SERCA gene (due to non-complementation) or if the mutation is dominant, which does not occur frequently. These two possibilities can be distinguished in subsequent generations. A newly introduced SERCA mutation should be linked to the recessive marker. As a further control, DNA sequencing can be performed to determine the nature of the mutation.

The step of 'detecting a phenotypic, biochemical or behavioural change in the C. elegans indicating a reversion towards wild type SERCA activity' may be performed in several different ways. The method of choice is generally dependent upon the phenotype/behavioural characteristics of the starting worm strain, which is in turn generally dependent upon the nature of the cell types or tissues in which SERCA activity is reduced.

Inhibition experiments, for example the RNAi experiments and thapsigargin experiments described herein, demonstrate that SERCA is a vital protein for C. elegans. Moreover, reduction of SERCA activity results in a variety of phenotypes that can be used as basis of an assay to isolate compounds that alter the activity of SERCA. The main defects, and hence phenotypes, associated with reduced SERCA activity are related to muscle function e.g pharyngeal muscle, body wall muscle, vulva muscle, anal repressor muscle, and anal sphincter muscle. Screens based on reversion of defects in these muscles to wild-type can be used to identify compounds and genes that alter the activity of SERCA. Moreover, other phenotypes, such as paleness, reduced growth, reduced progeny, protruding vulva and protruding rectum can be used to identify compounds and genes that alter the function of SERCA.

In one embodiment, particularly suitable for use when the starting worm strain exhibits defects in pharynx pumping due to reduced SERCA activity in the pharynx (as compared to wild-type C. elegans) the up-regulation assay can be based on detection of changes in the pharynx pumping efficiency. If the starting worm strain exhibits a reduced rate of pharynx pumping due to reduced SERCA activity in the pharynx, then an increase in the rate of pharynx pumping in the presence of a test compound can be used as an indicator of a reversion towards wild-type SERCA activity in the pharynx.

C. elegans feeds by taking in liquid containing its food (e.g. bacteria). It then spits out the liquid, crushes the food particles and internalises them into the gut lumen. This process is performed by the muscles of the pharynx. The process of taking up of liquid and subsequently spitting it out, requiring contraction and relaxation of muscles, is called pharyngeal pumping or pharynx pumping.

Alterations in SERCA activity influence the pharyngeal pumping rate. In particular, inhibition of SERCA using thapsigargin causes a reduction in the rate of pharynx pumping. Measurement of the pumping rate of the C. elegans pharynx is hence a method to determine the activity of SERCA. The pharynx pumping efficiency can be conveniently measured by placing the nematodes in liquid containing a fluorescent marker molecule precursor, such as calcein-AM. Calcein-AM present in the medium is taken up by the nematodes and the AM moiety is cleaved off by the action of esterases present in the C. elegans gut, resulting in the production of the fluorescent molecule calcein. As the quantity of calcein-AM that is delivered in the gut is dependent of the pumping rate of the pharynx, and hence of the activity of SERCA, the fluorescence measured in the gut of the formed calcein is a quantitative and qualitative measurement of the SERCA activity. It would be readily apparent to one skilled in the art that other types of marker molecule precursor which are cleavable by an enzyme present in the gut of C. elegans to generate a detectable marker molecule could be used instead of calcein-AM with equivalent effect.

In further embodiments, particularly suitable for use when the starting worm strain exhibits reduced SERCA activity in the vulva muscles, the up-regulation assay can be based on detection of changes in the egg laying behaviour of the C. elegans or on detecting changes in the amount of progeny produced by the C. elegans.

Defects associated with reduced SERCA activity in the vulva muscles include defects in the production and laying of eggs and hence a reduction in the number of progeny produced. Typically, worms with reduced SERCA expression in the vulva are not able to lay their eggs. The eggs thus hatch inside the mother, which then dies. These mothers are easy to recognize under the dissection microscope. As a consequence of the egg laying defect, these worms produce less progeny, and hence the culture as a whole grows much more slowly. Defects associated with reduced SERCA activity have also been observed in the gonad, including the sheath cells and the spermatheca. These defects also result in reduced egg formation and hence a reduced egg laying phenotype.

One convenient way in which the egg production and egg laying behaviour of the worms can be monitored is by counting the number of resultant offspring produced. A variety of different techniques can be used for this purpose. For example, the offspring can be measured directly using the growth rate assay and/or the movement assay described below. Alternatively, specific antibodies and fluorescent antibodies can be used to detect the offspring. Any specific antibody that only recognizes eggs, or L1 or L2 or L3 or L4 stage worms, will only recognize offspring, such a specific antibody that recognizes an antigen on the L1 surface has been described by Donkin and Politz, W13G 10(2):71. Finally, the number of eggs or offspring in each well can be counted directly using a FANS device. The FANS device is a 'worm dispenser apparatus' having properties analogous to flow cytometers such as fluorescence activated cell scanning and sorting devices (FACS) and is commercially available from Union Biometrica, Inc, Somerville, Mass., USA. The FANS device, also designated a nematode flow meter, can be the nematode FACS analogue, described as fluorescence activated nematode scanning and sorting device (FANS). The FANS device enables the measurement of nematode properties, such as size, optical density, fluorescence, and luminescence and the sorting of worms based on these properties.

In a still further embodiment, particularly suitable for use when the starting worm strain exhibits reduced SERCA activity in the anal sphincter or the anal repressor, the up-regulation assay can be based on detection of a change in the defecation behaviour of the C. elegans.

A reduction in the SERCA activity in the anal sphincter and/or the anal repressor, for example following treatment with thapsigargin, results in worms which are constipated and also in worms with a protruding rectum. Changes in the defecation rate of the worms can therefore also serve as an indicator of SERCA activity.

Defecation rate can be measured using an assay similar to that described above for the measurement of pharynx pumping efficiency, but using a marker molecule which is sensitive to pH. A suitable marker is the fluorescent marker BCECF. This marker molecule can be loaded into the C. elegans gut in the form of the precursor BCECF-AM which itself is not fluorescent. If BCECF-AM is added to worms growing in liquid medium the worms will take up the compound which is then cleaved by the esterases present in the C. elegans gut to release BCECF. BCECF fluorescence is sensitive to pH and under the relatively low pH conditions in the gut of C. elegans (pH<6) the compound exhibits no or very low fluorescence. As a result of the defecation process the BCECF is expelled into the medium which has a higher pH than the C. elegans gut and the BCECF is therefore fluorescent. The level of BCECF fluorescence in the medium (measured using a fluorimeter on settings Ex/Em=485/550) is therefore an indicator of the rate of defecation of the nematodes.

Defecation can also be measured using a method based on the luminescent features of the chelation of terbium by aspirin. The method requires two pre-loading steps, first the wells of a multi-well plate are pre-loaded with aspirin (prior to the addition of the nematode worms) and second, bacteria or other nematode food source particles are pre-loaded with terbium using standard techniques known in the art. C. elegans are then placed in the wells pre-loaded with aspirin and are fed with the bacteria pre-loaded with terbium.

The terbium present in the pre-loaded bacteria added to the wells will result in a low level of background luminescence. When the bacteria are eaten by the nematodes the bacterial contents will be digested but the terbium will be defecated back into the medium. The free terbium will then be chelated by the aspirin which was pre-loaded into the wells resulting in measurable luminescence. The luminescence thus observed is therefore an indicator of nematode defecation.

It has been observed that a reduction in SERCA activity, for example using inhibition by thapsigargin or double stranded RNA inhibition, results in a reduction in the growth rate of a C. elegans culture. Growth rate of the culture as a whole is reduced because the worms produce fewer progeny and also because the few progeny that are produced show poor/delayed growth. Cultures of worms which produce many healthy progeny grow faster than cultures of worms with few and/or sick progeny. Hence measurement of the growth rate of a culture of C. elegans is in indication of the activity of SERCA in the individual worms of the culture.

Growth rate can be monitored by measuring the number of eggs or the number offspring present in the culture, by measuring the total fluorescence in the culture (this can be autoflourescence, or fluorescence caused by a transgene encoding a flourescent or luminescent protein), but can also be measured using the movement screen described below. Alternatively, the growth rate of a culture of C. elegans can also be assayed by measuring the turbidity of the culture. In order to perform this 'turbidity assay' the worms are grown in liquid culture in the presence of E. coli or other suitable bacterial food source. As the culture of worms grows the food source bacteria will be consumed. The greater the number of worms in the culture, the more food source bacteria will be digested. Hence, measurement of the turbidity or optical density of the liquid culture will provide an indirect indication of the number of worms in the culture. By taking sequential measurements over a period of time it is possible to monitor the growth rate of the whole C. elegans culture.

As an alternative to the above-described methods, the growth rate and amount of progeny can be measured on a plate. Slow growing nematodes, nematodes with vulva defects and nematodes with gonad defects will produce less progeny within a certain time compared to nematodes which do not have these defects. Preferentially, the amount of offspring produced is scored on day five and on day eight. In experiments where the amount of offspring is reduced very drastically due to severe defects in the vulva, gonad or growth rate reduction, the offspring can also be scored at later time intervals.

In a still further embodiment, the up-regulation assay can be performed by detecting changes in the movement behaviour of C. elegans. As is illustrated by the examples included herein, SERCA is widely expressed in the muscles of C. elegans, including the muscles of the body wall. A reduction of SERCA activity in the body wall muscles gives rise to worms with movement defects. These strains can be used as the basis of an assay in which the worms are contacted with a compound under test and any changes in the movement behaviour of the worms are observed. Compounds which cause the defective movement to revert towards wild-type movement behaviour are scored as compounds capable of enhancing/up-regulating the activity of SERCA.

Changes in the movement behaviour of the worms can obviously be detected by visual inspection, but as an alternative a number of non-visual approaches for analysing the movement behaviour of worms have been developed which can be performed in a multi-well plate format and are therefore suitable for use in high-throughput screening. Nematode worms that are placed in liquid culture will move in such a way that they maintain a more or less even (or homogeneous) distribution throughout the culture. Nematode worms that are defective in movement will precipitate to the bottom in liquid culture. Due to this characteristic of nematode worms as result of their movement phenotype, it is possible to monitor and detect the difference between nematode worms that move and nematodes that do not move. Advanced multi-well plate readers are able to detect sub-regions of the wells of multi-well plates. By using these plate readers it is possible to take measurements in selected areas of the surface of the wells of the multi-well plates. If the area of measurement is centralized, so that only the middle of the well is measured, a difference in nematode autofluorescence (fluorescence which occurs in the absence of any external marker molecule) can be observed in the wells containing a liquid culture of nematodes that move normally as compared to wells containing a liquid culture of nematodes that are defective for movement. For the wells containing the nematodes that move normally, a low level of autofluorescence will be observed, whilst a high level of autofluorescence can be observed in the wells that contain the nematodes that are defective in movement.

In an adaptation of the movement assay, autofluorescence measurements can be taken in two areas of the surface of the well, one measurement in the centre of the well, and on measurement on the edge of the well. Comparing the two measurements gives analogous results as in the case if only the centre of the well is measured but the additional measurement of the edge of the well results in an extra control and somewhat more distinct results.

As an alternative to the above-described embodiments of the up-regulation assay which are all based on the observation of changes in phenotypic and/or behavioural characteristics of the C. elegans as an indicator of SERCA activity, the inventors have developed a method of analysing SERCA activity in a given cell type or tissue which is based upon the use of the marker molecule apoaequorin which is sensitive to changes in intracellular $Ca^{2+}$.

Aequorin is a calcium-sensitive bioluminescent protein from the jellyfish *Aequorea victoria*. Recombinant apoaequorin, which is luminescent in the presence of calcium but not in the absence of calcium, is most useful in determining intracellular calcium concentrations and even calcium concentrations in sub-cellular compartments. Expression vectors suitable for expressing recombinant apoaequorin and, in addition, vectors expressing apoaequorin proteins which are targeted to different sub-cellular compartments, for example the nucleus, the mitochondria or the endoplasmic reticulum are available commercially (see below).

As SERCA is a endoplasmic reticulum-localized calcium pump, an apoaequorin that is targeted to the endoplasmic reticulum (hereinafter referred to as erAEQ) is particularly useful for developing assays for SERCA activity. Such apoaequorin is available from Molecular probes (Eugene, Oreg., USA). The vector erAEQ/pcDNAI (Molecular Probes) contains an Ig 2b heavy chain gene from mouse, an HA1 epitope and a recombinant apoaequorin in fusion. The mouse gene targets the aequorin to the endoplasmic reticulum, and the aequorin is mutated to make it less sensitive to calcium, as the concentrations of this ion are relatively high in the endoplasmic reticulum. Although apoaequorin is the calcium sensor of choice, it would be apparent to persons skilled in the art that any other calcium sensor localized in the endoplasmic reticulum could be used with equivalent effect Plasmid expression vectors which drive expression of the ER-localized apoaequorin in C. elegans can be easily constructed by cloning nucleic acid encoding erAEQ downstream of a promoter capable of directing gene expression in one or more tissues or cell types of C. elegans, such that the promoter and the erAEQ-encoding sequence are operatively linked. As used herein the term "operatively linked" refers to a juxtaposition wherein the components described are in a relationship permitting them to function in their intended manner. In a typical cloning procedure, the apoaequorin gene in fusion with the signals to locate the resulting protein to the endoplasmic reticulum was isolated from erAEQ/pcDNAI by EcoRI digestion and cloned into pBlue2SK. The erAEQ was then isolated as an EcoRI/Acc65I fragment by partial digestion and cloned in the vector pGK13 digested with the same enzymes.

Suitable promoters include the pharynx-specific promoter myo-2, the C. elegans SERCA promoter which directs expression in a wide range of muscle tissues and the body wall muscle-specific promoter myo-3. The vectors can then be used to construct transgenic C. elegans according to the standard protocols known to those of ordinary skill in the art. Expression of erAEQ allows for the determination of the calcium levels in the endoplasmic reticulum of various C. elegans cells and tissues, using the protocols of the manufacturer of erAEQ, or minor modifications thereof. Alterations in SERCA activity influence the concentration of calcium in the endoplasmic reticulum as SERCA functions as an endoplasmic reticulum calcium pump. Hence the apoaequorin luminescence measured in the assay is directly related to SERCA activity.

The basic 'up-regulation assay' methodology can also be adapted to perform a genetic screen in order to identify C. elegans which carry a mutation having the effect of enhancing or up-regulating the activity of SERCA. Accordingly, the invention also provides a method of identifying C. elegans which carry a mutation having the effect of enhancing or up-regulating the activity of a sarco/endoplasmic reticulum calcium ATPase, which method comprises:

subjecting a population of C. elegans with wild-type SERCA activity to random mutagenesis;

allowing the mutagenized C. elegans to grow for one or two generations;

treating the mutagenized C. elegans to reduce the activity of the SERCA ATPase in one or more cell types or tissues; and scoring a phenotypic, biochemical or behavioural characteristic of the C. elegans as an indicator of SERCA ATPase activity in the C. elegans in the said one or more cell types or tissues.

This genetic screen differs from the 'up-regulation' assay used to identify compounds in that the C. elegans are subjected to a random mutagenesis step before they are treated to reduce the activity of the SERCA ATPase. The random mutagenesis step can be performed using any of the techniques known in the art. EMS and UV-TMP mutagenesis, both of which are well known in the art (see Methods in Cell biology Vol. 48, 1995, ed. by Epstein and Shakes, Academic press) are preferred. After mutagenesis the worms are grown for one or two generations before they are treated to reduce the activity of SERCA. After one generation, the worms are heterozygous for any mutation, after two generations they may be homozygous or heterozygous for any mutation. Therefore growth for one generation leads to isolation of dominantly acting suppressors, growth for two generations yields both recessively and dominantly acting suppressors.

The step of treating the C. elegans to reduce the activity of the SERCA ATPase preferably comprises either treating the worms with a chemical inhibitor of SERCA, for example thapsigargin, or specifically down-regulating the expression of SERCA using antisense or double-stranded RNA inhibition.

When thapsigargin is added to worms in plate or liquid culture few progeny are produced and these don't grow as well as wild-type worms. To perform a genetic screen based on thapsigargin inhibition wild-type worms are first subjected to standard mutagenesis protocols (using EMS or UV/TMP or any other mutagen). F1 or F2 progeny of the mutagenized worms are distributed individually to standard growth medium with bacteria, to which 10 to 50 mM thapsigargin is added. After 4–8 days the cultures are inspected for growth of progeny, either by eye or using the 'turbidity assay', as described above. Wild-type C. elegans with an integrated transgenic array causing general expression of a reporter protein such as GFP can also be used. In this case, cultures are inspected for growth of progeny either by eye or by detecting expression of the reporter protein.

Thapsigargin causes a short term pharynx pumping defect. Hence, the genetic screen can also be performed by measuring changes in the pharynx pumping efficiency. Wild-type worms are mutagenized and grown on solid media according to standard techniques known in the art. Adults are washed off the plates and put in buffer with calcein-AM and thapsigargin (an assay buffer of 40 mM NaCl, 6 mM KCl, 1 mM $CaCl_2$, 1 mM $MgCl_2$ can be used for this purpose). After two hours the worms are viewed under a fluorescence microscope and individual worms that show far brighter gut fluorescence than the other worms are selected, placed individually onto fresh plates and grown for an additional generation. Calcein-AM uptake in the presence of thapsigargin is then re-checked.

Inhibition of SERCA by antisense or double stranded-RNA inhibition will result in the same phenotypes as described above for the up-regulation assay and hence the same screens can be used to select for mutants that enhance or up-regulate SERCA activity. The precise nature of the screen used depends on the tissue in which the antisense or double stranded SERCA RNA is expressed.

An analogous genetic screen can also be performed using a reduction-of-function mutant C. elegans strain which exhibits reduced C. elegans activity in one or more cell types or tissues. Accordingly, in a further aspect the invention provides a method of identifying C. elegans which carry a mutation having the effect of enhancing or up-regulating the activity of a sarco/endoplasmic reticulum calcium ATPase, which method comprises the steps of:

subjecting a population of mutant C. elegans which exhibit reduced SERCA activity in one or more cell types or tissues to random mutagenesis;

allowing the mutagenized C. elegans to grow for one or two generations; and scoring a phenotypic, biochemical or behavioural characteristic of the C. elegans as an indicator of SERCA ATPase activity in the C. elegans in the said one or more cell types or tissues.

A suitable reduction-of-function mutant strain can be isolated as described above.

The basis of the above-described genetic screens is to screen for mutations that have the effect of enhancing or up-regulating SERCA activity and thus suppress the inhibitory effect of thapsigargin treatment, antisense or double stranded RNA inhibition of SERCA expression or a reduction-of-function mutation. Mutations likely to be identified using the method of the invention include mutations in genes involved in transcription and/or translation of SERCA, mutations that influence $Ca^{2+}$ cycling between the ER and cytoplasm, mutations that influence $Ca^{2+}$ buffering and mutations that influence the activity of $Ca^{2+}$ binding proteins. Once a mutant worm has been identified using a genetic screen it is a matter of routine to identify the mutated gene using techniques commonly used in the art.

In summary, the up-regulation assay which may be used to identify compounds which enhance the activity and/or expression of SERCA is based on the use of C. elegans worms in which the activity or expression of the C. elegans SERCA protein is reduced. This may be achieved in at least three different ways. First, mutants can be selected that show reduced SERCA activity. Second, wild-type, mutant, or transgenic C. elegans strains can be treated with compounds that inhibit SERCA activity, such as thapsigargin. Third, RNAi technology can be applied to wild-type, mutant or transgenic C. elegans to reduce the SERCA activity. In each case, screening can be performed to select for compounds that enhance SERCA activity. Such screens may be based on the pharynx pumping rate, egg laying or movement. In a particular example of the up-regulation assay, wild-type, mutant or transgenic strains can be made transgenic for apoaequorin or another calcium marker. These markers may be expressed in the various tissues, such as the pharynx, the body wall muscles, the oviduct, vulva-muscles etc, for which specific promoters are known in the art. Apoaequorin may also be expressed more generally in C. elegans, for instance under the control of the SERCA promoter. The apoaequorin may further be fused to a specific signal peptide translocating the apoaequorin to the endoplasmic reticulum. Selecting compounds that enhance the activity or the expression of SERCA will enhance calcium uptake, and hence increase the bio-luminescence of the apoaequorin located in the lumen of the endoplasmic or sarcoplasmic reticulum.

In a second aspect the invention provides a method of identifying compounds which modulate the interaction between a sarco/endoplasmic reticulum calcium ATPase and phospholamban, which method comprises:

exposing transgenic C. elegans which contains a first transgene comprising nucleic acid encoding a vertebrate PLB protein and which expresses a SERCA protein to a compound under test; and detecting a phenotypic, biochemical or behavioural change in the transgenic C. elegans indicating an increase in the activity of the SERCA protein.

The vertebrate phospholamban (PLB) protein used in this second method of the invention, hereinafter referred to as the 'interaction assay' can be any vertebrate PLB protein. Most preferred are pig PLB (GenBank P07473) or human PLB (GenBank P26678) or a humanized pig PLB (see below). Mutant PLB proteins which exhibit stronger or weaker inhibition of SERCA relative to the wild-type protein may also be used.

The SERCA protein expressed by the C. elegans may be a C. elegans SERCA protein, a vertebrate SERCA protein, a fusion between a vertebrate SERCA protein and C. elegans SERCA protein or a mutant SERCA protein, for example a mutant which exhibits greater sensitivity to PLB.

The vertebrate SERCA protein can be any vertebrate SERCA isoform. Preferred isoforms are pig SERCA2a (GenBank P11606), human SERCA1a (GenBank AAB 53113), human SERCA1b (GenBank AAB 53112), human SERCA2a (GenBank P16614) and human SERCA2b (GenBank P16615). Human and pig SERCA2a are most preferred.

Various types of fusion proteins between C. elegans SERCA and vertebrate SERCA proteins which may be used in the method of the invention are described in the accompanying Examples. For example, the fusion might comprise the N-terminal part of C. elegans SERCA and the C-terminal part of a vertebrate SERCA.

It is essential that a 'functional' combination of SERCA and PLB is chosen i.e. that the SERCA protein and the PLB protein are able to interact with each other such that the activity of SERCA can be inhibited by the PLB, mimicking the regulatory interaction occurring in vertebrates.

In the context of this application the term "transgene" refers to a DNA construct comprising a promoter operatively linked to a protein-encoding DNA fragment. The construct may contain additional DNA sequences in addition to those specified above. The transgene may, for example, form part of a plasmid vector. By the term "operatively linked" it is to be understood that the promoter is positioned to drive transcription of the protein-encoding DNA fragment.

Methods of preparing transgenic *C. elegans,* including worms carrying multiple transgenes, are well known in the art and are particularly described by Craig Mello and Andrew Fire, Methods in Cell Biology, Vol 48, Ed. H. F. Epsein and D. C. Shakes, Academic Press, pages 452–480. A typical approach involves the construction of a plasmid-based expression vector in which a protein-encoding DNA of interest is cloned downstream of a promoter having the appropriate tissue or cell-type specificity. The plasmid vector is then introduced into *C. elegans* of the appropriate genetic background, for example using microinjection. In order to facilitate the selection of transgenic *C. elegans* a second plasmid carrying a selectable marker may be co-injected with the experimental plasmid.

The plasmid vector is maintained in cells of the transgenic *C. elegans* in the form of an extrachromosomal array. Although plasmid vectors are relatively stable as extrachromosomal arrays they can alternatively be stably integrated into the *C. elegans* genome using standard technology, for example, using gamma ray-induced integration of extrachromosomal arrays (methods in Cell Biology, Vol 48 page 425–480).

The DNA fragment encoding the SERCA protein or the PLB protein may be a fragment of genomic DNA or cDNA. Preferably the DNA encoding the vertebrate SERCA protein is operatively linked to the promoter region of a SERCA gene. Most preferably the promoter region of the *C. elegans* SERCA gene is used. The term 'promoter region' as used herein refers to a fragment of the upstream region of a given gene which is capable of directing a pattern of gene expression substantially identical to the natural pattern of expression of the given gene.

Provided that a functional combination is chosen, wherever the SERCA protein and the vertebrate PLB are co-expressed the two proteins will interact such that PLB inhibits the activity of SERCA. The aim of the interaction assay is to identify compounds which directly or indirectly disrupt the SERCA/PLB interaction, leading to an increase in SERCA activity. The increase in SERCA activity is monitored indirectly, by detecting phenotypic, biochemical or behavioural changes in the *C. elegans* which are indicative of an increase in SERCA activity. Advantageously, the nucleic acid encoding PLB is operatively linked to a tissue-specific promoter. With the use of a promoter of appropriate specificity, the vertebrate PLB can be expressed in all the cells of *C. elegans,* in a given type of tissue (i.e. all muscles), in a single organ or tissue (for example, the pharynx or the vulva), in a subset of cell types, in a single cell type or even in a single cell.

By restricting the expression of PLB to certain tissues it is possible to specifically down-regulate SERCA activity in these tissues and thus to influence the phenotype of the resultant transgenic worms. For example, when PLB is expressed in the pharynx, the resultant inhibition of SERCA activity in the pharynx results in a reduction in the rate of pharynx pumping. When PLB is expressed in the vulva muscles, the resultant inhibition of SERCA activity in the vulva results in an egg laying defect.

Although the interaction assay may be performed using functional combinations of *C. elegans* SERCA (especially mutant versions thereof, as discussed below) and vertebrate PLB, it is preferred to use functional combinations of vertebrate SERCA and vertebrate PLB. In order to ensure that the interaction assay can be used to identify compounds which specifically modulate the vertebrate SERCA/vertebrate PLB interaction it is preferred to use a transgenic strain which has been modified such that expression of the endogenous *C. elegans* SERCA protein is abolished or substantially reduced down to background levels. This may be achieved by introducing the transgenes encoding the vertebrate SERCA and PLB into a mutant strain having a knock-out or loss-of-function mutation in the chromosomal *C. elegans* SERCA gene (e.g. strain ok190 described in the accompanying Examples). A protocol for isolating a suitable knock-out mutant strain is given in the examples included herein. In a variation of this approach, expression of the endogenous *C. elegans* SERCA gene may be abolished/reduced using RNAi technology, as described hereinbefore. In this case, the genetic background of the transgenic *C. elegans* may be wild-type.

In a further embodiment, a vertebrate-specific interaction assay may be achieved by using transgenic *C. elegans* expressing a mutant version of the vertebrate SERCA protein which is resistant to a chemical inhibitor of SERCA activity, such as thapsigargin. The mutation Phe259Val renders *C. elegans* SERCA resistant to inhibition with thapsigargin. Equivalent mutations may be introduced into transgenes encoding the vertebrate SERCA proteins using standard site-directed mutagenesis. Applying the SERCA inhibitor, e.g. thapsigargin, to transgenic *C. elegans* which express a resistant mutant vertebrate SERCA and a vertebrate PLB will result in inhibition of the endogenous *C. elegans* SERCA only. Thus, if the inhibitor is added to the interaction assay in addition to the test compound, the screen will be specific for the interaction between the vertebrate SERCA and the vertebrate PLB.

A particular variant of the interaction assay uses a mutant version of the *C. elegans* SERCA protein which is more sensitive to vertebrate PLB proteins, such as, for example, a *C. elegans* SERCA containing the KDDKPV (SEQ ID NO:39) insertion. As illustrated in the accompanying Example 9, introduction of the amino acid sequence KDDKPV (SEQ ID NO:39) into the *C. elegans* SERCA protein results in a more efficient interaction between the mutant SERCA and vertebrate PLB. Therefore, double transgenic *C. elegans* strains containing a first transgene encoding a vertebrate PLB protein and a second transgene encoding a *C. elegans* SERCA KDDKPV (SEQ ID NO:39) insertion mutant may be used in the interaction assay.

In order to provide specificity for the mutant SERCA/PLB interaction, it is preferred that the double transgenic is also modified such that expression of the endogenous *C. elegans* SERCA gene is abolished or substantially reduced. As described above, this may be achieved by using a mutant *C. elegans* genetic background having a knock-out or loss-of-function mutation in the chromosomal SERCA gene or by using RNAi technology to inhibit SERCA expression. Alternatively, it is possible to engineer the mutant SERCA so that in addition to the KDDKPV (SEQ ID NO:39) insertion it also carries a firther mutation which renders it resistant to a SERCA inhibitor other than PLB, e.g. the thapsigargin resistance mutation Phe259Val. Addition of the SERCA inhibitor, e.g. thapsigargin, to the assay will result in specific inhibition of the endogenous *C. elegans* SERCA protein but not the resistant mutant.

As with the 'up-regulation assay' described above, the step of "detecting a phenotypic, biochemical or behavioural change in the transgenic C. elegans indicating an increase in the activity of SERCA" can be performed in several different ways.

In one embodiment, particularly suitable for use when the transgenic C. elegans expresses PLB in the pharynx, the method is performed by detecting changes in the pharynx pumping efficiency. The rate of pharynx pumping can be measured using a marker molecule precursor such as calcein-AM, as described above for the up-regulation assay.

In still further embodiments, particularly suitable for use when the transgenic C. elegans expresses PLB in the vulva, the method can be performed by detecting changes in the egg laying behaviour of the C. elegans or by detecting changes in the number of progeny produced by the C. elegans. The number of progeny produced by the C. elegans can, as described above in connection with the up-regulation assay, be directly counted or can be measured indirectly using a growth assay or a turbidity assay.

In a still further embodiment, again particularly suitable for use when the transgenic C. elegans expresses PLB in the pharynx, SERCA activity in cells of the C. elegans pharynx can be monitored using apoaequorin luminescence. To achieve this the C. elegans are transfected with a third transgene which comprises nucleic acid encoding an apoaequorin protein, preferably ER-targeted apoaequorin, operatively linked to promoter capable of directing gene expression in the C. elegans pharynx. The construction of suitable expression vectors comprising such a transgene has been described hereinbefore.

In summary, the basic SERCA-PLB interaction screen to select for compounds that inhibit the interaction between SERCA and PLB is based on the construction of transgenic C. elegans expressing PLB. The PLB may be of any vertebrate origin, such as human or pig. The PLB may be expressed ubiquitously or in specific tissues, such as the pharynx, the body wall muscles, the oviduct, vulva muscles etc, for which specific promoters are known in the art. Preferred configurations of the interaction assay are summarised below, however, this is not intended to be limiting to the scope of the invention:

Double transgenic C. elegans, first transgene encoding a vertebrate PLB, second transgene encoding a vertebrate SERCA; expression of endogenous C. elegans SERCA abolished/reduced by mutation of the SERCA gene in the genetic background or by using RNAi on wild-type genetic background, Double transgenic C. elegans, first transgene encoding a vertebrate PLB, second transgene encoding a fusion between C. elegans SERCA and a vertebrate SERCA; expression of endogenous C. elegans SERCA abolished/reduced by mutation of the SERCA gene in the genetic background or by using RNAi on wild-type genetic background, Double transgenic C. elegans, first transgene encoding a vertebrate PLB, second transgene encoding a mutant vertebrate SERCA which is resistant to a SERCA inhibitor other than PLB, e.g. thapsigargin; wild-type genetic background; inhibitor is added to the assay in addition to the compound under test to specifically inhibit endogenous C. elegans SERCA expression, Double transgenic C. elegans, first transgene encoding a vertebrate PLB, second transgene encoding a mutant C. elegans SERCA which is more sensitive to inhibition by ivertebrate PLB (e.g. KDDKPV (SEQ ID NO:39) insertion); expression of endogenous C. elegans SERCA abolished/reduced by mutation of the SERCA gene in the genetic background or by using RNAi on wild-type genetic background, Double transgenic C. elegans, first transgene encoding a vertebrate PLB, second transgene encoding a double mutant C. elegans SERCA which is (i) more sensitive to inhibition by vertebrate PLB (e.g. KDDKPV (SEQ ID NO:39) insertion) and (ii) resistant to inhibition by a SERCA inhibitor such as thapsigargin (e.g. Phe259Val); wild-type genetic background; inhibitor is added to the assay in addition to the compound under test to specifically inhibit endogenous C. elegans SERCA expression.

In a third aspect the invention provides a method of identifying compounds capable of down-regulating the activity of a sarco/endoplasmic reticulum calcium ATPase, which method comprises:

exposing transgenic C. elegans containing a transgene comprising nucleic acid encoding a SERCA protein operatively linked to a promoter capable of directing gene expression to a sample of the compound under test; and detecting a phenotypic, biochemical or behavioural change in the transgenic C. elegans indicating a decrease in the activity of the SERCA protein.

The SERCA protein used in this third aspect of the invention, hereinafter referred to as the 'down-regulation assay' can be any SERCA isoform from any species. Preferably the SERCA protein is C. elegans SERCA, pig SERCA2a, or a human SERCA isoform, most preferably human SERCA 2A.

Preferably the nucleic acid encoding the SERCA protein is operatively linked to a tissue-specific promoter. Most preferably, the tissue-specific promoter is the C. elegans myo-2 promoter which directs tissue-specific expression in the pharynx.

In a preferred embodiment the transgenic C. elegans further contain a second transgene comprising nucleic acid encoding a reporter protein operatively linked to a promoter which is capable of directing gene expression in one or more cell types or tissues of C. elegans. The reporter protein is preferably an autonomous fluorescent protein, for example, a green fluorescent protein or a blue fluorescent protein or a luminescent protein.

Transgenic C. elegans over-expressing SERCA are generally observed to be starved and show delayed growth. Compounds which reduce or down-regulate the activity of SERCA will cause a reversion or reduction of this phenotype towards a wild-type phenotype. Accordingly, these worms can be used as a basis of a screen to identify compounds capable of reducing or down-regulating the activity of SERCA, by bringing the worms into contact with the compound under test and then detecting a reversion of the over-expression phenotype reflecting a decrease in the activity of the SERCA transgene.

The step of "detecting a phenotypic, biochemical or behavioural change in the transgenic C. elegans indicating a decrease in the activity if the SERCA protein" can be performed in several different ways. As mentioned above, transgenic C. elegans which overexpress the SERCA protein exhibit delayed growth. Accordingly, it is possible to look for a reversion of the overexpression phenotype by comparing the growth rate of the transgenic C. elegans in the presence and the absence of the compound under test. Compounds which increase the growth rate of the C. elegans culture are scored as compounds which are capable of reducing or down-regulating SERCA activity. Any of the growth assay methods described in connection with the 'up-regulation' assay could be used for this purpose.

Transgenic *C. elegans* which overexpress SERCA also exhibit altered egg laying behaviour and reduced pharynx pumping. Hence, the down-regulation assay can also be performed by detecting changes in the egg laying behaviour or the pharynx pumping efficiency, as described previously.

In summary, the basic down-regulation assay consists of introducing extra SERCA into *C. elegans* and screening for a compound that inhibits SERCA activity. The SERCA introduced into *C. elegans* may be *C. elegans* SERCA or a SERCA of any vertebrate origin, such as human or pig. The SERCA protein may be expressed ubiquitously or in specific tissues such as the pharynx, the body wall muscles, the oviduct, the vulva muscles etc, for which appropriate tissue or cell type-specific promoters are known in the art.

The above-described methodology for the down-regulation assay can be adapted to perform a genetic screen to identify *C. elegans* carrying a mutation having the effect of reducing or down-regulating SERCA activity. Thus, in a further aspect the invention provides a method of identifying *C. elegans* which carry a mutation having the effect of reducing or down-regulating the activity of a sarco/endoplasmic reticulum calcium ATPase, which method comprises the steps of:

providing a transgenic *C. elegans* strain containing a first transgene comprising nucleic acid encoding a SERCA protein operatively linked to a promoter capable of directing gene expression in one or more cell types or tissues of *C. elegans*;

subjecting a population of the said *C. elegans* strain to random mutagenesis;

allowing the mutagenized *C. elegans* to grow for one or more generations; and scoring a phenotypic, biochemical or behavioural characteristic of the *C. elegans* as an indicator of SERCA ATPase activity in the *C. elegans* in the said one or more cell types or tissues.

The genetic screen is preferably carried out using transgenic *C. elegans* containing an integrated transgene harboring 20–50 ng/µl pGK7 (containing the *C. elegans* genomic SERCA gene, including the promoter region, see examples given below) and a general GFP expressing construct. These worms are starved and show general growth delay. The same results are obtained using a vertebrate SERCA, such as the human or pig SERCA.

Alternatively, the screen can be performed using transgenic nematodes containing an integrated transgene harboring the genomic *C. elegans* SERCA gene operatively linked to the myo-2 promoter, and a general GFP expressing construct. These worms are also starved and show growth delay.

The worms are grown and subjected to random mutagenesis according to standard techniques known in the art. The mutagenized worms then are distributed individually to standard growth medium with supplemented with food source bacteria. After 4–8 days the cultures are inspected for growth of progeny, either by eye, by using any of the growth assay techniques mentioned previously in connection with the up-regulation assay, using the turbidity assay or by counting the numbers of progeny produced.

The basis of these genetic screens is that mutations having the effect of reducing or down-regulating SERCA activity will suppress the effect of SERCA over-expression. Mutations identified using this screen may include mutations in genes involved in transcription and/or translation of SERCA, mutations that influence $Ca^{2+}$ cycling between the ER and the cytoplasm, mutations that influence $Ca^{2+}$ buffering and mutations that influence the activity of $Ca^{2+}$ binding proteins.

In the field of human pharmaceuticals, compounds identified as modulators of SERCA activity using the screening methods of the invention may be useful leads in the development of pharmaceuticals for the treatment of the wide range of diseases with which the SERCA genes have been associated, such as cardiac hypertrophy, heart failure, hypertension, NIDDM, Darier-White disease, Brody's disease.

Outside the pharmaceutical field, compounds identified as modulators of SERCA activity may find important applications as pesticides, particularly insecticides, herbicides or nematocides. Maintaining high calcium concentrations in the ER is important for the proper synthesis of protein, including translation, folding, glycosylation, processing and transport. Treatment of living organisms with chemicals that inhibit the activity of SERCA will hence have a negative effect on the welfare of these organisms. As such, SERCA inhibitors are potential pesticides or can be considered as basic compounds for the development of pesticides such as herbicides, insecticides and nematocides. It has been shown that SERCA function is essential in the intracellular trafficking of the Notch receptor in drosophila (Periz et al., 1999 EMBO J; 5983–5993). This studies and others indicate that SERCA is an interesting target for pesticidal intervention. Accordingly, the screening methods described herein could be applied to screen for pesticides.

The invention will be further understood with reference to the following experimental Examples together with the accompanying Figures in which.

Figure 3:
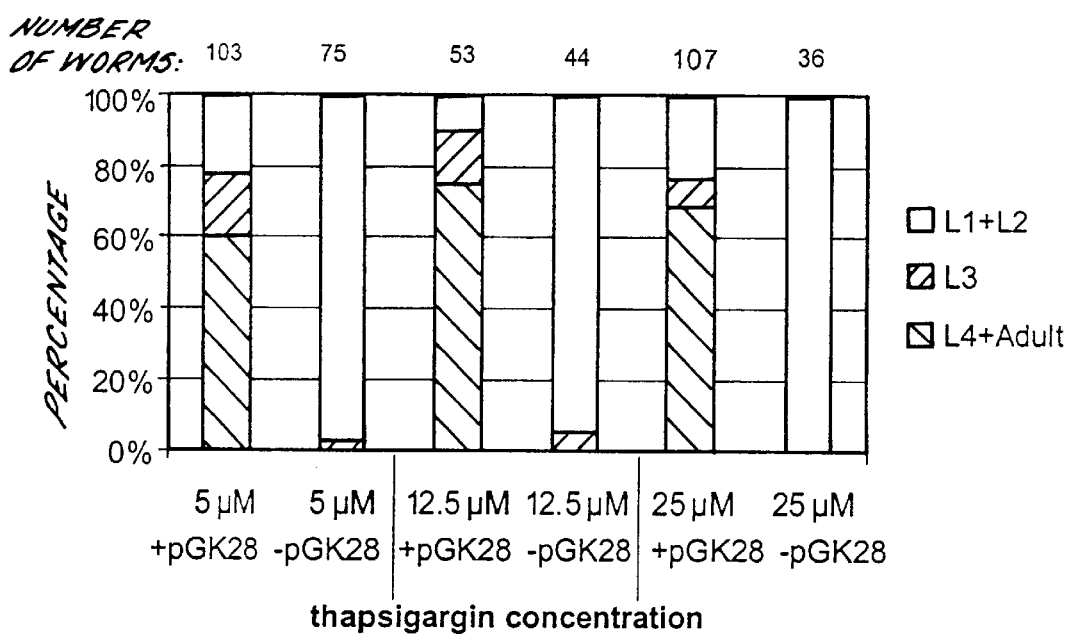

FIG. 3 illustrates the growth of *C. elegans* strain UG530 (strain harboring plasmid pGK28) on different concentrations of thapsigargin. The stage of the progeny was determined 5 days after adults were put on the plates. Since the mothers carry the pGK28 containing plasmid on an extra-chromosomal transgene, part of the progeny inherited it and part of the progeny did not. These were differentiated based on a GFP marker also present on this transgene.

FIG. 4 illustrates the nucleotide sequence of the genomic fragment of *C. elegans* SERCA bounded by primers SERCA P4 and SERCA P8. Exon IV and exon V are shown in capitals, intron IV in lower case. The fragment deleted in ok190 is underlined.

All Molecular biology work was performed as described by Sambrook et al. Molecular cloning, A Laboratory Manual, Cold Spring Harbor Laboratory Press, or using minor modifications of the methods described therein.

All manipulations of *C. elegans* worms were performed using techniques described in Methods in Cell Biology, vol 84; *Caenorhabditis elegans*: modern biological analysis of an organism, ed. Epstein and Shakes, academic press, 1995, or using minor modifications of the methods described therein.

Transgenic *C. elegans* strains were constructed by injection of plasmid DNA into worms using standard techniques known in the art (see Methods in Cell Biology, vol 84 as mentioned above).

EXAMPLE 1
Inhibition of Expression of C. elegans SERCA Using RNAi 732 bp EcoRI-HindIII fragment from C. elegans SERCA exon 5 (SEQ ID NO: 1) was PCR amplified and cloned into the vector pGEM3 (PROMEGA corporation, Madison, Wis., USA). RNA was in vitro transcribed from both strands using standard procedures. The generated double stranded RNA was injected into C. elegans (see Fire at al., 1998, Nature 391:806–811). This resulted in the following phenotypes: 50% of the progeny of the injected animals were embryonic lethal, while the other 50% were early larval lethal. This indicates that SERCA function is vital for C. elegans. In conclusion, inhibition of the expression of SERCA in all tissues results in embryonic or early larval lethality of the nematode.

Inhibition of SERCA Using RNAi Feeding Technology

Although injection of SERCA dsRNA results in a clear phenotype, useful in the development of assays to select for compounds that alter the SERCA activity, or that alter the activity of partners in the SERCA pathway, or that alter the activity proteins involved in calcium metabolism, a more stable RNAi phenotype would be more efficient. Improved RNAi methods which lead to more stable RNAi phenotypes exist and are described, for example in International patent application No. WO 00/01846. More particularly, an RNAi technology has been developed and tested in which dsRNA can be delivered by feeding the nematode dsRNA or by feeding nematodes with DNA.

pGN4 was constructed by cloning the HindIII-EcoRI fragment of SERCA cloned in vector pGN1 using these same restriction sites. This is the same fragment as was used for in vitro transcription and dsRNA injection, described above.

HT115(DE3) bacteria (Fire A, Carnegie Institution, Baltimore, Md.) were transfected with pGN4 (and controls with pGN1) and seeded on plates containing IPTG and ampicillin resulting in a high expression of dsRNA by the bacteria. N2 and nuc-1 (e1392) adult nematodes were put on these plates and allowed to lay eggs and the progeny was followed over time. The progeny mostly looked healthy during the larval stages, but the adults (and some of the L4) had a starved appearance (nuc-1 more pronounced then N2). Pumping was irregular and slower then normal, and the growth rate was somewhat reduced. This example indicates that a stable RNAi phenotype useful in assay development and compound screening can be developed using feeding. As described in co-pending application No. WO 00/01846, other possibilities and variants can be used to create a C. elegans SERCA RNAi phenotype. The use of RNAi technology allows the development of screens for compounds that alter SERCA activity or that alter the SERCA pathway, without the construction of a C. elegans SERCA mutant.

E. coli HT115 has the following characteristics which make it a useful host cell for high level expression of dsRNA: HT115 (DE3): F-mcrA mcrb IN(rrD-rrnE) 1—rnc14::tr10 (DE3 lysogen: lacUV5 promoter-T7 polymerase); host for IPTG inducible T7 polymerase expression; RnaseIII-. Other host strains suitable for expression of dsRNA could be used with equivalent effect.

EXAMPLE 2
Overexpression of C. elegans SERCA

A 11207 bp SpeI-MluI fragment from the cosmid K11D9 (SEQ ID NO:2) was cloned into the vector pUC18 (Messing, J., 1998, Methods in Enzymol. 101: 20), resulting in the plasmid pGK7. This genomic fragment contains the complete SERCA gene with 5631 bp upstream sequences, the complete coding region and 1088 bp downstream sequences. Transfection of C. elegans with this vector using standard technology resulted in various results. Transfection with high concentrations of DNA (80–200 ng/µl) induced embryonic lethality. At lower concentrations of DNA (20–50 ng/µl) worms were generally sick; also they were constipated, showed a starved appearance, and had pharynx pumping defects. These experiments indicate the importance of fine-tuning the expression level of SERCA in the nematode C. elegans. High levels of overexpression of SERCA is lethal, as is inhibition of expression. Furthermore, intermediate levels of overexpression of SERCA results in defects all over the worm, affecting almost all vital functions.

EXAMPLE 3
Expression Pattern of SERCA in C. elegans

A 5026 bp fragment of the upstream region of the C. elegans SERCA gene, starting 5026 bp upstream of the translation initiation codon and continuing up to and including the A of the ATG initiation codon (SEQ ID NO:3), was cloned into the vector pPD95.79 (described in Fire et al. (1990) Gene, 93: 189–198)in fusion with a GFP fluorescent protein, resulting in vector pGK10. The cloned fragment can be considered as the promoter region of the C. elegans SERCA. The vector was injected into C. elegans, using standard methodology well known to persons skilled in the art, and the expression of the GFP was monitored applying standard fluorescent techniques. GFP expression was observed all over the early embryo of the worm, although expression was faint in some tissues. In a later stage of development, from mid-embryo stage, through larval stage to adult stage, strong GFP expression could be observed in all muscle tissue, including the pharyngeal muscles, the body wall muscles, the anal depressor and the anal sphincter. In adults staining was seen in the vulva muscles, the uterine muscles, the spermatecae and the proximal myoepithelial sheath cells of the gonad.

A construct containing a smaller promoter fragment, including A of the initiating ATG codon and extending 2915 bp upstream (SEQ ID NO:4), fused to a GFP gene was generated by a PstI deletion of the plasmid pGK10. This plasmid was designated pGK13. Transfection of the nematode with pGK13 resulted in the same pattern of GFP expression as was observed with pGK10.

Finally, a third construct was made containing a 6612 bp fragment of the C. elegans SERCA gene in the plasmid pPD95.75 (described in Fire et al. (1990) Gene, 93: 189–198). The resultant plasmid was designated pGK12. This 6612 bp fragment contains 5637 bp of upstream sequences an ends in exon 4 of the C. elegans SERCA gene (SEQ ID NO:5). The fragment was cloned as a SalI-BglII fragment isolated from pGK7, and cloned in fusion to GFP. This fragment contains two transmembrane domains of SERCA. Transfection of C. elegans with this construct resulted in the same pattern of GFP expression as was observed with pGK10 and pGK13, i.e. GFP expression could be localized to the muscle tissues of C. elegans. Detailed analysis of the expression pattern in the muscles showed clearly that the GFP protein was localized to the endoplasmic reticulum and the dense bodies.

These expression studies clearly demonstrate that the SERCA protein of C. elegans is expressed in all muscle tissue, and that it is localized in the endoplasmic reticulum, indicating that the C. elegans SERCA probably has analogous function to the vertebrate SERCAs.

In addition to pGK10, pGK12 and pGK13, several further constructs have been used to analyse the pattern of SERCA expression in C. elegans. These are summarised as follows:

pGK26 contains GFP inserted directly after the CDS of C. elegans SERCA isoform A using overlap PCR, also containing the SERCA downstream region.

pGK27 contains GFP inserted directly after the CDS of the *C. elegans* SERCA isoform B using overlap PCR, also containing the SERCA downstream region.

pGK26 was constructed by the following strategy: Three separate PCR reactions were done to yield three PCR fragments that are joined in consequent overlap PCR. The first fragment is made with the oligonucleotides oGK25 and oGK26 and contains the region upstream of where GFP is inserted. The primer oGK26 is an overlap primer and contains the last 21 nt of SERCA until but not including the stop codon followed by the first 15 nt of GFP. The second fragment contains the complete ORF of GFP including the stop codon. The third fragment is made with oGK27 and oGK28 and contains the region downstream of where GFP is inserted. The primer oGK27 is an overlap primer and contains the last 15 nt of GFP including the stop codon and the first 22 nt of the 3' UTR. The end result after overlap PCR is a "recombination" of these three fragments in which GFP is inserted exactly after and in-frame with the SERCA coding region such that the fragment encodes a SER-CA::GFP fusion protein. This PCR fragment is cloned into pGK7 to replace the normal C-terminus of the gene using unique restriction sites in the SERCA coding region and 3' UTR (ApaI in the first fragment and PacI in the third fragment).

pGK27 was constructed the same way, using primers oGK21 and oGK22 instead of oGK25 and oGK26, and primers oGK23 and oGK24 instead of primers oGK27 and oGK28.

Sequence of Primers oGK21: TGGACTCATCTCTGGATGGCTC (SEQ ID NO:17)
oGK22: CTTCTCCTTTACTCATCAATTCGTTATG-TAACTTGTCGG (SEQ ID NO:18)
oGK23: GAACTATACAAATAGTTGAAGTTCT-TCTAACCCCC (SEQ ID NO:19)
oGK24: GCGTTTATCCTTGATTGGAGCTTC (SEQ ID NO:20)
oGK25: GAATGGATCGCCGTGTTGAAG (SEQ ID NO:21)
oGK26: TTCTCCTTTACTCATGTCGCGTTTATC-CTTGATTGG (SEQ ID NO:22)
oGK27: GAACTATACAAATAGAAATGACAGT-GCTCCCTCAATC (SEQ ID NO:23)
oGK28: GTGGGATCCTGGTTTGTTCTGAG (SEQ ID NO:24)

When the various constructs were injected into wild-type *C. elegans* the following expression patterns were observed:

Expression was observed in all muscle types, such as the body wall muscle, the pharynx, the vulva muscle, the uterine muscles etc, but expression was also observed in the anal depressor, the gut, the gonad sheath cells etc. (see Table 1). This is not unexpected, due to the importance of SERCA in the calcium metabolism of *C. elegans*, as has also been observed in other organisms. Moreover the various constructs give different expression patterns, indicating complex regulation of SERCA expression as suggested.

The expression patterns of the constructs, and hence of the endogenous SERCA, indicate that various assays can be developed. These include assays based on body wall muscle function and hence on movement, assays on pharyngeal function and hence on the pumping rate, assays on vulva muscle function and hence on egg laying, assays on anal repressor finction and hence on defecation, assays on the gonad sheath cell, uterine muscle and uterine sheath cell function and hence on egg laying.

TABLE 1 expression patterns for SERCA constructs in wild-type *C. elegans*

|  | pGK10 | pGK26 | pGK27 |
| --- | --- | --- | --- |
| body wall/head muscle | Yes | Yes | Yes |
| ER | No | Yes | Yes |
| dense bodies | No | Yes | Yes |
| mucle arms | Yes | No | No |
| pharnyx | Yes | Yes | Yes |
| TB | Yes | Yes | Yes |
| isthmus | Yes | Yes | Yes |
| metacorpus | No | No | No |
| procorpus | No | No | No |
| vulva muscles | Yes | Yes | Yes |
| anal depressor | Yes | Yes | Yes |
| gonad sheath cells | Yes | Yes | Yes |
| gut | Yes | Yes | Yes |
| uterine muscles | Yes | ? | ? |
| uterine sheath cells | No | No | Yes |
| spermatheca | Yes | No | Yes |
| tailspike | Yes | No | Yes |
| coelomocytes | No | No | Yes |
| excretory canal | No | No | Yes |

EXAMPLE 4

Expression of Mammalian SERCA in *C. elegans*

Further constructs were made in which the pig SERCA2a cDNA was cloned under the regulation of the *C. elegans* SERCA promoter. Suitable constructs can easily be made by replacing the GFP sequences in pGK10 or pGK13 with the coding region of the pig SERCA2a cDNA. The sequence of the pig SERCA2a cDNA is shown in SEQ ID NO:7. *C. elegans* were transfected with plasmid pGK101, harboring the pig SERCA2a cDNA under the control of the worm SERCA promoter derived from pGK 10 by injection of the plasmid at a concentration of 100 ng/μl, resulting in the overexpression of the pig SERCA2a in all *C. elegans* muscles. The overexpression of this vertebrate SERCA protein results in embryonic lethality, L1 arrest and growth delay, effects which are quite analogous to the overexpression of *C. elegans* SERCA.

The pig SERCA2a was also expressed in *C. elegans* under the control of the myo-2 promoter (pGK201), which is specific for induction of expression in the pharyngeal muscles. Overexpression of SERCA2a in the pharyngeal muscles resulted in apparently normal healthy lines, although a slight growth delay was observed. In a pharynx pumping assay, with the fluorescent dye precursor calcein-AM, it was shown that the nematode pumps with a slightly lower efficiency than a wild-type strain.

Expression in *C. elegans* of the pig SERCA2a under the regulation of the myo-3 promoter, which directs gene expression in the body wall muscles, resulted in apparently normal, healthy lines, with no apparent movement defects.

EXAMPLE 5

Expression of Mammalian Phospholamban (PLB) in *C. elegans*

Human, humanized and pig PLB fused and not fused to GFP were expressed under the myo-2 promoter in the pharyngeal muscles. The transfected nematodes appeared sick, showed a reduced growth and a clearly reduced pharynx pumping phenotype. Further generations of offspring seem to be healthier and perform in a pharynx pumping assay as wild-type worms.

Expression of the PLB-GFP fusion protein in the body wall muscles, was done under the regulation of the myo-3 promoter. Expression of the fusion protein could clearly be localized to the endoplasmic reticulum and the dense bodies, but no clear phenotype could be observed.

EXAMPLE 6

Construction of a Mutated SERCA C. elegans

Strategy 1

The following strategy may be used to isolate a nematode that is mutated in the SERCA gene, using standard selection procedures well known in the art. A population of nematodes are mutagenized, preferentially using UV-TMP, and grown for two generations. The mutagenized worms are distributed per 500 over approximately 1152 plates and grown for an additional two generations. DNA is isolated from a fraction of the worms from each of these plates and used as a template for PCR selection to select for a SERCA gene that has a deletion. From a plate with worms, of which some have been demonstrated to contain a SERCA deletion, new plates are started with fewer worms. Further rounds of PCR selection finally result in the isolation of a heterozygote C. elegans carrying a mutation in the SERCA gene (see Jansen et al., 1997, Nature Genetics 17:119–121). As the above-mentioned experiments have shown that the expression level of SERCA is important for the survival of the nematode it is possible that this strategy may result only in the isolation of partial knock-out mutations as heterozygote C. elegans carrying a severe knock-out mutation in the SERCA gene may not viable. In this situation, strategy 1 based on extra-chromosomal expression can be used to isolate severe knock-out mutations.

Strategy 2

Although primary RNAi experiments indicate that the level of expression the SERCA protein needs to be fine-tuned for the survival of the C. elegans nematode, strains in which the level of SERCA activity is reduced, in particular strains in which SERCA activity is reduced in a single tissue, are probably still viable. Due to the sensitivity of C. elegans to the level of SERCA activity this could result in a recognisable phenotype, such as reduced pharyngeal pumping, vulva muscle defects, and hence egg laying defects, anal repressor and anal sphincter defects, and hence defecation defects, and body wall muscle defects, and hence movement defects. Such strains can be used as the basis of screens to identify compounds capable of enhancing or up-regulating the activity of SERCA.

The expression levels of SERCA in C. elegans can be specifically reduced by using antisense technology or double stranded RNA inhibition. The use of antisense technology to specifically reduce expression of a given protein is well known. For the expression of antisense RNA in the worm, the non-coding strand of a fragment of the SERCA gene can be expressed under the control of the SERCA, myo-2 or myo-3 promoter or any other promoter. The expression of the antisense SERCA RNA will result in the inhibition of expression of SERCA.

Antisense technology can be used to control gene expression through triple-helix formation of antisense DNA or RNA, both of which methods are based on binding of a polynucleotide to DNA or RNA. For example, the 5' coding portion or the mature protein sequence, which encodes for the SERCA protein, is used to design an antisense RNA oligonucleotide of from 10 to 50 base pairs in length. The antisense RNA oligonucleotide hybridises to the mRNA in vivo and blocks translation of an mRNA molecule into the protein (Okano, J. Neurochem., 56:560 (1991); Oligodeoxy-nucleotides as Antisense Inhibitors of Gene Expression, CRC Press, Boca Raton, Fla. (1988)). A DNA oligonucleotide is designed to be complementary to a region of the gene involved in transcription (triple-helix—see Lee et al. Nucl. Acids Res., 6:3073 (1979); Coney et al., Science, 241:456 (1988); and Dervan et al., Science, 251: 1360 (1991), thereby preventing transcription and the production of the protein.

In order to perform an antisense experiment in C. elegans, an EcoRI-Hind III fragment of SERCA exon 5 was cloned antisense under the control of the myo-2 promoter, the myo-3 promoter, the SERCA promoter or the ceh-24 enhancer and injected into C. elegans. These vectors result in the expression of an antisense SERCA RNA, and hence in inhibition of SERCA activity.

As an alternative to the antisense approach, the expression of a given gene in a cell can also be specifically reduced by introducing into the cell double stranded RNA corresponding to a region of the transcript transcribed from the gene. Double stranded RNA can be prepared by cloning an appropriate fragment into a plasmid vector containing opposable promoters. A suitable example is the pGEM7 series of vectors from Promega Corporation, Madison, Wis., USA, which contain opposable promoters separated by a multiple cloning site. When the plasmid vector is transformed or transfected into a host cell or organism which expresses the appropriate polymerases, RNA will be transcribed from each of the promoters. As the vector contains two promoters oriented in the opposite sense, complementary sense and antisense transcripts will be transcribed which will combine to form double stranded RNA. The injection of double stranded RNA in C. elegans has previously been described (Fire et al, Potent and Specific Genetic Interference by Double-Stranded RNA in C. elegans 1998, Nature 391 860–811).

EXAMPLE 7

Analysis of a C. elegans Mutant (Designated ok190)

A C. elegans strain mutated in the SERCA gene was kindly provided by R. Barstead (Oklahoma, USA). Heterozygous animals show no defect, but their homozygous progeny die as L1. The lethal phenotype can be rescued by reintroduction of the C. elegans gene by injection of pGK7.

Using standard PCR protocols the genomic region of ok190 around the deleted area was cloned in the following way:

A nested PCR was performed on C. elegans genodneic DNA using the following primer pairs:

Outer:
    SERCA P2: CGAAGAGCACGAAGATCAGACAG (SEQ ID NO:25)
    SERCA P8: GAGAGGCGGTTGGTTTGGG (SEQ ID NO:26)
Inner:
    SERCA P4: CCGTTCGTCATCCTTCTCATTC (SEQ ID NO:27)
    SERCA P7: CGACAGATGGACCGACGAGC (SEQ ID NO:28)

Analysis of the nested PCR product by agarose gel electrophoresis showed that the PCR product in the ok190 strain harbors a deletion of 1.7 kbp. (The wild-type PCR product from SERCA P4–SERCA P7 would be 3.4 kbp but the observed ok190 PCR product was only 1.7 kbp).

To enable detailed analysis of the deleted region the PCR product was cloned into the pCR-XL-TOPO vector (Invitrogen, The Netherlands). The resulting plasmid was designated pKO4. This cloned fragment was then sequenced reveal ing the exact coordinates of the deleted region. One of the breakpoints of the deletion occurred in the intron between exon IV and exon V, the other in exon V, deleting a total of 1702 bp of which 1690 bp represent coding sequence.

The nucleotide sequence of the genomic fragment of *C. elegans* SERCA bounded by primers SERCA P4 and SERCA P8 is shown in FIG. 4 and as SEQ ID NO: 16. Exon IV and exon V are shown in capitals, intron IV in lower case. The fragment deleted in ok190 is underlined.

EXAMPLE 8
Construction of a Thapsigargin Resistant SERCA

A mutated *C. elegans* SERCA gene which encodes mutant protein resistant to thapsigargin inhibition has been constructed. The mutation is TTC GTC, which results in a Phe258Val substitution. This is analogous to the substitution Phe256Val in hamsters, which was shown to be 40-fold resistant to thapsigargin inhibition (Yu et al., 1999, Arch. Biochem. Biophys. 15:225–232).

The mutation was introduced in the gene with the Quick-Change Site-Directed Mutagenesis Kit (Stratagene, California, USA). PCR was performed on pGK7, according to the instructions supplied by the manufacturer, with the following primers:

oGK33F256V
(CAACAGAAGTTGGACGAAGTCGGAGAGCAACT-TTC) (SEQ ID NO:29)
oGK34F256V
(GAAAGTTGCTCTCCGACTTCGTCCAACTTCTGT-TG) (SEQ ID NO:30)

The resulting mutation was screened by EcoRI digestion, as the mutation resulted in the disruption of the EcoRI restriction site. The new vector was sequenced, and the vector was transfected into *C. elegans*. The resulting vector was designated pGK28.

Test Sensitivity of Phe259Val SERCA Mutation

Several *C. elegans* transgenic lines where constructed that carry the thapsigargin resistant SERCA mutant by standard injection of pGK28 into the gonad.

The effect of thapsigargin on worms carrying a pGK28 transgene was measured in the following way: 10 μl of thapsigargin dissolved in DMSO (5, 2.5, 1, 0.5, 0.25, 0.1, and 0.05 mM respectively) was added onto a drop of *E. coli* strain OP50cs2 in 12-well plates. The wells with compounds were placed at 10 C. overnight, after which 1 to 10 young adults were added to the wells. The pharynx pumping rate and movement behaviour was scored for the ten worms after 10 minutes and after one hour (short term effect). Furthermore the wells were scored for protruding vulva and rectum, production of progeny (few eggs in body) after one day (mid-term-effects), and for progeny after four days (long term effect)

Cold-sensitive *E. coli* strain OP50cs2 was deposited on Mar. 25, 1999 in accordance with the provisions of the Budapest Treaty on the International Recognition of the Deposit of Microorganisms in the Belgian Coordinated Collections of Microorganisms (BCCM)/Laboratorium voor Microbiologie-Bacterienverzameling (LMG) bacteria collection, Universiteit Gent, K. L. Ledeganckstraat 35, B-9000, Gent, Belgium under accession number LMG P-18934.

Conclusions

The results from this experiment confirmed that the Phe259Val pGK28 lines tested are more resistant to thapsigargin. The clearest indication for resistance was that a large fraction of the GFP-animals (the animals harboring pGK28) grew up to adult or L4 while most non-GFP (not harboring or expressing the mutated SERCA) arrested at L1 and L2 and never grew up further than L3 (see FIG. 3). Furthermore it was observed that nematodes harboring the Phe259Val SERCA mutant had slightly more progeny than wild-type and that the protruding vulva and rectum-phenotype was very often observed in the wild-type nematodes treated with thapsigargin, whereas these phenotypes were not or were only occasionally observed in strain UG530 (strain harboring plasmid pGK28), treated with thapsigargin.

EXAMPLE 9
Construction of a *C. elegans* SERCA Mutant cDNA with a PLB Recognition Site Phospholamban is known to interact with the KDDKPV (SEQ ID NO:39) site in mammalian SERCA1 and SERCA2 (Toyofuku et al., J. Biol Chem. 1994, 269:22929–22932). SERCA3 does not contain this sequence and does not bind phospholamban. SERCA3 does bind phospholamban when the KDDKPV sequence (SEQ ID NO:39) is introduced, while SERCA2 can no longer bind phospholamban when this sequence is mutated (Toyofuku et al., J. Biol Chem. 1994, 269:22929–22932). Phospholamban also interacts with transmembrane helix TM6, which is identical in all three mammalian SERCA genes (Asahi et al., J. Biol. Chem. 1999, 274:32855–32862).

The *C. elegans* SERCA gene does not contain the KDDKPV sequence (SEQ ID NO:39), but the TM6 domain is identical to mammalian SERCA. A variant of *C. elegans* SERCA containing the KDDKPV (SEQ ID NO:39) recognition site was constructed using standard site directed mutagenesis technology (QuikChange Site-Directed Mutagenesis Kit of Stratagene). The primers oGK118 and oGK119 and plasmid pGK28 were used to obtain a plasmid designated pGK115 containing thapsigargin-resistant *C. elegans* SERCA with the KDDKPV (SEQ ID NO:39) site.

oGK118:GCCAGTCGGAAAGGTTTCCA<u>AGGA</u>CG
  ACAAGCCA<u>G</u>TTAACCCAGCTGCTGGAGAATT
  (SEQ ID NO:31)
oGK119:AATTCTCCAGCAGCTGGGTT<u>AA</u>C<u>T</u>
  GGCTTGTC<u>G</u>T<u>CCT</u>TGGAAACCTTTCCGACTGGC
  (SEQ ID NO:32)

(Nucleotides leading to the mutated SERCA are underlined.)

Plasmid pGK115 was introduced into *C. elegans* using standard techniques. Introduction of this mutant SERCA into *C. elegans* results in a more efficient interaction between the *C. elegans* SERCA (here the mutant) and vertebrate PLB. Introduction of a KDDKPV (SEQ ID NO:39) mutant into a *C. elegans* strain which is mutant for SERCA, such as the ok190 strain, results in a strain which is directly useful for performing screens to select for compounds that alter the interaction of SERCA with PLB and hence that alter the activity of SERCA. Since pGK115 also contains the thapsigargin resistance mutation, it can also be expressed in a wild-type *C. elegans* for use in screens to select for compounds that alter the interaction of SERCA with PLB and hence that alter the activity of SERCA. In such a screen, thapsigargin should be added to differentiate between activity of the endogeneous SERCA and the introduced double mutant SERCA.

EXAMPLE 10
Construction of Fusion Proteins Between *C. elegans* SERCA and Vertebrate SERCA The introduction of vertebrate SERCA in *C. elegans*, the latter being a SERCA mutant such as ok190 or a wild-type strain where the endogenous SERCA is inhibited for example by RNAi technology, will result in rescue of the mutant phenotypes, but maybe not to the full extent. This could be due, for example, to different kinetic properties of *C. elegans* and vertebrate SERCA, or to interaction with other partners than phospholamban. Using fusion proteins will overcome this problem. A fusion protein may be constructed that has sufficient properties of the *C. elegans*

SERCA for rescue of the mutant phenotype, and has those vertebrate SERCA properties sufficient in a screen to select for compounds that alter the vertebrate SERCA activity.

At least four types of fusion proteins are contemplated:

1) A fusion protein harboring the N-terminal end of the *C. elegans* and the C-terminal part of a vertebrate SERCA
2) A fusion protein harboring the N-terminal part of a vertebrate SERCA and the C-terminal part of the *C. elegans* SERCA
3) A fusion protein harboring the C- and N-terminal part of the *C. elegans* SERCA and an internal part of a vertebrate SERCA. This construction can be considered as a variant of the KDDKPV (SEQ ID NO:39) mutation described above.
4) A fusion protein harboring the C- and N-terminal part of a vertebrate SERCA and an internal part of the *C. elegans* SERCA Such fusion proteins can easily be constructed using standard molecular techniques.

A SERCA fusion protein of type 1 has been made in the following way:

A PCR reaction was performed on plasmid pGK110 (harboring the pig thapsigargin resistant SERCA2A) using primers oGK108 and oGK109.

oGK108: GACCGTACGAAATTTTCAGGAAAGGAAT-GCAGAAAATGCC (SEQ ID NO:33)

oGK109: CCCCGGCCGGCCTTACTCCAGTATTG-CAGGTTCCAGG (SEQ ID NO:34)

The resulting 2701 bp PCR fragment was digested with BsiWI and EagI and cloned in the 10131 bp fragment of pGK8 (containing genomic *C. elegans* SERCA) cut at the same sites. The resulting vector was designated pGK114.

EXAMPLE 11
Construction of Phospholamban Mutants that Show Altered Interaction with SERCA The interaction of phospholamban with SERCA has been described very extensively in the literature. Furthermore mutants of PLB have been described that have an enhanced or a diminished interaction with SERCA and hence have a stronger or weaker inhibitory effect on SERCA (Toyofuku et al., J. Biol. Chem 1993, 269:3088–3094; Kimura et al., J. Biol. Chem. 1996, 271:21726–21731; Kimura et al., J. Biol. Chem. 1997, 272:15061–15064; Kimura et al., J. Biol. Chem. 1998, 273:14238–14241).

Introduction of a PLB mutant with an altered inhibition of SERCA in *C. elegans* can improve the basic screen to select for compounds that alter the interaction of PLB and SERCA in such a way that the parameters of the screen can be fine-tuned exactly as is most useful, allowing screening for more specific compounds directed to the PLB SERCA interaction.

PLB mutations can easily be made using standard site directed mutagenesis techniques as described above, and as known in the art.

One phospholamban mutant of particular interest is Ser16Ala. In intact beating hearts or isolated cardiac myocytes, serine16 becomes phosphorylated by cAMP-dependent protein kinase upon stimulation with isoproterenol. This leads to increased cardiac relaxation due to decreased inhibition. A phospholamban mutant for this phosphorylation site thus lacks cAMP-dependent protein kinase-mediated regulation (Simmerman et al., J. Biol. Chem. 1986,261:13333–13341; Wegener et al., J. Biol. Chem. 1989, 264:11468–11474; Kuschel et al., Am. J. Physiol. 1999, 276:H1625-H1633).

EXAMPLE 12
Cloning of Pig PLB, Construction of Humanized Pig PLB

Pig PLB cDNA was cloned from pGEM7PigPLB (Wuytack, personal gift) by PCR amplification using the primer combinations listed below. PCR amplification was performed using standard procedures (PCR, A practical approach, ed. by M. J. McPherson, P. Quirke and G. R. Taylor, 1993, Oxford University Press.

Summary of Primer Combinations oGK51-oGK55: pg PLB, including stop codon
oGK51-oGK56: pig PLB, excluding stop codon (open ended)
oGK52-oGK55: humanized pig PLB, including stop codon
oGK52-oGK56: humanized pig PLB, excluding stop codon (open ended)

oGK51 and oGK52 contain an XbaI site for cloning
oGK55 and oGK56 contain an Asp718 site for cloning oGK52 contains T-to-G point mutation compared to pig PLB cDNA so as to introduce a D-to-E amino acid substitution at position 2 of PLB. Since this is the only difference between the human and pg PLB proteins, the resultant polypeptide is the same as the human PLB sequence (NB the point mutated cDNA does not have the same sequence as the human PLB cDNA but encodes a protein having identical amino acid sequence to human PLB, hence it is referred to as a humanized pig PLB cDNA).

Sequences of the Primers are as Follows oGK51: GCTCTAGATGGATAAAGTCCAATACCTCAC (SEQ ID NO:35)
oGK52: GCTCTAGATGGAGAAAGTCCAATACCTCAC (SEQ ID NO:36)
oGK55: GGGGTACCTCAGAGAAGCATCACGATGATG (SEQ ID NO:37)
oGK56: GGGGTACCATGAGAAGCATCACGATGAT-GCAAATC (SEQ ID NO:38)

pGK202 was constructed by cloning the oGK51-oGK55 PCR fragment digested with XbaI and Asp718 into pPd96.48 digested with the same enzymes. The vector expresses pig PLB under the control of the myo-2 promoter.

pGK204 was constructed by cloning the oGK51-oGK56 PCR fragment digested with XbaI and Asp718 into pGK203 digested with the same enzymes. The vector expresses the pig PLB fused to GFP under the control of the myo-2 promoter.

pGK205 was constructed by cloning the oGK52-oGK55 PCR fragment digested with XbaI and Asp718 into pPD96.48 digested with the same enzymes. The vector expresses the humanized pig PLB under the control of the myo-2 promoter.

pGK206 was constructed by cloning the oGK52-oGK56 PCR fragment digested with XbaI and Asp718 into pGK203 digested with the same enzymes. The vector expresses the humanized pig PLB fused to GFP under the control of the myo-2 promoter.

pGK302 was constructed by cloning the oGK51-oGK55 PCR fragment digested with XbaI and Asp718 into pPD96.52 digested with the same enzymes. The vector expresses the pig PLB under the control of the myo-3 promoter.

pGK304 was constructed by cloning the oGK51-oGK56 PCR fragment digested with XbaI and Asp718 into pGK303 digested with NheI-Asp718. The vector expresses the pig PLB fused to GFP under the control of the myo-3 promoter.

pGK305 was constructed by cloning the oGK52-oGK55 PCR fragment digested with XbaI and Asp718 intointo pPD96.52 digested with NheI-Asp718. The vector expresses the humanized pig PLB under the control of the myo-3 promoter.

pGK306 was constructed by cloning the oGK52-oGK56 PCR fragment digested with XbaI and Asp718 into pGK303 digested with NheI-Asp718. The resulting vector expresses the humanized pig PLB fused to GFP under the regulation of the myo-3 promoter.

EXAMPLE 13

Inhibition of SERCA by Compounds

Several compounds are known to inhibit the function of SERCA, such as cyclopiazonic acid, cyproheptadine, thapsigargin, 2,5-di (tert-butyl)-1,4-benzohydroquinone, 2,4-benzoquinone, and vanadate. Other compounds are known to activate the activity of SERCA, such as diethylether, gingerol, and 1-(3,4-dimethoxyphenyl)-3-dodecanone. Still other compounds have a dual activity, they stimulate SERCA at low concentrations, but inhibit at high concentrations, such as phenothiazines, and pentobarbital.

Using two kinds of assays, the optimal concentration of compounds that inhibit the activity SERCA has been determined. The first assay is designated the drop or plate assay in which the nematodes are fed $E.$ $coli$ strains pre-loaded with the compound. In a second assay, the compound is administrated to the worm in liquid culture.

Plate Assay

A standard plate drop assay is performed according to the following protocol. 4 ml NGM agar (see "The nematode $C.$ $elegans$" Ed. by William B. Wood and the Community of $C.$ $elegans$ Researchers, CSHL Press, 1988, pg589) is into 3 cm plates and seeded with approximately 5 $\mu$l of an $E.$ $coli$ overnight culture and grown preferably for one week at room temperature. Approximately 10 $\mu$l of test compound dissolved in DMSO or other suitable solvent is pipetted onto the bacterial lawn so that the lawn is covered completely. After overnight soaking in or compound, one $C.$ $elegans$ (L4 stage) per plate is put onto the bacterial lawn. Plates are incubated at 21° C. and checked after some hours. Plates are checked again after 4 days for phenotypes of the F1 progeny (control shows all stages up to gravid hermaphrodites).

Thapsigargin at various concentrations (5 $\mu$M, 2.5 $\mu$M and 1.25 $\mu$M) causes the nematode to stop pharynx pumping within 10 min. Within an hour the worms restart pumping, although at a low level. The worms are pale and thin and have a slow and irregular movement, with an increased amplitude. No plate drop response is observed, and the worms show poor backing, reduced pumping and strong constipation. The worms have a defective gonad with only very few eggs, and a protruding vulva. Some worms also have a protruding rectum. Progeny reaches L2 stage only after four days, and the brood size is very small. Lower concentrations of thapsigargin (0.5 $\mu$M, 0.25 $\mu$M, 0.125 $\mu$M) still cause reduced brood size.

2,5-di-tert butylhydroquinone at a concentration of 500 $\mu$M resulted in pale, starved, thin worms with slow movement, defective gonad, constipated and reduced brood size.

Cyclopiazonic acid at a concentration of 500 $\mu$M resulted in nematodes that lay still or move slowly after one hour. The worms showed strong avoidance and after 24 hours they look starved, pale and thin, with only a few eggs in the body, a defective gonad, and reduced brood size. A delayed growth of the F1 generation was observed.

Thapsigargicin at 500 $\mu$M, 125 $\mu$M, 31 $\mu$M, 10 $\mu$M, 5 $\mu$M resulted in nematodes with similar phenotypes to those described above for thapsigargin at 5 $\mu$M, 2.5 $\mu$M, 1.25 $\mu$M. Lower concentrations of thapsigargicin (3 $\mu$M and 1.5 $\mu$M) caused a slightly reduced brood size.

Thapsigargin-epoxide did not result in a clear observable effect, even at the highest concentration tested (1 mM drop, 5 $\mu$M end concentration).

1,4-benzoquinone did not result in a clear observable effect, even at the highest concentration tested (100 mM drop, 500 $\mu$M end concentration).

Liquid

Thapsigargin at 100, 50 and 20 $\mu$M resulted in small worms which show slow and loopy movement. They had a protruding vulva, and no progeny (or no progeny that grows up) were observed. At lower concentrations of 10 $\mu$M and 5 $\mu$M a reduced number of progeny and delayed growth could be observed.

2,5-di-tert butylhydroquinone at a concentration of 1 mM resulted in progeny exhibiting delayed growth and the worms be observed to be thinner than 'normal' worms.

Cyclopiazonic acid at a concentration of 1 mM resulted in pale, thin worms with a slow movement and a very strongly reduced brood size. At lower concentrations of 0.5 mM, growth delay was observed.

Thapsigargicin at 1000 $\mu$M, 250 $\mu$M, 62.5 $\mu$M and 16 $\mu$M concentrations resulted in small worms with slow and loopy movement, a protruding vulva, and no progeny (or no progeny that grows up) were observed. At lower concentrations of 10 $\mu$M, delayed growth and reduced progeny were observed.

Figure 1:
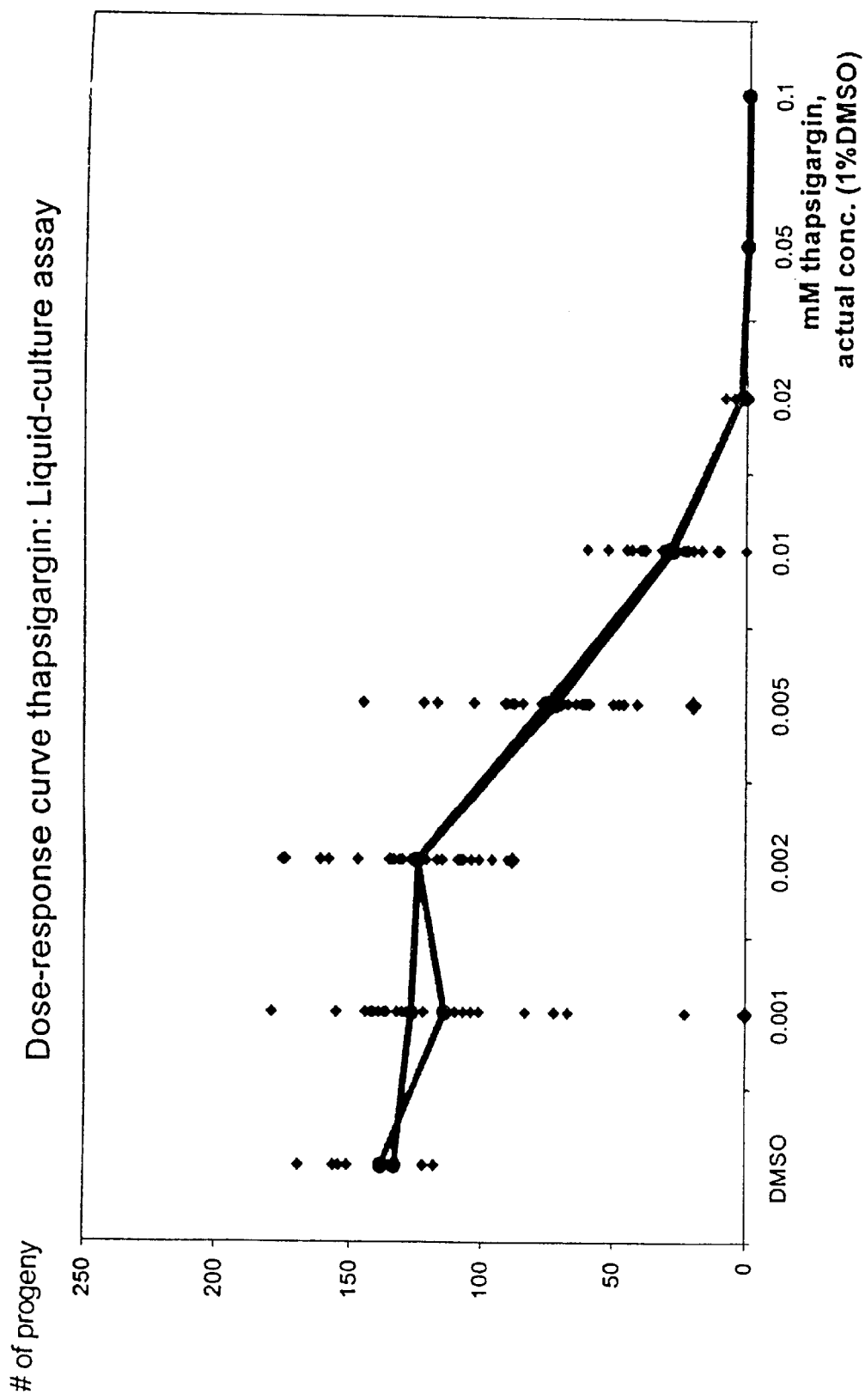
FIG. 1 shows a dose-response curve for thapsigargin produced using a liquid culture assay.

The effect of thapsigargin on progeny of wild-type strains was tested with the liquid assay: On an average of 12 worms, the number of progeny for the different concentrations is summarized in FIG. 1.

Figure 2:
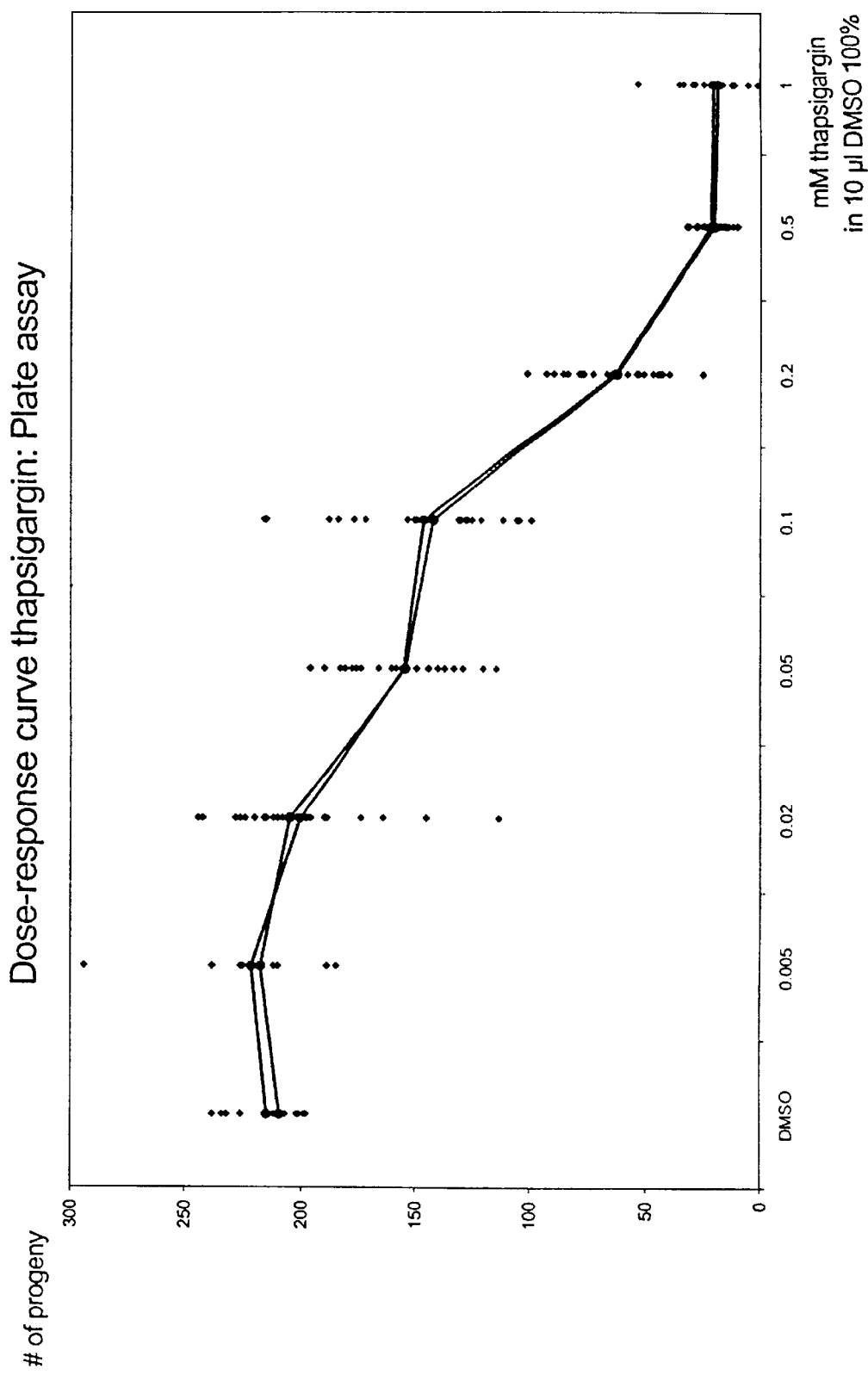
FIG. 2 shows a dose-response curve for thapsigargin produced using a plate assay.

The effect of thapsigargin was also tested on progeny of wild-type strains using the plate assay: On an average of 12 worms the number of progeny at different concentrations is summarized in FIG. 2.

The effect of thapsigargin on the production of progeny was determined for a number of different $C.$ $elegans$ strains. The numbers of progeny produced following thapsigargin treatment was counted for an average of 15 animals, the results are summarised as follows:

unc-31:
  control: 132
  0.5 mM: 35
  1 mM: 5,6
srf-3:
  control: 50
  1 mM: 18,3

The effect of thapsigargin on pharynx pumping behaviour was also determined. In wild-type worms, all animals stopped pumping after 10 minutes. In mutant strain unc-31 at a concentration of 1 mM thapsigargin, all worms stopped pumping after 10 minutes, some start again after half an hour, but pumping is only one third of normal speed.

In summary, the above experiments demonstrate that inhibition of $C.$ $elegans$ SERCA activity using thapsigargin or other chemical inhibitors of SERCA results in worms with recognisable phenotypic characteristics, including paleness, reduced growth, reduced rate of pharynx pumping and reduced numbers of progeny.

EXAMPLE 14

Screening for Antagonists of a Compound (Thapsigargin)

The compound thapsigargin is known to inhibit the activity of SERCA. The SERCA protein pumps calcium into the sarco/endoplasmic reticulum and provides the cell with an internal storage of calcium. The internal storage of calcium is important for muscle activity. In $C.$ $elegans,$ inhibiting SERCA activity by applying thapsigargin to the worm results in a decrease in the pharynx pumping rate. Another feature observed by the action of thapsigargin on the nematode worm $C.$ $elegans$ is decreased movement, which is a result of the inhibition of SERCA activity of the body wall muscles.

A pharynx pumping screen has been developed to screen for chemical substances that suppress the activity of thapsigargin on SERCA. In this screen the pumping rate of the pharynx is measured indirectly by adding a marker molecule precursor such as calcein-AM to the medium and measuring the formation of marker dye in the C. elegans gut. Calcein-AM is cleaved by esterases present in the C. elegans gut to release calcein, which is a fluorescent molecule. The pumping rate of the pharynx will determine how much medium will enter the gut of the worm, and hence how much calcein-AM will enter the gut of the worm. Therefore by measuring the accumulation of calcein in the nematode gut, detectable by fluorescence, it is possible to determine the pumping rate of the pharynx.

A standard pharynx pumping screen may be carried out as follows.

1) Dispense substantially equal numbers of C. elegans nematodes into the wells of multi-well assay plates. A 'worm dispenser' apparatus, e.g. the device commercially available from Union Biometrica, Inc, Somerville, Mass., USA which has properties analogous to flow cytometers, such as fluorescence activated cell scanning and sorting devices (FACS), may be used for this purpose. Typically, 40+/−5 worms are added to each well of the microtiter plate.

2) Thapsigargin is added to the worms at an inhibitory concentration and calcein-AM is added at a concentration of 5–10 M.

3) The chemical substances to be selected are added. Control wells are also set up containing thapsigargin alone with no second chemical substance. The chemical substances are typically made up in DMSO. Any other solvent can be used for this purpose, but most selected chemical substances appear to be soluble in DMSO. The chemical substance is added in the wells at various concentrations. but preferentially a concentration between 3 to 30 $\mu M$ is chosen as this gives the clearest results. It possible to screen for dosage effects by varying the concentration of the chemical substance from less than 1 $\mu M$ up to 100 $\mu M$.

The concentration of the DMSO should not be too high and preferentially should not exceed 1%, more preferentially the concentration of the DMSO should not exceed 0.5% and even more preferentially, the concentration of the DMSO is lower than 0.3%.

4) Fluorescence intensity is measured using a multi-well plate reader (e.g. Victor2, Wallac Oy, Finland) with following settings: Ex/Em=485/530.

Wells harboring a chemical substance where the measured fluorescence is higher than in the control wells containing no chemical substance are scored. These wells harbor a chemical substance that is an antagonist of the thapsigargin activity, as the inhibitory activity of thapsigargin is suppressed. Chemical substances thus identified may inhibit directly the activity of thapsigargin, or stimulate the activity of SERCA, or have an enhancer activity on the SERCA pathway, and hence on the calcium biology of the organism.

Chemical substances selected in this screen as antagonists of thapsigargin are considered as potential therapeutics, or as hits for the further development of therapeutics in the disease areas which are the cause of a malfunction of the calcium biology of the organism. Examples of disease areas for which these therapeutics are useful are cardiac hypertrophy, cardiac failure, arterial hypertension, Type 2 diabetes and Brody disease.

In the example given above, thapsigargin is used as an example of a compound having a defined phenotypic effect on C. elegans as a result of inhibition of SERCA activity. It will be appreciated that other SERCA inhibitors which have an inhibitory activity on the pharynx pumping rate may be used in analogous screens with equivalent effect.

EXAMPLE 15

Screening for Chemical Substances in Transgenic, Mutant and Humanized Animals (SERCA-PLB)

An increase of the internal storage of calcium is general considered to be important for the strength of muscle contraction, and consequently an improvement or increase of this muscle contraction can be realized by enhancing SERCA activity. Chemical substances that enhance SERCA activity or inhibit the SERCA-PLB interaction are considered as potential therapeutics, or as hits for the further development of therapeutics in the disease areas which are the cause of a malfunction of the calcium biology of the cell or organism. Examples of disease areas where an increase of SERCA activity may be beneficial are cardiac hypertrophy, cardiac failure, arterial hypertension, Type 2 diabetes and Brody disease.

The different SERCA genes and isoforms which are associated with different types of diseases; SERCA2 and PLB are associated with cardiovascular diseases, SERCA1 and sarcolipin are associated with skeletal-muscle diseases, and three SERCA genes have been associated with non-insulin-dependent diabetes mellitus.

In order to perform screens to identify chemical substances which modulate the activity of SERCA pathways SERCA genes and PLB have been expressed in C. elegans. The expression of these genes can be regulated under the control of several specific promoters with the following activities:

a) The C. elegans myo-2 promoter which promotes expression in the pharynx b) The C. elegans SERCA promoter which promotes expression in the C. elegans muscles, including the pharynx, the vulva muscles and the body wall muscles.

The following transgenics were constructed:

a) pig and/or human SERCA under the SERCA and/or myo-2 promoter.

b) pig and/or human SERCA under the SERCA and/or myo-2 promoter in a C. elegans mutated for the C. elegans SERCA (Knock-outs and selected mutants).

c) pig and/or human PLB under the SERCA and/or the myo-2 promoter.

d) pig and/or human PLB under the SERCA and/or the myo-2 promoter in a C. elegans mutated for the C. elegans SERCA (Knock-out and selected mutants).

e) pig and/or human PLB-GFP fusion under the SERCA and/or the myo-2 promoter.

f) pig and/or human PLB-GFP fusion under the SERCA and/or the myo-2 promoter in a C. elegans mutated for the C. elegans SERCA (Knock-outs and selected mutants).

g) pig and/or human SERCA under the SERCA promoter and pig and/or human PLB under the myo-2 promoter.

h) pig and/or human SERCA under the SERCA promoter and pig and/or human PLB under the myo-2 promoter in a C. elegans mutated for the C. elegans, SERCA (Knock-out and selected mutants).

i) pig and/or human SERCA under the SERCA promoter and pig and/or human PLB-GFP under the myo-2 promoter.

j) pig and/or human SERCA under the SERCA promoter and pig and/or human PLB-GFP under the myo-2 promoter in a C. elegans mutated for the C. elegans SERCA (Knock-out and selected mutants).

Some of these constructed transgenic and mutant worms show a clear change in pharynx pumping rate as can be measured by the fluorescence of calcein in the gut using the calcein-AM pharynx pumping assay. Some of these strains were considered to be useful for further screen development. To perform the pharynx pumping assay, the transgenic and mutant animals were placed in the wells of multi-well plates. Calcein-AM and chemical substances under test were then added. The fluorescence of the calcein formed in the gut was measured in a multi-well plate reader set to measure fluorescence. Chemical substances that altered the properties of the pharynx pumping rate, and hence altered the function and activity of the SERCA pathway were selected for further analysis, and can be considered as potential compounds for therapeutic use, or as hits for the further development of therapeutics.

A analogous experiment can be performed with the SERCA1 gene and its regulator Sarcolipin (SLN), to detect chemical substances that alter their activity and/or regulation.

EXAMPLE 16
Construction of Plasmids

The 'pPD' series of vectors were all obtained from the laboratory of Andrew Fire, see Fire A, Harrison S. W., and Dixon D. A modular set of LacZ fusion vectors for studying gene expression in *Caenorhabditis elegans*. 1990. Gene 93:189–198. The sequences of these vectors are freely available at ftp://stein.cshl.org/pub/elegans_vector/).

pGK301 was constructed by cloning a 3181 bp fragment of pERIIIA (F. Wuytack, personal communication) into pPD96.52 digested with the same restriction enzymes. pGK301 expresses the SERCA2a cDNA under the regulation of the myo-3 promoter.

pGK201 was constructed by cloning a 480009 bp NheI/SpeI fragment of pGK301 in pPD96.48 digested with the same enzymes. The vector expresses pig SERCA2a under the regulation of the moy-2 promoter.

pGK101 was constructed by cloning a 4828 bp NheI/ApaI fragment of pGK201 into plasmid pDW2600 digested with the same enzymes. The vector expresses the pig SERCA2a cDNA under the regulation of the worm SERCA promoter.

pDW2600 was constructed by cloning a 5046 bp SphI-SmaI fragment of pGK10 in pPD49.26.

pGK203 was constructed by cloning the AccI/SpeI fragment of pPD95.79 into pPD96.48 digested with the same enzymes. This vector contains the myo-2 promoter, GFP and unc-54 3'UTR.

pGK303 was constructed by cloning the Asp718-ApaI fragment of pPD95.79 into pPD96.52 digested with the same enzymes. This vector contains the myo-2 promoter, GFP and unc-54 3'UTR.

List of Genbank Accession Numbers for SERCA and PLB cDNA Sequences
pig SERCA2a GenBank P11606
human SERCA1a GenBank AAB 53113
human SERCA1b GenBank AAB 53112
human SERCA2a GenBank P16614
human SERCA2b GenBank P16615
human SERCA3 GenBank Q93084
pig PLB GenBank P07473
human PLB GenBank P26678

Sequence Listing

SEQ ID NO:1 is the nucleic acid sequence of a 732 bp EcoRI-HindII fragment of *C. elegans* SERCA exon 5. This fragment was cloned into pGEM3 for use in RNA inhibition experiments.

SEQ ID NO:2 is the nucleic acid sequence of a 11207 bp SpeI-MluI fragment of cosmid K11D9. This fragment contains the complete *C. elegans* SERCA gene with 5631 bp of upstream sequence, the entire coding region and 1088 bp of downstream sequence. The fragment was cloned into pUC18 to give plasmid pGK7.

SEQ ID NO:3 is the nucleic acid sequence of a 5026 bp fragment of the upstream region of *C. elegans* SERCA, up to and including A of the initiating ATG. This fragment was cloned into pPD95.79, in fusion with GFP, to give plasmid pGK10.

SEQ ID NO:4 is the nucleic acid sequence of a 2915 bp fragment of the upstream region of *C. elegans* SERCA, as found in plasmid pGK13.

SEQ ID NO:5 is the nucleic acid sequence of a 6612 bp fragment of the *C. elegans* SERCA gene containing 5637 bp of upstream sequence and ending in exon 4, as cloned in pPD95.75, resulting in pGK12.

SEQ ID NO:6 is the nucleic acid sequence of the long isoform of the *C. elegans* SERCA cDNA.

SEQ ID NO:7 is the nucleic acid sequence of the pig SERCA2a cDNA.

SEQ ID NO:8 is the nucleic acid sequence of the human SERCA2a cDNA.

SEQ ID NO:9 is the nucleic acid sequence of the pig phospholamban cDNA.

SEQ ID NO:10 is the nucleic acid sequence of the *C. elegans* myo-2 promoter.

SEQ ID NO:11 is the nucleic acid sequence of the *C. elegans* myo-3 promoter.

SEQ ID NO:12 is the nucleic acid sequence of the *C. elegans* vulval muscle enhancer. This is an enhancer element from ceh-24 that directs gene expression in the vulval muscles (Harfe and Fire, 1998, Developmental 125: 421–429)

SEQ ID NO:13 is the nucleic acid sequence of humanized pig PLB cDNA.

SEQ ID NO:14 is the amino acid sequence of pig PLB.

SEQ ID NO:15 is the amino acid sequence of human PLB and humanized pig PLB.

SEQ ID NO:16 is the nucleotide sequence of a genomic fragment of *C. elegans* SERCA covered by primers SERCA P4 and SERCA P8.

SEQ ID Nos: 17–38 are primers used in the accompanying Examples.

SEQ ID NO:39 is an amino acid sequence insertion of a mutant *C. elegans* SERCA ATPase All references disclosed herein are incorporated by reference in their entirety.

---

What is claimed is:

1. A method of identifying compounds which enhance or up-regulate the activity of a sarco/endoplasmic reticulum calcium ATPase, which method comprises:
   contacting C. elegans which exhibit reduced SERCA ATPase activity compared to wild type C. elegans in one or more cell types or tissues with a compound under test; and
   detecting a phenotypic, biochemical or behavioural change in the C. elegans indicating a reversion towards wild type SERCA activity in the one or more cell types or tissues which exhibit reduced SERCA activity in the absence of the compound.

2. A method as claimed in claim 1 wherein the C. elegans have been treated with a SERCA inhibitor to reduce the activity of SERCA in one or more cell types or tissues prior to contact with the compound under test.

3. A method as claimed in claim 2 wherein the SERCA inhibitor is thapsigargin.

4. A method as claimed in claim 1 wherein the C. elegans have been treated with antisense or double-stranded RNA to specifically reduce the expression of SERCA in one or more cell types or tissues prior to contact with the compound under test.

5. A method as claimed in claim 1 wherein the C. elegans is a mutant C. elegans which exhibits reduced SERCA calcium ATPase activity in one or more cell types or tissues.

6. A method as claimed in claim 5 wherein the C. elegans is a mutant C. elegans which exhibits reduced expression of SERCA in one or more cell types or tissues.

7. A method as claimed in any one of claims 1 to 6 wherein the C. elegans exhibit reduced SERCA activity in the muscles of the pharynx, as compared to wild type C. elegans and the step of detecting a phenotypic, biochemical or behavioural change in the C. elegans indicating a reversion towards wild type SERCA activity comprises detecting a change in the pharynx pumping efficiency of the C. elegans in the presence of the compound under test.

8. A method as claimed in claim 7 wherein the C. elegans further contain a transgene comprising a promoter which directs gene expression in the muscles of the C. elegans pharynx operatively linked to nucleic acid encoding an apoaequorin protein.

9. A method as claimed in claim 8 wherein the promoter is the C. elegans myo-2 promoter or the C. elegans SERCA promoter.

10. A method as claimed in claim 8 wherein the step of detecting a phenotypic, biochemical or behavioural change in the C. elegans indicating a reversion towards wild type SERCA activity comprises comparing the level of apoaequorin luminescence in the absence of the compound under test and the level of apoaequorin luminescence in the presence of the compound under test.

11. A method as claimed in any one of claims 1 to 6 wherein the C. elegans exhibit reduced SERCA activity in the muscles of the vulva, as compared to wild type C. elegans.

12. A method as claimed in claim 11 wherein the step of detecting a phenotypic, biochemical or behavioural change indicating a reversion towards wild type SERCA activity comprises detecting a change in the egg laying behaviour of the C. elegans in the presence of the compound under test.

13. A method as claimed in claim 11 wherein the step of detecting a phenotypic, biochemical or behavioural change in the C. elegans indicating a reversion towards wild type SERCA activity comprises detecting a change in the amount of progeny produced by the C. elegans.

14. A method as claimed in claim 11 wherein the C. elegans further contain a transgene comprising a promoter which directs gene expression in the muscles of the C. elegans vulva operatively linked to nucleic acid encoding an apoaequorin protein.

15. A method as claimed in claim 14 wherein the step of detecting a phenotypic, biochemical or behavioural change in the C. elegans indicating a reversion towards wild type SERCA activity comprises comparing the level of apoaequorin luminescence in the absence of the compound under test and the level of apoaequorin luminescence in the presence of the compound under test.

16. A method as claimed in any one of claims 1 to 6 wherein the C. elegans exhibit reduced SERCA activity in the anal repressor and/or the anal sphincter and the step of detecting a phenotypic, biochemical or behavioural change in the C. elegans indicating a reversion towards wild type SERCA activity comprises detecting a change in the defecation behaviour of the C. elegans in the presence of the compound under test.

17. A method as claimed in any one of claims 1 to 6 wherein the step of detecting a phenotypic, biochemical or behavioural change in the C. elegans indicating a reversion towards wild type SERCA activity comprises comparing the growth rate of the C. elegans in the absence of the compound under test and the growth rate of the C. elegans in the presence of the compound under test.

18. A method as claimed in any one of claims 1 to 6 wherein the step of detecting a phenotypic, biochemical or behavioural change in the C. elegans indicating a reversion towards wild type SERCA activity comprises comparing the turbidity of the C. elegans in culture in the absence of the compound under test and the turbidity of the C. elegans in culture in the presence of the compound under test.

19. A method as claimed in any one of claims 1 to 6 wherein the step of detecting a phenotypic, biochemical or behavioural change in the C. elegans indicating a reversion towards wild type SERCA activity comprises detecting a change in the movement behaviour of the C. elegans.

* * * * *

SEQUENCE LISTING

<160> NUMBER OF SEQ ID NOS: 39

<210> SEQ ID NO 1
<211> LENGTH: 732
<212> TYPE: DNA

-continued

<210> ORGANISM: Caenorhabditis elegans

<400> SEQUENCE: 1

| gaattcgaat cactcaccga gttggccatg atctgcgcta tgtgcaatga ttcatctgtt | 60 |
|---|---|
| gattacaatg agaccaagaa gatctacgag aaagtcggag aagccactga aactgctctt | 120 |
| atcgttcttg ctgagaagat gaatgttttc ggaacctcga aagccggact ttcaccaaag | 180 |
| gagctcggag gagtttgcaa ccgtgtcatc aacaaaaat ggaagaagga gttcacactc | 240 |
| gagttctccc gtgatcgtaa atccatgtcc gcctactgct cccagcttc cggaggatct | 300 |
| ggagccaaga tgttcgtgaa gggagcccca gaaggagttc tcggaagatg cacccacgtc | 360 |
| agagttaacg gacaaaaggt tccactcacc tctgccatga ctcagaagat tgttgaccaa | 420 |
| tgcgtgcaat acggaaccgg aagagatacc cttcgttgtc ttgccctcgg aaccatcgat | 480 |
| accccagtca gcgttagcaa catgaacctc gaagactcta cccaattcgt caaatacgaa | 540 |
| caagacatca catttgtcgg agtcgtcgga atgcttgacc ccccaagaac tgaagtttcg | 600 |
| gactcgatca aggcttgtaa ccacgctgga atccgtgtca tcatgatcac cggagacaac | 660 |
| aagaacaccg ctgaggctat cggaagaaga atcggactct cggagagaa cgaggatacc | 720 |
| actggaaagc tt | 732 |

<210> SEQ ID NO 2
<211> LENGTH: 11207
<212> TYPE: DNA
<213> ORGANISM: Caenorhabditis elegans

<400> SEQUENCE: 2

| ctagttttga atccaaaaa aaaacaaag ttcaataaaa tgttacccaa ttgtgcgatt | 60 |
|---|---|
| tttgctttaa aaatacggta cccggtctcg atgcggcaat tgtttggtaa atgtaaaagg | 120 |
| gtgtgcgcct ttaaagagta ctgtaatttc aatcttccga cactgctgaa ttttttattga | 180 |
| cttttttgttc attaatttta tatatgattt attggtatgt taaaaaaaca cccatttttca | 240 |
| aatctattaa aattccacaa caacaaaagt tcgagattac agtacttttt agaggcgcac | 300 |
| atcctttttg ggatactaaa caattgtcgc gtcgagacca ggtaccatat ttccaaaaca | 360 |
| caatttcgcg tgtaaataaa aaatatcaac ataataattt ccatttttcg aaatttaaag | 420 |
| ttaatcactt tttggtttag attatgattt cacacgtttt tttccttcta gttctctttt | 480 |
| ttttgttatt tgcctgaaaa atggtctgaa aacttaggca atcagcaatg tgtcacataa | 540 |
| tttctcccag agaaatccct ttcaacaaaa tctcccggat tgacctgtgt gctcgacctt | 600 |
| gataaattgg ttggcagctc tctggcttat cttttgagag gaaaaagatc caacaaattt | 660 |
| ttatctccct tatccttttt tctcttcatc actaccaata ataatagttt ttttttttcgt | 720 |
| cgcggaagca aaatggcgaa caagtgttgg aataagagta ctccagggat ttaagggctg | 780 |
| aaagccagtg atttatgagc tccaattttt cagatgtttt ttcctccatc gcgtatttgt | 840 |
| ctaaacattc gattttcttc ctgcttccca acttttcaaa tcgaaataaa agagcatctg | 900 |
| tcgcttttta tcgatgtgct tctgtgagac taaagaacta ctcgttttca ctcgttctct | 960 |
| ctctctcaac tatcaaagtt ttgttgattg cgtgtgtcag cttccttctt tttattatca | 1020 |
| tcttttcatt ggaggaaaaa aataacttct gaagagcaaa agaactaact tcggggaata | 1080 |
| cagagaaaat tcctgtaaaa atctggaaat ttttttcgctt aactcgaaat atttagtttt | 1140 |
| tcactgtgat ttctgggaaa aatcaagaaa tatttgccta aaacacgagt tttcacatga | 1200 |
| aaatgaattt atttattgat ttttttatgga gattacaaaa aagacacacg tgaaactact | 1260 |

```
gctaccgtag ttgtgtaaac gtagtgttct ctatttagga cctgtttaat gtatttttt   1320
gcagttgaaa attttaaaa atatttagt tattttaaa aatatttaat ttacaaaata    1380
attagcctga acccatgaaa agatacgtta tatttaattt ttaccgtaag actttcaaga  1440
tcgttgcgag acccggcgcc taggtcaaag agcctccctt taaacccatc aacacgtttt  1500
gcctttttca tcgatttttt gcagttcttt tcttcttttcc aactgatttt tcttcatttt 1560
taaagttttt ttcctcattt ttcccatttg aaattattta aacacgtgca accagctggt  1620
aacatgtgtc acatgccgtt atctaacttc aaaacagtac atttccgatc acacgtcccc  1680
cgcgccgagt tttatagttt cattaataac ttttcggttt tgataatac taattgagtt   1740
ttattaattg tttccatatt catctagcac tttgacctgt ccttcttcga attctcaaat  1800
atttgcactc tgggtttagg tgtgaaaaga attgtcgtca ttaagcgggg catccggggc  1860
accgaaaaaa gccctccgat tttaacgaat ttgagataaa gttggagaga gagcccagtg  1920
tttgcttgcc caagatatat atcttggatt tatcaattac tgtttgtcaa cctgtcgccg  1980
gcgccccctt tttgctcttg ctcccacgcc ccgagattga atttcaattt tatttcgaag  2040
taagtctctt gattgtttcg aaaatccgat gacagttttc attactttt tgtctgttga   2100
ttttgtaggg aaacattgaa attttctga tctttctttg atcttatgat ttttcattta   2160
ttccaattaa aaaaattag cgcattcaga accagagtga agcttgagat gttgtaggtt   2220
tatcaaaaga tcaaatctc gaattccttc gaaatgtttt tagttttcga cttccgtgtg   2280
atttctagcg atcctgacag agatcactga attttaatgt tatcgagatt gttgtgtagg  2340
ctccatctcc tctctgaagc ttctgatttt gccgaaagtc tagttacttg ccgactgctg  2400
acactaggat atcccactac cgtacccatt gttggatccg tactctgctg cgacttcttc  2460
tctgtttcac gtgaacctcc gggatcgtcg gtaagcccccg cccgttatct gtgccaactt  2520
gtcttcgtgc cctcgagcga cgagctcatt caatcacgcc acgacctccg tctggacaga  2580
tgctctcatt gtctctgcgt ctccaagtat tcgtcacact atctcatgca ttctattcaa   2640
aacgcgagag aaagcgcggg aacgagagag agttcagaca gatcgaactt gttttatcc   2700
cccccccct cgtccggctg cagagcaaaa aaatactgct tttccttgca aaattcggtg   2760
ctttcttcaa agagaaactt tgaagtcgg cgcgagcatt tccttctttg acttctctct   2820
ttccgccaaa aagcctagca tttttattga taatttgatt acacacactc agagttcttc   2880
gacatgataa agtgtttcat tggcactcgc cctaacagta catgacaagg gcggattatt   2940
atcgatcgat attgaagaca aactccaaat gtgtgctcat tttggagccc cgtgtggggc   3000
agctgctctc aatatattac tagggagacg aggaggggga ccttatcgaa cgtcgcatga   3060
gccattcttt cttctttatg cactctcttc actctctcac acattaatcg attcatagac   3120
tcccatattc cttgatgaag gtgtgggttt ttagctttt ttcccgattt gtaaaggaa    3180
gaggctgacg atgttaggaa aaagagaacg gagccgaaaa aacatccgta gtaagtcttc   3240
cttttaagcc gacactttt agacagcatt cgccgctagt tttgaagttt aaattttaaa   3300
aaataaaaat tagtttcaat tttttttaat tactaaatag gcaaaagttt tttcaagaac   3360
tctagaaaaa ctagccttaat tcatgggtac tagaaaaatt cttgttttaa atttaatatt  3420
tatcttaaga tgtaattacg agaagctttt ttgaaaattc tcaattaaaa gaatttgccg   3480
atttagaata aaagtcttca gaaatgagta aaagctcaaa ttgagagttt gttttaaag    3540
gaaaacacg aaaaaagaac actatttatc ttttcctccc cgcgtaaaat tagttgttgt    3600
```

```
gataatagtg atccgctgtc tatttgcact cggctcttca caccgtgctt cctctcactt   3660
gacccaacag gaaaaaaaaa catcacgtct gagacggtga attgccttat caagagcgtc   3720
gtctctttca cccagtaaca aaaaaatttt ggtttcttta ctttatattt atgtaggtca   3780
caaaaaaaaa gtgatgcagt tttgtgggtc ggttgtctcc acaccacctc cgcctccagc   3840
agcacacaat catcttcgtg tgttctcgac gattccttgt atgccgcggt cgtgaatgca   3900
ccacattcga cgcgcaacta cacaccacac tcactttcgg tggtattact acacgtcatc   3960
gttgttcgta gtctcccgct ctttcgtccc cactcactcc tcattattcc ccttggtgta   4020
ttgattttt ttaaatggta caccactcct gacgtttcta ccttcttgtt ttccgtccat   4080
ttagatttta tctggaaatt ttttaaaat tttaggccag agagttctag ttcttgttct   4140
aaaagtctag gtcagacata cattttctat ttctcatcaa aaaaaagtt gataaagaaa    4200
actggttatt cagaaagagt gtgtctcgtt gaaattgatt caaaaaaaa ttcccacccc    4260
tcgcttgttt ctcaaaatat gagatcaacg gattttttcc ttctcgattc aattttttgc   4320
tgcgctctgt ctgccaaagt gtgtgtgtcc gagcaaaaga tgagagaatt tacaaacaga   4380
aatgaaaaaa agttggccaa ataatgaagt tttatccgag attgatggga aagatattaa   4440
tgttctttac ggtttggagg ggagagagag atagattttc gcatcaaact ccgccttta    4500
catgtctttt agaatctaaa atagattttt ctcatcattt ttaatagaaa atcgagaaat   4560
tacagtaatt tcgcaatttt cttgccaaaa atacacgaaa tttgtgggtc tcgccacgat   4620
ctcggtctta gtggttcatt tggtttaaaa gtttataaaa tttcaaattc tagtgtttaa   4680
tttccgcata attggaccta aaatgggttt ttgtcatcat tttcaacaag aaatcgtgaa   4740
aatcctgttg tttcgcaatt ttcttttcaa aaatacacga aatatatggt aatttcccga   4800
aatattgagg gtctcgccac gatttcagtc acagtggcca ggatttatca cgaaaaagt    4860
tcgcctagtc tcacatttcc ggaaaaccga atctaaatta gttttttgtc atcatttga    4920
acaaaaaatc gagacatccc tatagtttcg caattttcgt cgcttttctc tccaaaaatg   4980
acagtctaga attaaaattc gctggaactg ggaccatgat atcttttctc cccgttttc    5040
attttatttt ttattacact ggattgacta aaggtcacca ccaccgccag tgtgtgccat   5100
atcacacaca cacacacaca caatgtcgag atttttatgtg ttatccctgc ttgatttcgt  5160
tccgttgtct ctctctctct attcatcttt tgagccgaga agctccagag aatggagcac   5220
acaggatccc ggcgcgcgat gtcgtcggga gatggcgccg cctgggaagc cgccgagaga   5280
tatcagggaa gatcgtctga tttctcctcg gatgccacct catctctcga gtttctccgc   5340
ctgttactcc ctgccgaacc tgatatttcc cgttgtcgta aagagatgtt ttatttttac   5400
tttacaccgg gtcctctctc tctgccagca cagctcagtg ttggctgtgt gctcgggctc   5460
ctgccaccgg cggcctcatc ttcttcttct tcttctctcc tgctctcgct tatcacttct   5520
tcattcattc ttattccttt tcatcatcaa actagcattt cttactttat ttattttttt   5580
caattttcaa ttttcagata aaaccaaaact acttgggtta cagccgtcaa catggaggac   5640
gcgcatgcca aagacgccaa tgaggtactt ttatagtttt taaatttag ttttaatac     5700
aatttatttt ccaggtgtgc aaattcttcg gaacgggtcc ggagggattg actccacagc   5760
aagttgaaac attgaggaac aaatatggag aaaatggttg gtttttaca tggatttctc    5820
attaaaaatt gaattttttc cagaaatgcc cgccgaagag ggaaaatcac tgtgggagct   5880
gattctcgag caattcgacg atcttctcgt caagattctc ctcctcgccg ccatcatctc   5940
gtttgtgctc gccctttttcg aagagcacga agatcagaca gaagcagtga cggcgttcgt   6000
```

```
cgaaccgttc gtcatccttc tcattcttat tgccaacgcg accgtcggag tgtggcaggt    6060
aggaacaaca cagacaggcg cacgcgctga agaaaataa gaagaagaag aaaaagcaca     6120
gttgttttct gtgttttgt agatcaaaag aaaggaacta ggagtgattg cacagagaga     6180
gagagagaga ataatgtct ttttgacttg tttttgttgg tgagagagat agggaaaaag     6240
agtccctaaa gaaaaatag tgtaacgggc ggtccggaag aaatgctctt tgcgccgaaa    6300 agttttttgaa aaagaagaa atgatgaag gaaaggcgtg cgtcatgagc ttcgcattta    6360
cgtacgcaaa aagtgaggga tatgtgaaaa agatattggg tgatagaata gttgatggat    6420
tgggctgcac tatttgcctc aatttgccac aaatttccat ctaatttgtc ataattttcc    6480
aggaacgaaa tgctgaatcg gccatcgaag cgctcaagga atacgaacca gaaatggcca    6540
aggtcatccg atccggacac cacggaattc agatggttcg cgctaaggaa ctcgtgccag    6600
gagatcttgt cgaagtttca ggttagcaaa aactttttttt tttaactttc aaattttaaa    6660
ccatatattt ttcagtcgga gacaagatcc cagccgatct ccgtcttgtg aagatctact    6720
ccaccaccat ccgtatcgat cagtccatcc tcaccggaga atctgtgtct gttatcaagc    6780
acaccgactc tgtgccagat ccacgcgctg ttaaccagga caagaagaat tgtctgttct    6840
cgggaaccaa tgtcgcatct ggaaaggctc gtggaatcgt cttcgaaccc ggattgacca    6900
ctgaaatcgg aaagatccgt accgaaatgg ctgagaccga aatgagaag acaccacttc     6960 aacagaagtt ggacgaattc ggagagcaac tttccaaggt tatctctgtt atttgcgttg    7020
ctgtttgggc tatcaacatt ggacatttca acgatccagc tcacggtgga tcatgggtta    7080
agggagcaat ctactactc aaaatcgccg ttgctcttgc cgtcgctgct attccagaag     7140
gacttccagc tgtcatcacc acgtgccttg ccctcggaac tcgccgtatg ccaagaaga    7200 acgctattgt aagatccctt ccatccgtcg aaactcttgg atgcacatct gttatctgct    7260
ctgacaagac tggaactctc accaccaacc agatgtctgt gtcaaagatg ttcatcgctg    7320
gacaagcttc tggagacaac atcaacttca ccgagttcgc catctccgga tccacctacg    7380
agccagtcgg aaaggtttcc accaatggac gtgaaatcaa cccagctgct ggagaattcg    7440
aatcactcac cgagttggcc atgatctgcg ctatgtgcaa tgattcatct gttgattaca    7500
atgagaccaa gaagatctac gagaaagtcg gagaagccac tgaaactgct cttatcgttc    7560
ttgctgagaa gatgaatgtt ttcggaacct cgaaagccgg acttcacca aaggagctcg    7620 gaggagtttg caaccgtgtc atccaacaaa aatggaagaa ggagttcaca ctcgagttct    7680
cccgtgatcg taaatccatg tccgcctact gcttcccagc ttccggagga tctggagcca    7740
agatgttcgt gaagggagcc ccagaaggag ttctcggaag atgcacccac gtcagagtta    7800
acggacaaaa ggttccactc acctctgcca tgactcagaa gattgttgac caatgcgtgc    7860
aatacggaac cggaagagat acccttcgtt gtcttgccct cggaaccatc gatacccag    7920 tcagcgttag caacatgaac ctcgaagact ctacccaatt cgtcaaatac gaacaagaca    7980
tcacatttgt cggagtcgtc ggaatgcttg acccccaag aactgaagtt tcggactcga    8040
tcaaggcttg taaccacgct ggaatccgtg tcatcatgat caccggagac aacaagaaca    8100
ccgctgaggc tatcggaaga agaatcggac tcttcggaga aacgaggat accactggaa    8160 aagcttacac tggacgtgaa tttgacgatc ttccaccaga gcaacaatct gaagcctgcc    8220
gcagagctaa gcttttcgcc cgtgtcgagc catctcacaa gtccaagatt gtcgatatcc    8280
ttcaatccca gggagagatt actgctatga ccggagacgg agtcaacgac gctccagctt    8340
```

-continued

```
tgaagaaggc cgaaatcgga atttctatgg gatcaggaac tgctgtcgcc aagtctgcat    8400
ctgaaatggt tcttgctgac gataacttcg catccattgt gtctgctgtc gaagaaggac    8460
gtgctattta caacaacatg aaacaattca tcagatatct catctcatct aacgtcggag    8520
aagtcgtctc catcttcatg gtcgccgcac tcggaattcc agaggctctc attccagttc    8580
aacttctctg ggttaacttg gtcactgacg gtcttccagc cactgctctc ggattcaatc    8640
caccagatct tgacattatg gacagacatc cacgttcagc caacgatgga ctcatctctg    8700
gatggctctt cttcagatat cttgctgtcg gaagtacgtt taaaaaattc ccctaaaaaa    8760
gtataattct aaaattgaaa ttttccagcc tacgtcggag ttgccaccgt cggagcctca    8820
atgtggtggt tcttgttgta cgaggaggga ccacagatca cctactacca gctcactcac    8880
tggatgagat gtgaaatcga gccagacaac tttgccgatc ttgactgcgc cgtattcgag    8940
gacaatcacc cgaacgccat ggctctgtcc gtgcttgtca ccattgagat gctcaacgcc    9000
atcaactcac tttccgagaa tcaatcgctt ttagtgatgc caccatggaa gaacatctgg    9060
ctgatggccg ccatttccct ttcgatgtct cttcactttg tcattctcta cgttgacatc    9120
atggccacca tcttccaggt atcacaatta atcatatatt aatcgaaaca tctaattcaa    9180
atcttcagat caccctctc aactgggtcg aatggatcgc cgtgttgaag atctcactgc    9240
cagtgctcct tctcgatgaa attctcaagt tcatcgccag aaactacatc gacggtaagc    9300
cggagacggt cggcgcgaag gcacgtagtg ccatctcgct gctcgcctgg gtgtctgtga    9360
cgctcgccta ctttgcgtgg atgttgggcc cgtacgccga gctcattaac catgcgctcg    9420
tcggtccatc tgtcgatccg tcgaaattcg acgcggttgt cacgcccgac aagttacata    9480
acgaattgtg attgaagttc ttctaacccc caaaccaacc gcctctcaaa caacttgtga    9540
tgatttctct ttattttctc tctctttctt gttctaatca ttttgggcct ttttcccttt    9600
ttctctctgc agtgtgttaa ctgatccata atccttcgtg taaaccccc tctccctact    9660
tttaggattt cttcctcgtt gctcattgta ttttgtccaa atcgccacaa tttccctaca    9720
aatatatatg ttttttttgc taatttttg tgtttccctt ccttcttgtc cactgaaagt    9780
tctacgtctc tcgctctcca catccccatt gttctcccct tttttcataa taatttatta    9840
ttatccttt tttaaattaa tttttgttgc gtgtgaatct attaggagct cacaaataaa    9900
agtgatcctt taaaaaacct tacttccttc tgtttttct ctaacctaac caatgtgtct    9960
gttcagggag tgcctctttt ctttaccgaa tggtgtgcaa ttttgtcgac tgtcgatctc   10020
gtccatggca atgcaggatt tgaaactaaa tttccctgga aaagaaata attttggtga   10080
ttttcagttg aagctccaat caaggataaa cgcgactaaa aatgacagtg ctccctcaat   10140
cagagtgagc ccagccgccg cccatctcat ttttcagact ctttcatatt tctaagttt   10200
tccaattttt tttcttttgt agtgcgatcg ttttcgtttc gagacccgaa atcgaaagga   10260
tctcttttag agatctttag gatcttttt ctttgctcaa ctcatcattc tttgttttt   10320
cttctatatc ctcttgttga cggtgatcag acaaatttgt tagaaatatt attacatttc   10380
ctttaggttt cttctattaa aaaaaagaa aacttctgct aaattcgtgt acgttgtctc   10440
tcccatttct cattaaaaat cgatattaat tgtaattttt ggtttgtcct ccagtgtcgt   10500
gtgcgccatc gatggaaata aaaagtttc aaaactatta tagcttttct ttttatgaaa   10560
aatataaaat acaattagaa tgttttgtt aaatgcgata cggtgtgcgc ctttaaagag   10620
tagagtactg tagttccaaa attttgttgg tgcgggattt tcattgattt ttcatcgttt   10680
ttcgacaaaa atatatttat ttattgaaaa aagttaaata aaactattaa aaacacagaa   10740
```

-continued

```
ttttaacaa attgtgaaaa acacatgaaa aatcgatgac aattctacag taacgaacat    10800
tttgaattac agtaatcttt aaaggcgcgc acacgtttgc atttaattaa aatgtgtcgt    10860
gtcgagaccg actaccacgt ctcgttatta tagaacgagc aattacagcc taacatcaac    10920
tcagaacaaa ccaggatccc acgcaagttt aaaggagcat gctgggtatc acaacgattt    10980
tttgaagaga acgaggcccc acgaaacggg agcagaacg aaaaggggat ctgcaaaaag    11040
gggatctgca aaaggggat ctgcgaaaag gggagatatg aaaggggag atacgaaaag    11100 gggagctggc actgtgccaa acgcacaaaa cgcaattttt ctcacgcaac gcacgttgat    11160
ttttgaaatt ttcttctaga agatacgctt aacaacacgc gacgcgg              11207
```

<210> SEQ ID NO 3
<211> LENGTH: 5026
<212> TYPE: DNA
<213> ORGANISM: Caenorhabditis elegans

<400> SEQUENCE: 3

```
ttggttggca gctctctggc ttatcttttg agaggaaaaa gatccaacaa attttatct     60 cccttatccc tttttctctt catcactacc aataataata gttttttttt tcgtcgcgga    120
agcaaaatgg cgaacaagtg ttggaataag agtactccag ggatttaagg gctgaaagcc    180
agtgatttat gagctccaat ttttcagatg ttttttcctc catcgcgtat ttgtctaaac    240
attcgatttt cttcctgctt cccaactttt caaatcgaaa taaagagca tctgtcgctt    300 tttatcgatg tgcttctgtg agactaaaga actactcgtt ttcactcgtt ctctctctct    360
caactatcaa agttttgttg attgcgtgtg tcagcttcct tcttttatt atcatcttt    420 cattggagga aaaaaataac ttctgaagag caaaagaact aacttcgggg aatacagaga    480
aaattcctgt aaaaatctgg aaattttttc gcttaactcg aaatatttag tttttcactg    540
tgatttctgg gaaaaatcaa gaaatatttg cctaaaacac gagttttcac atgaaaaatg    600
aattatttat tgatttttta tggagattac aaaaaagaca cacgtgaaac tactgctacc    660
gtagttgtgt aaacgtagtg ttctctattt tagacctgtt taatgtatt ttttgcagtt    720 gaaaattttt aaaaatattt tagttatttt taaaaatatt taatttacaa aataattagc    780
ctgaacccat gaaaagatac gttatattta attttaccg taagactttc aagatcgttg    840
cgagacccgg cgcctaggtc aaagagcctc cctttaaacc catcaacacg ttttgccttt    900
ttcatcgatt ttttgcagtt cttttcttct ttccaactga ttttcttca tttttaaagt    960 tttttcctc attttcccca tttgaaatta ttaaacacg tgcaaccagc tggtaacatg    1020
tgtcacatgc cgttatctaa cttcaaaaca gtacatttcc gatcacacgt cccccgcgcc    1080
gagttttata gtttcattaa taacttttcg gttttgata atactaattg agttttatta    1140
attgtttcca tattcatcta gcactttgac ctgtccttct tcgaattctc aaatatttgc    1200
actctgggtt taggtgtgaa agaattgtc gtcattaagc ggggcatccg gggcaccgaa    1260 aaagccctc cgatttaac gaatttgaga taaagttgga gagagaccc agtgtttgct    1320 tgcccaagat atatatcttg gatttatcaa ttactgttg tcaacctgtc gccggcgccc    1380
cctttttgct cttgctccca cgccccgaga ttgaatttca atttattttc gaagtaagtc    1440
tcttgattgt ttcgaaaatc cgatgacagt tttcattact ttttgtctg ttgattttgt    1500 agggaaacat tgaatttttt ctgatctttc tttgatctta tgatttttca tttattccaa    1560
ttaaaaaaaa ttagcgcatt cagaaccaga gtgaagcttg agatgttgta ggtttatcaa    1620
```

```
aagatcaaaa tctcgaattc cttcgaaatg ttttagttt tcgacttccg tgtgatttct      1680
agcgatcctg acagagatca ctgaatttta atgttatcga gattgttgtg taggctccat      1740
ctcctctctg aagcttctga ttttgccgaa agtctagtta cttgccgact gctgacacta      1800
ggatatccca ctaccgtacc cattgttgga tccgtactct gctgcgactt cttctctgtt      1860
tcacgtgaac ctccgggatc gtcggtaagc ccgcccgtt atctgtgcca acttgtcttc       1920
gtgccctcga gcgacgagct cattcaatca cgccacgacc tccgtctgga cagatgctct      1980
cattgtctct gcgtctccaa gtattcgtca cactatctca tgcattctat tcaaaacgcg      2040
agagaaagcg cgggaacgag agagagttca gacagatcga acttgttttt atcccccccc      2100
ccctcgtccg gctgcagagc aaaaaaatac tgcttttcct tgcaaaattc ggtgctttct      2160
tcaaagagaa acttttgaag tcggcgcgag catttccttc tttgacttct ctctttccgc      2220
caaaaagcct agcatttta ttgataattt gattacacac actcagagtt cttcgacatg       2280
ataaagtgtt tcattggcac tcgccctaac agtacatgac aagggcggat tattatcgat      2340
cgatattgaa gacaaactcc aaatgtgtgc tcattttgga gccccgtgtg gggcagctgc      2400
tctcaatata ttactaggga gacgaggagg gggaccttat cgaacgtcgc atgagccatt      2460
ctttcttctt tatgcactct cttcactctc tcacacatta atcgattcat agactcccat      2520
attccttgat gaaggtgtgg gttttagct tttttccg atttgtaaaa ggaagaggct         2580
gacgatgtta ggaaaaagag aacggagccg aaaaaacatc cgtagtaagt cttccttta      2640 agccgacact ttttagacag cattcgccgc tagttttgaa gtttaaattt taaaaataa       2700 aaattagttt caattttttt taattactaa ataggcaaaa gttttttcaa gaactctaga      2760
aaaactagct taattcatgg gtactagaaa aattcttgtt ttaaatttaa tatttatctt      2820
aagatgtaat tacgagaagc ttttttgaaa attctcaatt aaaagaattt gccgatttag      2880
aataaaagtc ttcagaaatg agtaaaagct caaattagaa gtttgttttt aaaggaaaaa      2940
cacgaaaaaa gaacactatt tatctttcc tccccgcgta aaattagttg ttgtgataat       3000
agtgatccgt tgtctatttg cactcggctc ttcacaccgt gcttcctctc acttgaccca      3060
acaggaaaaa aaaacatcac gtctgagacg gtgaattgcc ttatcaagag cgtcgtctct      3120
ttcacccagt aacaaaaaa atttggtttc tttactttat atttatgtag gtcacaaaaa       3180 aaagtgatg cagttttgtg ggtcggttgt ctccacacca cctccgcctc cagcagcaca       3240
caatcatctt cgtgtgttct cgacgattcc ttgtatgccg cggtcgtgaa tgcaccacat      3300
tcgacgcgca actacacacc acactcactt tcggtggtat tactacacgt catcgttgtt      3360
cgtagtctcc cgctctttcg tccccactca ctcctcatta ttcccttgg tgtattgatt       3420 tttttaaat ggtacaccac tcctgacgtt tctaccttct tgttttccgt ccatttagat       3480
tttatctgga aatttttta aaattttagg ccagagagtt ctagttcttg ttctaaaagt      3540
ctaggtcaga catacatttt ctatttctca tcaaaaaaaa agttgataaa gaaaactggt      3600
tattcagaaa gagtgtgtct cgttgaaatt gattcaaaaa aaaattccca ccctcgcttt      3660
gtttctcaaa atatgagatc aacggatttt ttccttctcg attcaatttt ttgctgcgct      3720
ctgtctgcca agtgtgtgt gtccgagcaa aagatgagag aatttacaaa cagaaatgaa       3780 aaaagttgg ccaataatg aagttttatc cgagattgat gggaaagata ttaatgttct        3840
ttacggtttg gagggagag agagatagat tttcgcatca aactccgcct tttcatgtc        3900 ttttagaatc taaaatagat ttttctcatc atttttaata gaaaatcgag aaattacagt      3960
aatttcgcaa ttttcttgcc aaaaatacac gaaatttgtg ggtctcgcca cgatctcggt      4020
```

-continued

| | | |
|---|---|---|
| cttagtggtt catttggttt aaaagttttat aaaatttcaa attctagtgt ttaatttccg | 4080 |
| cataattgga cctaaaatgg gttttttgtca tcattttcaa caagaaatcg tgaaaatcct | 4140 |
| gttgtttcgc aattttcttt tcaaaaatac acgaaatata tggtaatttc ccgaaatatt | 4200 |
| gagggtctcg ccacgatttc agtcacagtg gccaggattt atcacgaaaa aagttcgcct | 4260 |
| agtctcacat ttccggaaaa ccgaatctaa attagttttt tgtcatcatt ttgaacaaaa | 4320 |
| aatcgagaca tccctatagt ttcgcaattt tcgtcgcttt tctctccaaa atgacagtc | 4380 |
| tagaattaaa attcgctgga actgggacca tgatatcttt tctccccgtt tttcatttta | 4440 |
| ttttttatta cactggattg actaaaggtc accaccaccg ccagtgtgtg ccatatcaca | 4500 |
| cacacacaca cacacaatgt cgagatttta tgtgttatcc ctgcttgatt tcgttccgtt | 4560 |
| gtctctctct ctctattcat cttttgagcc gagaagctcc agagaatgga gcacacagga | 4620 |
| tcccggcgcg cgatgtcgtc gggagatggc gccgcctggg aagccgccga gagatatcag | 4680 |
| ggaagatcgt ctgatttctc ctcggatgcc acctcatctc tcgagtttct ccgcctgtta | 4740 |
| ctccctgccg aacctgatat ttcccgttgt cgtaaagaga tgttttattt ttactttaca | 4800 |
| ccgggtcctc tctctctgcc agcacagctc agtgttggct gtgtgctcgg gctcctgcca | 4860 |
| ccggcggcct catcttcttc ttcttcttct ctcctgctct cgcttatcac ttcttcattc | 4920 |
| attcttattc cttttcatca tcaaactagc atttcttact ttatttattt ttttcaattt | 4980 |
| tcaattttca gataaaacca aactacttgg gttacagccg tcaaca | 5026 |

<210> SEQ ID NO 4
<211> LENGTH: 2915
<212> TYPE: DNA
<213> ORGANISM: Caenorhabditis elegans

<400> SEQUENCE: 4

| | | |
|---|---|---|
| ctgcagagca aaaaatact gcttttcctt gcaaaattcg gtgctttctt caaagagaaa | 60 |
| cttttgaagt cggcgcgagc atttccttct ttgacttctc tctttccgcc aaaaagccta | 120 |
| gcatttttat tgataaatttg attacacaca ctcagagttc ttcgacatga taaagtgttt | 180 |
| cattggcact cgccctaaca gtacatgaca agggcggatt attatcgatc gatattgaag | 240 |
| acaaactcca aatgtgtgct cattttggag ccccgtgtgg ggcagctgct ctcaatatat | 300 |
| tactagggag acgaggaggg ggaccttatc gaacgtcgca tgagccattc tttcttcttt | 360 |
| atgcactctc ttcactctct cacacattaa tcgattcata gactcccata ttccttgatg | 420 |
| aaggtgtggg ttttttagctt ttttttcccga tttgtaaaag gaagaggctg acgatgttag | 480 |
| gaaaaagaga acgagccga aaaaacatcc gtagtaagtc ttcctttttaa gccgacactt | 540 |
| tttagacagc attcgccgct agttttgaag ttttaaatttt aaaaaataaa aattagtttc | 600 |
| aattttttttt aattactaaa taggcaaaag ttttttcaag aactctagaa aaactagctt | 660 |
| aattcatggg tactagaaaa attcttgttt taaatttaat atttatctta agatgtaatt | 720 |
| acgagaagct ttttttgaaaa ttctcaatta aaagaatttg ccgatttaga ataaaagtct | 780 |
| tcagaaatga gtaaaagctc aaattagaag tttgttttta aaggaaaaac acgaaaaaag | 840 |
| aacactattt atcttttcct ccccgcgtaa aattagttgt tgtgataata gtgatccgct | 900 |
| gtctatttgc actcggctct tcacaccgtg cttcctctca cttgacccaa caggaaaaaa | 960 |
| aaacatcacg tctgagacgg tgaattgcct tatcaagagc gtcgtctctt tcacccagta | 1020 |
| acaaaaaaaa tttggtttct ttactttata tttatgtagg tcacaaaaaa aaagtgatgc | 1080 |

-continued

```
agttttgtgg gtcggttgtc tccacaccac ctccgcctcc agcagcacac aatcatcttc    1140
gtgtgttctc gacgattcct tgtatgccgc ggtcgtgaat gcaccacatt cgacgcgcaa    1200
ctacacacca cactcacttt cggtggtatt actacacgtc atcgttgttc gtagtctccc    1260
gctctttcgt ccccactcac tcctcattat tccccttggt gtattgattt ttttttaaatg   1320 gtacaccact cctgacgttt ctaccttctt gttttccgtc catttagatt ttatctggaa    1380 attttttttaa aattttaggc cagagagttc tagttcttgt tctaaaagtc taggtcagac   1440
atacattttc tatttctcat caaaaaaaaa gttgataaag aaaactggtt attcagaaag    1500
agtgtgtctc gttgaaattg attcaaaaaa aaattcccac ccctcgcttg tttctcaaaa    1560
tatgagatca acggattttt tccttctcga ttcaatttt tgctgcgctc tgtctgccaa     1620
agtgtgtgtg tccgagcaaa agatgagaga atttacaaac agaaatgaaa aaaagttggc   1680
caaataatga agttttatcc gagattgatg ggaaagatat taatgttctt tacggtttgg   1740
aggggagaga gagatagatt ttcgcatcaa actccgcctt ttacatgtct tttagaatct   1800
aaaatagatt tttctcatca ttttttaatag aaaatcgaga aattacagta atttcgcaat  1860
tttcttgcca aaaatacacg aaatttgtgg gtctcgccac gatctcggtc ttagtggttc   1920
atttggttta aaagtttata aaatttcaaa ttcagtgtt taatttccgc ataattggac    1980
ctaaaatggg ttttttgtcat cattttcaac aagaaatcgt gaaaatcctg ttgtttcgca   2040
attttctttt caaaaataca cgaaatatat ggtaatttcc cgaaatattg agggtctcgc   2100
cacgatttca gtcacagtgg ccaggattta tcacgaaaaa agttcgccta gtctcacatt   2160
tccggaaaac cgaatctaaa ttagtttttt gtcatcattt tgaacaaaaa atcgagacat   2220
ccctatagtt tcgcaatttt cgtcgctttt ctctccaaaa atgacagtct agaattaaaa   2280
ttcgctggaa ctgggaccat gatatctttt ctccccgttt ttcatttat tttttattac    2340 actggattga ctaaaggtca ccaccaccgc cagtgtgtgc catatcacac acacacacac   2400
acacaatgtc gagattttat gtgttatccc tgcttgattt cgttccgttg tctctctctc   2460
tctattcatc ttttgagccg agaagctcca gagaatggag cacacaggat cccggcgcgc   2520
gatgtcgtcg ggagatggcg ccgcctggga agccgccgag agatatcagg gaagatcgtc   2580
tgatttctcc tcggatgcca cctcatctct cgagtttctc cgcctgttac tccctgccga   2640
acctgatatt tcccgttgtc gtaaagagat gtttttattt tactttacac cgggtcctct   2700
ctctctgcca gcacagctca gtgttggctg tgtgctcggg ctcctgccac cggcggcctc   2760
atcttcttct tcttcttctc tcctgctctc gcttatcact tcttcattca ttcttattcc   2820
ttttcatcat caaactagca tttcttactt tatttatttt tttcaatttt caattttcag   2880
ataaaaccaa actacttggg ttacagccgt caaca                              2915
```

<210> SEQ ID NO 5
<211> LENGTH: 6612
<212> TYPE: DNA
<213> ORGANISM: Caenorhabditis elegans

<400> SEQUENCE: 5

```
tcgactctag ttttgaaatc caaaaaaaaa acaaagttca ataaaatgtt acccaattgt      60
gcgatttttg cttttaaaat acggtacccg gtctcgatgc ggcaattgtt tggtaaatgt    120
aaaagggtgt gcgcctttaa agagtactgt aatttcaatc ttccgacact gctgaatttt    180
tattgacttt ttgttcatta atttttatata tgatttattg gtatgttaaa aaaacaccca   240
ttttcaaatc tattaaaatt ccacaacaac aaaagttcga gattacagta cttttttagag  300
```

```
gcgcacatcc tttttgggat actaaacaat tgtcgcgtcg agaccaggta ccatatttcc    360
aaaacacaat ttcgcgtgta aataaaaaat atcaacataa taatttccat ttttcgaaat    420
ttaaagttaa tcacttttg gtttagatta tgatttcaca cgttttttc cttctagttc      480 tcttttttt gttatttgcc tgaaaaatgg tctgaaaact taggcaatca gcaatgtgtc     540
acataatttc tcccagagaa atcccttca acaaaatctc ccggattgac ctgtgtgctc     600
gaccttgata aattggttgg cagctctctg gcttatcttt tgagaggaaa aagatccaac    660 aaattttat ctcccttatc cctttttctc ttcatcacta ccaataataa tagttttttt     720
tttcgtcgcg gaagcaaaat ggcgaacaag tgttggaata agagtactcc agggatttaa    780
gggctgaaag ccagtgattt atgagctcca atttttcaga tgttttttcc tccatcgcgt    840
atttgtctaa acattcgatt ttcttcctgc ttcccaactt ttcaaatcga aataaaagag    900
catctgtcgc ttttatcga tgtgcttctg tgagactaaa gaactactcg ttttcactcg     960
ttctctctct ctcaactatc aaagttttgt tgattgcgtg tgtcagcttc cttctttta    1020 ttatcatctt ttcattggag gaaaaaata acttctgaag agcaaagaa ctaacttcgg     1080 ggaatacaga gaaaattcct gtaaaaatct ggaattttt tcgcttaact cgaaatattt    1140 agttttcac tgtgatttct gggaaaaatc aagaaatatt tgcctaaaac acgagttttc    1200
acatgaaaaa tgaattattt attgatttt tatggagatt acaaaaaga cacacgtgaa     1260 actactgcta ccgtagttgt gtaaacgtag tgttctctat tttagacctg tttaatgtat   1320 tttttttgcag ttgaaaattt ttaaaaatat tttagttatt tttaaaaata tttaatttac  1380
aaaataatta gcctgaaccc atgaaaagat acgttatatt taattttac cgtaagactt    1440 tcaagatcgt tgcgagaccc ggcgcctagg tcaaagagcc tcccttaaa cccatcaaca    1500 cgttttgcct ttttcatcga tttttgcag ttcttttctt ctttccaact gattttctt     1560 catttttaaa gtttttttcc tcatttttcc catttgaaat tatttaaaca cgtgcaacca   1620
gctggtaaca tgtgtcacat gccgttatct aacttcaaaa cagtacattt ccgatcacac   1680
gtcccccgcg ccgagtttta tagtttcatt ataactttt cggttttga taatactaat     1740 tgagttttat taattgtttc catattcatc tagcactttg acctgtcctt cttcgaattc    1800
tcaaatattt gcactctggg tttaggtgtg aaaagaattg tcgtcattaa gcggggcatc   1860
cggggcaccg aaaaaagccc tccgatttta acgaatttga gataaagttg gagagagagc   1920
ccagtgtttg cttcccaag atatatatct tggatttatc aattactgtt tgtcaacctg    1980
tcgccggcgc ccccttttg ctcttgctcc cacgccccga gattgaattt caatttatt    2040 tcgaagtaag tctcttgatt gtttcgaaaa tccgatgaca gttttcatta cttttttgtc   2100
tgttgatttt gtagggaaac attgaaattt ttctgatctt tctttgatct tatgatttt    2160 catttattcc aattaaaaaa aattagcgca ttcagaacca gagtgaagct tgagatgttg   2220
taggtttatc aaaagatcaa atctcgaat tccttcgaaa tgttttagt tttcgacttc     2280 cgtgtgattt ctagcgatcc tgacagagat cactgaattt taatgttatc gagattgttg   2340
tgtaggctcc atctcctctc tgaagcttct gattttgccg aaagtctagt tacttgccga   2400
ctgctgacac taggatatcc cactaccgta cccattgttg gatccgtact ctgctgcgac   2460
ttcttctctg tttcacgtga acctccggga tcgtcggtaa gccccgcccg ttatctgtgc   2520
caacttgtct tcgtgccctc gagcgacgag ctcattcaat cacgcacga cctccgtctg    2580 gacagatgct ctcattgtct ctgcgtctcc aagtattcgt cacactatct catgcattct   2640
```

-continued

```
attcaaaacg cgagagaaag cgcgggaacg agagagagtt cagacagatc gaacttgttt    2700
ttatccccc ccccctcgtc cggctgcaga gcaaaaaaat actgcttttc cttgcaaaat    2760
tcggtgcttt cttcaaagag aaactttga agtcggcgcg agcatttcct tctttgactt    2820
ctctctttcc gccaaaaagc ctagcatttt tattgataat ttgattacac acactcagag   2880
ttcttcgaca tgataaagtg tttcattggc actcgcccta acagtacatg acaagggcgg   2940
attattatcg atcgatattg aagacaaact ccaaatgtgt gctcatttg gagccccgtg    3000
tggggcagct gctctcaata tattactagg gagacgagga ggggacctt atcgaacgtc    3060
gcatgagcca ttctttcttc tttatgcact ctcttcactc tctcacacat taatcgattc    3120
atagactccc atattccttg atgaaggtgt gggtttttag cttttttcc cgatttgtaa    3180
aaggaagagg ctgacgatgt taggaaaaag agaacggagc cgaaaaaaca tccgtagtaa   3240
gtcttccttt taagccgaca cttttagac agcattcgcc gctagttttg aagtttaaat    3300
tttaaaaat aaaaattagt ttcaatttt tttaattact aaataggcaa aagttttttc    3360
aagaactcta gaaaaactag cttaattcat gggtactaga aaaattcttg ttttaaattt   3420
aatatttatc ttaagatgta attacgagaa gcttttttga aaattctcaa ttaaaagaat   3480
ttgccgattt agaataaaag tcttcagaaa tgagtaaaag ctcaaattag aagtttgttt   3540
ttaaaggaaa aacacgaaaa aagaacacta tttatctttt cctccccgcg taaaattagt   3600
tgttgtgata atagtgatcc gctgtctatt tgcactcggc tcttcacacc gtgcttcctc   3660
tcacttgacc caacaggaaa aaaaacatc acgtctgaga cggtgaattg ccttatcaag   3720
agcgtcgtct ctttcaccca gtaacaaaaa aaatttggtt tctttacttt atatttatgt   3780
aggtcacaaa aaaaaagtga tgcagttttg tgggtcggtt gtctccacac cacctccgcc   3840
tccagcagca cacaatcatc ttcgtgtgtt ctcgacgatt ccttgtatgc cgcggtcgtg   3900
aatgcaccac attcgacgcg caactacaca ccacactcac tttcggtggt attactacac   3960
gtcatcgttg ttcgtagtct cccgctcttt cgtccccact cactcctcat tattcccctt   4020
ggtgtattga ttttttttaa atggtacacc actcctgacg tttctacctt cttgttttcc   4080
gtccatttag attttatctg gaatttttt taaaatttta ggccagagag ttctagttct   4140
tgttctaaaa gtctaggtca gacatacatt ttctatttct catcaaaaaa aaagttgata   4200
aagaaaactg gttattcaga aagagtgtgt ctcgttgaaa ttgattcaaa aaaaaattcc   4260
cacccctcgc ttgtttctca aaatatgaga tcaacggatt ttttccttct cgattcaatt   4320
ttttgctgcg ctctgtctgc caaagtgtgt gtgtccgagc aaaagatgag agaatttaca   4380
aacagaaatg aaaaaaagtt ggccaaataa tgaagtttta tccgagattg atgggaaaga   4440
tattaatgtt cttacggtt tggaggggag agagagatag atttcgcat caaactccgc    4500
cttttacatg tcttttagaa tctaaaatag atttttctca tcatttttaa tagaaaatcg   4560
agaaattaca gtaatttcgc aattttcttg ccaaaaatac acgaaatttg tgggtctcgc   4620
cacgatctcg gtcttagtgg ttcatttggt ttaaaagttt ataaaatttc aaattctagt   4680
gtttaatttc cgcataattg gacctaaaat gggttttgt catcatttc aacaagaaat    4740
cgtgaaaatc ctgttgtttc gcaatttct tttcaaaaat acacgaaata tatggtaatt   4800
tcccgaaata ttgagggtct cgccacgatt tcagtcacag tggccaggat ttatcacgaa   4860
aaagttcgc ctagtctcac atttccggaa aaccgaatct aaattagttt tttgtcatca    4920
ttttgaacaa aaaatcgaga catccctata gtttcgcaat tttcgtcgct tttctctcca   4980
aaaatgacag tctagaatta aaattcgctg gaactgggac catgatatct tttctccccg   5040
```

-continued

```
tttttcattt tatttttat tacactggat tgactaaagg tcaccaccac cgccagtgtg    5100
tgccatatca cacacacaca cacacacaat gtcgagattt tatgtgttat ccctgcttga    5160
tttcgttccg ttgtctctct ctctctattc atcttttgag ccgagaagct ccagagaatg    5220
gagcacacag gatcccggcg cgcgatgtcg tcgggagatg gcgccgcctg ggaagccgcc    5280
gagagatatc agggaagatc gtctgatttc tcctcggatg ccacctcatc tctcgagttt    5340
ctccgcctgt tactccctgc cgaacctgat atttcccgtt gtcgtaaaga gatgttttta    5400
ttttacttta caccgggtcc tctctctctg ccagcacagc tcagtgttgg ctgtgtgctc    5460
gggctcctgc caccggcggc ctcatcttct tcttcttctt ctctcctgct ctcgcttatc    5520
acttcttcat tcattcttat tccttttcat catcaaacta gcatttctta ctttatttat    5580
ttttttcaat tttcaatttt cagataaaac caaactactt gggttacagc cgtcaacatg    5640
gaggacgcgc atgccaaaga cgccaatgag gtacttttat agttttaaa ttttagtttt    5700 taatacaatt tattttccag gtgtgcaaat tcttcggaac gggtccggag ggattgactc    5760
cacagcaagt tgaaacattg aggaacaaat atggagaaaa tggttggttt tttacatgga    5820
tttctcatta aaaattgaat tttttccaga aatgcccgcc gaagagggaa aatcactgtg    5880
ggagctgatt ctcgagcaat tcgacgatct tctcgtcaag attctcctcc tcgccgccat    5940
catctcgttt gtgctcgccc ttttcgaaga gcacgaagat cagacagaag cagtgacggc    6000
gttcgtcgaa ccgttcgtca tccttctcat tcttattgcc aacgcgaccg tcggagtgtg    6060
gcaggtagga acaacacaga caggcgcacg cgctgaaaga aaataagaag aagaagaaaa    6120
agcacagttg ttttctgtgt ttttgtagat caaaagaaag gaactaggag tgattgcaca    6180
gagagagaga gagagaaata atgtcttttt gacttgtttt tgttggtgag agagataggg    6240
aaaaagagtc cctaaagaaa aaatagtgta acgggcggtc cggaagaaat gctctttgcg    6300
ccgaaaagtt tttgaaaaaa gaagaaaatg atgaaggaaa ggcgtgcgtc atgagcttcg    6360
catttacgta cgcaaaaagt gagggatatg tgaaaaagat attgggtgat agaatagttg    6420
atggattggg ctgcactatt tgcctcaatt tgccacaaat ttccatctaa tttgtcataa    6480
ttttccagga acgaaatgct gaatcggcca tcgaagcgct caaggaatac gaaccagaaa    6540
tggccaaggt catccgatcc ggacaccacg gaattcagat ggttcgcgct aaggaactcg    6600
tgccaggaga tc                                                       6612
```

<210> SEQ ID NO 6
<211> LENGTH: 3180
<212> TYPE: DNA
<213> ORGANISM: Caenorhabditis elegans

<400> SEQUENCE: 6

```
atggaggacg cgcatgccaa agacgccaat gaggtgtgca aattcttcgg aacgggtccg      60
gagggattga ctccacagca agttgaaaca ttgaggaaca atatggaga aaatgaaatg     120 cccgccgaag agggaaaatc actgtgggag ctgattctcg agcaattcga cgatcttctc     180
gtcaagattc tcctcctcgc cgccatcatc tcgtttgtgc tcgcccttt cgaagagcac     240 gaagatcaga cagaagcagt gacggcgttc gtcgaaccgt tcgtcatcct tctcattctt     300
attgccaacg cgaccgtcgg agtgtggcag gaacgaaatg ctgaatcggc catcgaagcg     360
ctcaaggaat acgaaccaga aatggccaag gtcatccgat ccggacacca cggaattcag     420
atggttcgcg ctaaggaact cgtgccagga gatcttgtcg aagtttcagt cggagacaag     480
```

-continued

```
atcccagccg atctccgtct tgtgaagatc tactccacca ccatccgtat cgatcagtcc    540
atcctcaccg gagaatctgt gtctgttatc aagcacaccg actctgtgcc agatccacgc    600
gctgttaacc aggacaagaa gaattgtctg ttctcgggaa ccaatgtcgc atctggaaag    660
gctcgtggaa tcgtcttcgg aaccggattg accactgaaa tcggaaagat ccgtaccgaa    720
atggctgaga ccgagaatga aagacacca cttcaacaga agttggacga attcggagag     780
caactttcca aggttatctc tgttatttgc gttgctgttt gggctatcaa cattggacat    840
ttcaacgatc cagctcacgg tggatcatgg gttaagggag caatctacta cttcaaaatc    900
gccgttgctc ttgccgtcgc tgctattcca aaggacttc cagctgtcat caccacgtgc     960
cttgccctcg gaactcgccg tatggccaag aagaacgcta ttgtaagatc ccttccatcc   1020
gtcgaaactc ttggatgcac atctgttatc tgctctgaca agactggaac tctcaccacc   1080
aaccagatgt ctgtgtcaaa gatgttcatc gctggacaag cttctggaga caacatcaac   1140
ttcaccgagt tcgccatctc cggatccacc tacgagccag tcggaaaggt ttccaccaat   1200
ggacgtgaaa tcaacccagc tgctggagaa ttcgaatcac tcaccgagtt ggccatgatc   1260
tgcgctatgt gcaatgattc atctgttgat tacaatgaga ccaagaagat ctacgagaaa   1320
gtcggagaag ccactgaaac tgctcttatc gttcttgctg agaagatgaa tgttttcgga   1380
acctcgaaag ccggactttc accaaaggag ctcgaggagg tttgcaaccg tgtcatccaa   1440
caaaaatgga agaaggagtt cacactcgag ttctcccgtg atcgtaaatc catgtccgcc   1500
tactgcttcc cagcttccgg aggatctgga gccaagatgt tcgtgaaggg agccccagaa   1560
ggagttctcg gaagatgcac ccacgtcaga gttaacggac aaaaggttcc actcacctct   1620
gccatgactc agaagattgt tgaccaatgc gtgcaatacg gaaccggaag agataccctt   1680
cgttgtcttg ccctcggaac catcgatacc ccagtcagcg ttagcaacat gaacctcgaa   1740
gactctaccc aattcgtcaa atacgaacaa gacatcacat ttgtcggagt cgtcggaatg   1800
cttgaccccc aagaactga gtttcggac tcgatcaagg cttgtaacca gctggaatc     1860 cgtgtcatca tgatcaccgg agacaacaag aacaccgctg aggctatcgg aagaagaatc   1920
ggactcttcg gagagaacga ggataccact ggaaaagctt acactggacg tgaatttgac   1980
gatcttccac cagagcaaca atctgaagcc tgccgcagca ctaagctttt cgcccgtgtc   2040
gagccatctc acaagtccaa gattgtcgat atccttcaat cccagggaga gattactgct   2100
atgaccggag acggagtcaa cgacgctcca gctttgaaga aggccgaaat cggaatttct   2160
atgggatcag gaactgctgt cgccaagtct gcatctgaaa tggttcttgc tgacgataac   2220
ttcgcatcca ttgtgtctgc tgtcgaagaa ggacgtgcta tttacaacaa catgaaacaa   2280
ttcatcagat atctcatctc atctaacgtc ggagaagtcg tctccatctt catggtcgcc   2340
gcactcggaa ttccagaggc tctcattcca gttcaacttc tctgggttaa cttggtcact   2400
gacggtcttc cagccactgc tctcggattc aatccaccag atcttgacat tatggacaga   2460
catccacgtt cagccaacga tggactcatc tctggatggc tcttcttcag atatcttgct   2520
gtcggaacct acgtcggagt tgccaccgtc ggagcctcaa tgtggtggtt cttgttgtac   2580
gaggagggac cacagatcac ctactaccag ctcactcact ggatgagatg tgaaatcgag   2640
ccagacaact tgccgatct tgactgcgcc gtattcgagg acaatcaccc gaacgccatg    2700
gctctgtccg tgcttgtcac cattgagatg ctcaacgcca tcaactcact ttccgagaat   2760
caatcgcttt tagtgatgcc accatggaag aacatctggc tgatggccgc catttccctt   2820
tcgatgtctc ttcactttgt cattctctac gttgacatca tggccaccat cttccagatc   2880
```

-continued

```
acccctctca actgggtcga atggatcgcc gtgttgaaga tctcactgcc agtgctcctt    2940
ctcgatgaaa ttctcaagtt catcgccaga aactacatcg acggtaagcc ggagacggtc    3000
ggcgcgaagg cacgtagtgc catctcgctg ctcgcctggg tgtctgtgac gctcgcctac    3060
tttgcgtgga tgttgggccc gtacgccgag ctcattaacc atgcgctcgt cggtccatct    3120
gtcgatccgt cgaaattcga cgcggttgtc acgcccgaca agttacataa cgaattgtga    3180
```

<210> SEQ ID NO 7
<211> LENGTH: 2994
<212> TYPE: DNA
<213> ORGANISM: Sus sp.

<400> SEQUENCE: 7

```
atggagaacg cgcacacaaa gacggtggag gaggtgctgg gccacttcgg cgtcaacgag      60
agcacggggc tgagcctgga gcaggtcaag aagctcaagg agagatgggg ctccaacgag     120
ttaccggctg aagaagggaa aaccttgctg gaacttgtga ttgagcagtt tgaagactta     180
ctcgttagaa ttttattgtt ggcagcatgt atatcttttg ttttggcttg gtttgaagaa     240
ggcgaagaaa caattacagc ctttgtagaa ccctttgtaa ttttacttat attagtagcc     300
aatgcaattg tgggtgtatg gcaggaaagg aatgcagaaa atgccatcga agcccttaag     360
gagtatgagc ctgaaatggg caaagtgtat cgacaggaca ggaagagtgt acaacgaatt     420
aaagctaaag acatagttcc tggtgatatt gtagaaattg ctgttggtga caaagttcct     480
gctgatataa gattaacgtc catcaaatct actactctaa gagttgacca gtcaattctc     540
acaggtgagt ctgtctctgt catcaagcac accgaccctg tccctgaccc acgggctgtc     600
aaccaagata agaagaacat gctcttttct ggtacaaaca tagcagctgg caaagccatg     660
ggagtggtgg tggcaactgg agttaacact gaaattggca agatccggga tgaaatggta     720
gcaacggaac aggagagaac accctccag cagaaactag atgagtttgg ggaacagctt     780
tccaaagtca tctcccttat ttgcattgca gtctggatca taaacattgg gcacttcaat     840
gacccggttc atggaggctc ctggatcaga ggtgctattt attactttaa aattgcagtg     900
gccctggctg tagcagccat tcctgaaggc ctgcctgctg tcattaccac ctgcctggct     960
cttggaactc gtagaatggc aaagaaaaat gccattgttc gaagtctccc ttctgtggaa    1020
acccttggtt gcacttccgt tatctgctca gacaagactg gtacacttac aacaaaccag    1080
atgtcagtct gcaggatgtt cattctggac aaagttgaag gtgatacttg ttccctgaat    1140
gagtttacca aactggatc aacatatgct cctattggag aagtccataa agatgataaa    1200
ccagtaaagt gtcatcaata tgatggtctt gtggaattgg caacaatttg tgctctctgt    1260
aatgactctg ctttggatta caatgaggca aagggtgtgt atgaaaaagt tggagaagct    1320
acagagactg ctctcacttg cctggtagag aagatgaatg tctttgatac tgagttaaag    1380 ggtcttttcta aaatagaacg agcaaatgcc tgcaactcgg tcattaaaca attgatgaaa    1440
aaggaattta ctctagagtt ttcacgtgat agaaaatcaa tgtcagttta ttgtacacca    1500
aacaaaccaa gccggacatc gatgagcaaa atgtttgtga agggtgctcc cgaaggtgtc    1560
attgacaggt gtacccacat tcgagttgga agtactaaag tccccatgac tcctggcgtc    1620
aaacagaaga tcatgtctgt cattcgggaa tggggcagtg gcagcgacac actgcgatgc    1680
ctggctctgg ccactcatga caacccgatg agaagagaag aaatgaacct tgaggattct    1740
gccaacttta ttaaatacga gaccaatctg actttcgttg gctgtgtggg catgctggac    1800
```

```
cctccaagaa tcgaagtggc ctcctctgtg aagctgtgcc ggcaggcagg catccgggtc   1860
attatgatca caggcgacaa caagggtacc gctgtggcca tctgccgtcg cattggcatc   1920
tttgggcagg acgaggatgt gacgtcaaag gcttttacag gtcgggagtt tgatgagctc   1980
aatccttcag cccagagaga agcctgcctg aatgcccgct gtttcgctcg agttgaacct   2040
tcccacaagt ctaaaattgt agaatttctt cagtcttttg atgagattac agctatgact   2100
ggggacggtg tgaatgatgc tcctgctctg aagaagtctg agatcggcat tgccatgggc   2160
tctggcaccg cggtggctaa aactgcctcc gagatggtcc tggctgatga caacttctcc   2220
accattgtgg ctgctgtgga ggagggacgg gcaatataca caacatgaa gcagttcatt   2280 cgctacctca tctcgtccaa cgtggggaaa gttgtctgta ttttcctgac agcagcccTT   2340
ggatttcctg aggctttaat tcctgtccag ctgctctggg tcaatctggt gacagatggc   2400
ctgcctgcca ctgcactggg gttcaatcct cctgatctgg acattatgaa caaaccaccc   2460
cggaacccaa aggaaccact gatcagtggg tggctctttt tccgctacct ggctattggc   2520
tgttacgttg tgctgctac tgtgggtgct gctgcgtggt ggttcattgc tgccgatggt   2580
ggtccgagag tgaccttcta ccagctgagt catttcctac agtgtaaaga ggacaaccca   2640
gactttgagg gagtggattg tgcagtcttt gaatccccct acccaatgac aatggcgctg   2700
tctgttctag tcaccataga gatgtgtaac gccctcaaca gtttgtcgga aaaccagtcc   2760
ctgctaagga tgccacccttg ggagaacatt tggctcgtgg gctccatctg cctgtccatg   2820
tcactccact tcctaatcct ctatgtggaa cccctgccac ttatcttcca gatcacaccg   2880
ctgaatttga cccagtggct gatggtgctg aaaatctcct tgcctgtgat tctaatggat   2940
gagaccctca gtttgtggc ccgcaactac ctggaacctg caatactgga gtaa          2994

<210> SEQ ID NO 8
<211> LENGTH: 2994
<212> TYPE: DNA
<213> ORGANISM: Homo sapiens

<400> SEQUENCE: 8
atggagaacg cgcacaccaa gacggtggag gaggtgctgg gccacttcgg cgtcaacgag     60 agtacgggc tgagcctgga acaggtcaag aagcttaagg agagatgggg ctccaacgag    120
ttaccggctg aagaaggaaa aaccttgctg gaacttgtga ttgagcagtt tgaagacttg    180
ctagttagga ttttattact ggcagcatgt atatctttttg ttttggcttg gtttgaagaa    240
ggtgaagaaa caattacagc cttttgtagaa ccttttgtaa ttttactcat attagtagcc    300
aatgcaattg tgggtgtatg gcaggaaaga aatgctgaaa atgccatcga agcccttaag    360
gaatatgagc ctgaaatggg caaagtgtat cgacaggaca gaaagagtgt gcagcggatt    420
aaagctaaag acatagttcc tggtgatatt gtagaaattg ctgttggtga caaagttcct    480
gctgatataa ggttaacttc catcaaatct accacactaa gagttgacca gtcaattctc    540
acaggtgaat ctgtctctgt catcaagcac actgatcccg tcctgaccc acgagctgtc    600 aaccaagata aaagaacat gctgttttct ggtacaaaca ttgctgctgg gaaagctatg    660
ggagtggtgg tagcaactgg agttaacacc gaaattggca agatccggga tgaaatggtg    720
gcaacagaac aggagagaac accccttcag caaaaactag atgaatttgg ggaacagctt    780
tccaaagtca tctccctTAT ttgcattgca gtctggatca taaatattgg gcacttcaat    840
gacccggttc atgagggGTC ctggatcaga ggtgctattt actactttaa aattgcagtg    900
gccctggctg tagcagccat tcctgaaggt ctgcctgcag tcatcaccac ctgcctggct    960
```

```
cttggaactc gcagaatggc aaagaaaaat gccattgttc gaagcctccc gtctgtggaa    1020
acccttggtt gtacttctgt tatctgctca gacaagactg gtacacttac aacaaaccag    1080
atgtcagtct gcaggatgtt cattctggac agagtggaag gtgatacttg ttcccttaat    1140
gagtttacca taactggatc aacttatgca cctattggag aagtgcataa agatgataaa    1200
ccagtgaatt gtcaccagta tgatggtctg gtagaattag caacaatttg tgctctttgt    1260
aatgactctg ctttggatta caatgaggca aagggtgtgt atgaaaaagt tggagaagct    1320
acagagactg ctctcacttg cctagtagag aagatgaatg tatttgatac cgaattgaag    1380
ggtctttcta aaatagaacg tgcaaatgcc tgcaactcag tcattaaaca gctgatgaaa    1440
aaggaattca ctctagagtt ttcacgtgac agaaagtcaa tgtcggttta ctgtacacca    1500
aataaaccaa gcaggacatc aatgagcaag atgtttgtga agggtgctcc tgaaggtgtc    1560
attgacaggt gcacccacat tcgagttgga agtactaagg ttcctatgac ctctggagtc    1620
aaacagaaga tcatgtctgt cattcgagag tggggtagtg gcagcgacac actgcgatgc    1680
ctggccctgg ccactcatga caacccactg agaagagaag aaatgcacct tgaggactct    1740
gccaactttt ttaaatatga gaccaatctg accttcgttg gctgcgtggg catgctggat    1800
cctccgagaa tcgaggtggc ctcctccgtg aagctgtgcc ggcaagcagg catccgggtc    1860
atcatgatca ctggggacaa caagggcact gctgtggcca tctgtcgccg catcggcatc    1920
ttcgggcagg atgaggacgt gacgtcaaaa gctttcacag gccgggagtt tgatgaactc    1980 aaccccctccg cccagcgaga cgcctgcctg aacgcccgct gttttgctcg agttgaaccc    2040
tcccacaagt ctaaaatcgt agaatttctt cagtcttttg atgagattac agctatgact    2100
ggcgatggcg tgaacgatgc tcctgctctg aagaaagccg agattggcat tgctatgggc    2160
tctggcactg cggtggctaa aaccgcctct gagatggtcc tggcggatga caacttctcc    2220
accattgtgg ctgccgttga ggaggggcgg gcaatctaca caacatgaa acagttcatc    2280 cgctacctca tctcgtccaa cgtcggggaa gttgtctgta ttttcctgac agcagccctt    2340
ggatttcccg aggctttgat tcctgttcag ctgctctggg tcaatctggt gacagatggc    2400
ctgcctgcca ctgcactggg gttcaaccct cctgatctgg acatcatgaa taaacctccc    2460
cggaacccaa aggaaccatt gatcagcggg tggctctttt tccgttactt ggctattggc    2520
tgttacgtcg gcgctgctac cgtgggtgct gctgcatggt ggttcattgc tgctgacggt    2580
ggtccaagag tgtccttcta ccagctgagt catttcctac agtgtaaaga ggacaacccg    2640
gactttgaag gcgtggattg tgcaatcttt gaatccccat acccgatgac aatggcgctc    2700
tctgttctag taactataga aatgtgtaac gccctcaaca gcttgtccga aaaccagtcc    2760
ttgctgagga tgccccctg ggagaacatc tggctcgtgg gctccatctg cctgtccatg    2820
tcactccact tcctgatcct ctatgtcgaa cccttgccac tcatcttcca gatcacaccg    2880
ctgaacgtga cccagtggct gatggtgctg aaaatctcct gcccgtgat tctcatggat    2940 gagacgctca gtttgtggc ccgcaactac ctggaacctg caatactgga gtaa    2994
```

<210> SEQ ID NO 9
<211> LENGTH: 159
<212> TYPE: DNA
<213> ORGANISM: Sus sp.

<400> SEQUENCE: 9

```
atggataaag tccaataacct cactcgctct gctattagaa gagcttcaac cattgaaatg    60
```

```
cctcaacaag cacgtcaaaa ccttcagaac ctatttatca atttctgtct catcttaata    120
tgcctcttgc tgatttgcat catcgtgatg cttctctga                          159

<210> SEQ ID NO 10
<211> LENGTH: 837
<212> TYPE: DNA
<213> ORGANISM: Caenorhabditis elegans

<400> SEQUENCE: 10
aaagtgaata atcgaccaaa taataactca ctttggtatt tattcctgtc ttataatgtt     60
atgtatgaat taaattcata tgcatatggc tcactctgac aaaaaaaaat aatcttccag    120
atcaatattg actaccgatg cgggtggtct tttgctttga attctgctga actttacacc    180
ccgaacagca atgtgtgctt cagctaaaaa aaagtaagtg tgttaatcag tcccccgat    240 tcttcatttt ttgcccctct ctccgtttc gtcggcaaaa aagagaaaa taagataag     300 tctcaagata ggttggtaat cgctaaagtg gttgtgtgga taagagtagc aaaatggcag    360
gaagagcact ttgcgcgcac acactgtact cattgttctg ataaaaattc tctcgttgtt    420
tgccgtcgga tgtctgcctc tctgccattg agccggcttc ttcactatct ttagttaacc    480
taaaatgccg tttctttct cgtatcccac tatccgttga ggttctctgc tctcttcgct    540
cccttaccgc cagcgagcaa ctatccgtgg gggcgccttg ctcggaagat ggggggaag     600 aaagaagatt tttgctattt gcacttgaga aagagacttt tcctgcgtcg atggttagag    660
aacagtgtgc agacactttt cagctaccta gatacatgga tatccccgcc tcccaatcca    720
cccacccagg gaaaaagaag ggctcgccga aaaatcaaag ttatctccag gctcgcgcat    780
cccaccgagc ggttgacttc tctccaccac ttttcatttt aaccctcggg gtacggg       837

<210> SEQ ID NO 11
<211> LENGTH: 2396
<212> TYPE: DNA
<213> ORGANISM: Caenorhabditis elegans

<400> SEQUENCE: 11
agcttgggct gcaggtcggc tataataagt tcttgaataa ataattttc ccgacaaaac     60 atgagtattt ctttcgaaaa taaaagtgca ggctaattag agattattct gtaattaact    120
gcataatttg tcacgtgcca tagttttaca ttccactacg tcatagttct taaaatacta    180
atctcctgaa aatagaagta ggtgaagaaa gtttaattat cagttctaaa atgacaattg    240
atctttggaa tatgttctga aactaccgat cattgaacag atgctatttg aatgatatag    300
aattgtatat ttgcaatttc tgaaacgcgt tcttaaaggc acacagatta attcaaaagg    360
gtctggccgc aaaaaggttt atggtggccg atttgagtt ttgtgtgtga ttgcttttc     420 acaatcagtg ttttcaggat tatgtgatga actagatctt caagtttcgt tacatttcat    480 atgtttttcgg aactcacgaa gtacatattg ggtattgtgc tcaaaaaatt cagcaatcag    540
cttcgctccg ctgactttag aacccaaaaa aatagtatgg ccaaactgac tgtgttacga    600
tcatttcaat ttttcaatac atatttaaga tttctaagag taagaaggtc aaaaactgtt    660
ctggaataca tatatatttt tcaggttaca attagtcaaa aagtgcactg aaatatacgt    720
tttaatttca cgaataaccc aattagttca atgtatttt ggtcaaccaa cgttaaagtt     780
tggcttccaa ccaattatca tttctgatca accacaatgt tttttcttta tctgcaagtt    840
aattttttat ttttatccag atgtttgca tatttttcaa ttcttcacta gcgcccactt     900
cttgcacttc cggcgccctg aatctaatgc atctgttgca agaattgaaa gaccaatcaa    960
```

```
cacattgttt tcttcacgag atactgaaga aaatgaataa aaacagagaa aaagagccat    1020
gtgattagtg acaactgttg ctaacagata ccatagcttg gacttggtac gtgatggcaa    1080
cgtatgggtc aacaaaaatg attgcagagg gggtgcaaaa cagtcaagtc gagaaaatat    1140
gaaaaacaga aaacaaagaa cagaaaaatg ggtttgagag tcagtataat ttataaaaga    1200
aaaattgtac atagaaatta accatttttg tagaagaagt tattttttcaa gcatcgttaa    1260 aaattattca aagcaccta tttcatattt aattttaaac atggttaaat gaacaacacg    1320
gtgcgcaatc aggaaaactt gaaatctgaa actgttgttg tgatcttctt cgcaactgtt    1380
cagatagcac tagtgtaatg ttaagagtgc gcgaatataa tggaatataa tggatcacac    1440
ctcctgccat caggtaaacg tctctgttat cacatatttc caactattaa attttacct    1500 tttacagttt tacattttt tgaaaaagt aacttttgt cttcaaaatc cctgacgaaa    1560
atatcaaata ttttaatcga gactgcagag gaaccgattg atgatttgga aaatccagct    1620
ttacctgtgt aagaactgaa aagtttcata accctagggt attcccagtt acattcccca    1680
ctggctaaca atagcaccca gttttttcatc acctttcttc aaatttctcg gcgatttgtt    1740
aaaaacaaaa tttgtgtccc ttctctgata tctctatgtc tctaaacaca agttcatcgg    1800
aaaacgaagg agggtaggtg ttggttgggc tcccgaagtg aaaatagaag agcaagaata    1860
gaatattaga gagagagtgc agagagggcg ggatagctcc cgggattccg ttttcttctt    1920
ctttatcttc aacgatgatg tgtgtgcgtg ttgtatagat tctgttgctc ccccacaact    1980
cgctccgaag gctcaataca attcaattga tattggagga gagcctaccg gagtgggagg    2040
ataagaagaa acataagaag aagaagaaga agaagcatgc ttctggtttt tgatgctatg    2100
aaaacggcac aaaaagatga ttgaggtccc ttttcaatac cttctctcat ctttcaaatc    2160
ccattgaaac ctaaaacttc tcaccacgct ttaccattgt tctccaaaaa cttatagcaa    2220
tgtctataac tttttatct ctgaaaagca gtgttccatt tttcttttc ctattttatt    2280 tcaattgttt ctcacatttc gtttggattc tttgcttgtc aaccagcttc ttcttccact    2340
tttaccgtct aattttcagg gcagggagcc atcaaaccca cgaccactag atccat      2396
```

<210> SEQ ID NO 12
<211> LENGTH: 45
<212> TYPE: DNA
<213> ORGANISM: Caenorhabditis elegans

<400> SEQUENCE: 12

```
ccttctcgat ttcaaaatgt caactaaaca tatgcaacat atgtg              45
```

<210> SEQ ID NO 13
<211> LENGTH: 159
<212> TYPE: DNA
<213> ORGANISM: Artificial Sequence
<220> FEATURE:
<223> OTHER INFORMATION: Description of Artificial Sequence:HUMANIZED
      PIG PLB cDNA

<400> SEQUENCE: 13

```
atggagaaag tccaataccct cactcgctct gctattagaa gagcttcaac cattgaaatg    60
cctcaacaag cacgtcaaaa ccttcagaac ctatttatca atttctgtct catcttaata   120
tgcctcttgc tgatttgcat catcgtgatg cttctctga                          159
```

<210> SEQ ID NO 14
<211> LENGTH: 52

<212> TYPE: PRT
<213> ORGANISM: Sus sp.

<400> SEQUENCE: 14

```
Met Asp Lys Val Gln Tyr Leu Thr Arg Ser Ala Ile Arg Arg Ala Ser
 1               5                  10                  15

Thr Ile Glu Met Pro Gln Gln Ala Arg Gln Asn Leu Gln Asn Leu Phe
             20                  25                  30

Ile Asn Phe Cys Leu Ile Leu Ile Cys Leu Leu Leu Ile Cys Ile Ile
         35                  40                  45

Val Met Leu Leu
     50
```

<210> SEQ ID NO 15
<211> LENGTH: 52
<212> TYPE: PRT
<213> ORGANISM: Homo sapiens

<400> SEQUENCE: 15

```
Met Glu Lys Val Gln Tyr Leu Thr Arg Ser Ala Ile Arg Arg Ala Ser
 1               5                  10                  15

Thr Ile Glu Met Pro Gln Gln Ala Arg Gln Asn Leu Gln Asn Leu Phe
             20                  25                  30

Ile Asn Phe Cys Leu Ile Leu Ile Cys Leu Leu Leu Ile Cys Ile Ile
         35                  40                  45

Val Met Leu Leu
     50
```

<210> SEQ ID NO 16
<211> LENGTH: 2251
<212> TYPE: DNA
<213> ORGANISM: Caenorhabditis elegans

<400> SEQUENCE: 16

```
gaacgaaatg ctgaatcggc catcgaagcg ctcaaggaat acgaaccaga aatggccaag      60
gtcatccgat ccggacacca cggaattcag atggttcgcg ctaaggaact cgtgccagga     120
gatcttgtcg aagtttcagg ttagcaaaaa cttttttttt taactttcaa attttaaacc     180
atatattttt cagtcggaga caagatccca gccgatctcc gtcttgtgaa gatctactcc     240
accaccatcc gtatcgatca gtccatcctc accggagaat ctgtgtctgt tatcaagcac     300
accgactctg tgccagatcc acgcgctgtt aaccaggaca agaagaattg tctgttctcg     360
ggaaccaatg tcgcatctgg aaaggctcgt ggaatcgtct tcggaaccgg attgaccact     420
gaaatcggaa agatccgtac cgaaatggct gagaccgaga atgagaagac accacttcaa     480
cagaagttgg acgaattcgg agagcaactt tccaaggtta tctctgttat ttgcgttgct     540
gtttgggcta tcaacattgg acatttcaac gatccagctc acgtggatc atgggttaag     600
ggagcaatct actacttcaa aatcgccgtt gctcttgccg tcgctgctat tccagaagga     660
cttccagctg tcatcaccac gtgccttgcc ctcggaactc gccgtatggc caagaagaac     720
gctattgtaa gatcccttcc atccgtcgaa actcttggat gcacatctgt tatctgctct     780
gacaagactg gaactctcac caccaaccag atgtctgtgt caagatgtt catcgctgga     840
caagcttctg gagacaacat caacttcacc gagttcgcca tctccggatc cacctacgag     900
ccagtcggaa aggtttccac caatggacgt gaaatcaacc cagctgctgg agaattcgaa     960
tcactcaccg agttggccat gatctgcgct atgtgcaatg attcatctgt tgattacaat    1020
```

-continued

```
gagaccaaga agatctacga gaaagtcgga gaagccactg aaactgctct tatcgttctt    1080
gctgagaaga tgaatgtttt cggaacctcg aaagccggac tttcaccaaa ggagctcgga    1140
ggagtttgca accgtgtcat ccaacaaaaa tggaagaagg agttcacact cgagttctcc    1200
cgtgatcgta aatccatgtc cgcctactgc ttcccagctt ccggaggatc tggagccaag    1260
atgttcgtga agggagcccc agaaggagtt ctcggaagat gcacccacgt cagagttaac    1320
ggacaaaagg ttccactcac ctctgccatg actcagaaga ttgttgacca atgcgtgcaa    1380 tacgaaccg gaagagatac ccttcgttgt cttgccctcg gaaccatcga taccccagtc     1440
agcgttagca acatgaacct cgaagactct acccaattcg tcaaatacga acaagacatc    1500
acatttgtcg gagtcgtcgg aatgcttgac cccccaagaa ctgaagtttc ggactcgatc    1560
aaggcttgta accacgctgg aatccgtgtc atcatgatca ccggagacaa caagaacacc    1620
gctgaggcta tcggaagaag aatcggactc ttcggagaga acgaggatac cactggaaaa    1680
gcttacactg gacgtgaatt tgacgatctt ccaccagagc aacaatctga agcctgccgc    1740
agagctaagc ttttcgcccg tgtcgagcca tctcacaagt ccaagattgt cgatatcctt    1800
caatcccagg gagagattac tgctatgacc ggagacggag tcaacgacgc tccagctttg    1860
aagaaggccg aaatcggaat ttctatggga tcaggaactg ctgtcgccaa gtctgcatct    1920
gaaatggttc ttgctgacga taacttcgca tccattgtgt ctgctgtcga agaaggacgt    1980
gctatttaca caacatgaa acaattcatc agatatctca tctcatctaa cgtcggagaa     2040
gtcgtctcca tcttcatggt cgccgcactc ggaattccag aggctctcat tccagttcaa    2100
cttctctggg ttaacttggt cactgacggt cttccagcca ctgctctcgg attcaatcca    2160
ccagatcttg acattatgga cagacatcca cgttcagcca acgatggact catctctgga    2220
tggctcttct tcagatatct tgctgtcgga a                                    2251
```

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer oGK21

<400> SEQUENCE: 17

```
tggactcatc tctggatggc tc                                               22
```

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: primer oGK22

<400> SEQUENCE: 18

```
cttctccttt actcatcaat tcgttatgta acttgtcgg                             39
```

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence:primer oGK23

<400> SEQUENCE: 19

```
gaactataca aatagttgaa gttcttctaa ccccc                                    35
```

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: primer
      oGK24

<400> SEQUENCE: 20

```
gcgtttatcc ttgattggag cttc                                                24
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: primer
      oGK25

<400> SEQUENCE: 21

```
gaatggatcg ccgtgttgaa g                                                   21
```

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: primer
      oGK26

<400> SEQUENCE: 22

```
ttctcccttta ctcatgtcgc gtttatcctt gattgg                                  36
```

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: primer
      oGK27

<400> SEQUENCE: 23

```
gaactataca aatagaaatg acagtgctcc ctcaatc                                  37
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: primer
      oGK28

<400> SEQUENCE: 24

```
gtgggatcct ggtttgttct gag                                                 23
```

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: primer
      SERCA P2

<400> SEQUENCE: 25

```
cgaaagagcac gaagatcaga cag                                                23
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: primer SERCA P8

<400> SEQUENCE: 26
gagaggcggt tggtttggg                                                19

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: primer SERCA P4

<400> SEQUENCE: 27
ccgttcgtca tccttctcat tc                                            22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer SERCA P7

<400> SEQUENCE: 28
cgacagatgg accgacgagc                                               20

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: primer oGK33F256V

<400> SEQUENCE: 29
caacagaagt tggacgaagt cggagagcaa ctttc                              35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: primer oGK34F256V

<400> SEQUENCE: 30
gaaagttgct ctccgacttc gtccaacttc tgttg                              35

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: primer oGK118

<400> SEQUENCE: 31
gccagtcgga aaggtttcca aggacgacaa gccagttaac ccagctgctg gagaatt      57

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: primer oGK119

<400> SEQUENCE: 32
aattctccag cagctgggtt aactggcttg tcgtccttgg aaacctttcc gactggc      57

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: primer oGK108

<400> SEQUENCE: 33
gaccgtacga aattttcagg aaaggaatgc agaaaatgcc      40

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: primer oGK109

<400> SEQUENCE: 34
ccccggccgg ccttactcca gtattgcagg ttccagg      37

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: primer oGK51

<400> SEQUENCE: 35
gctctagatg gataaagtcc aatacctcac      30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: primer oGK52

<400> SEQUENCE: 36
gctctagatg gagaaagtcc aatacctcac      30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: primer oGK55

<400> SEQUENCE: 37
ggggtacctc agagaagcat cacgatgatg      30

```
<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: primer
      oGK56

<400> SEQUENCE: 38
ggggtaccat gagaagcatc acgatgatgc aaatc                              35

<210> SEQ ID NO 39
<211> LENGTH: 6
<212> TYPE: PRT
<213> ORGANISM: Caenorhabditis elegans

<400> SEQUENCE: 39

Lys Asp Asp Lys Pro Val
  1               5
```